(12) United States Patent
Tran et al.

(10) Patent No.: US 12,304,166 B2
(45) Date of Patent: *May 20, 2025

(54) SYSTEMS AND METHODS FOR MASS CUSTOMIZATION

(71) Applicant: Bao Tran, Saratoga, CA (US)

(72) Inventors: Bao Tran, Saratoga, CA (US); Ha Tran, Saratoga, CA (US)

( * ) Notice: Subject to any disclaimer, the term of this patent is extended or adjusted under 35 U.S.C. 154(b) by 1562 days.

This patent is subject to a terminal disclaimer.

(21) Appl. No.: 16/375,831

(22) Filed: Apr. 4, 2019

(65) Prior Publication Data

US 2019/0232592 A1    Aug. 1, 2019

Related U.S. Application Data

(63) Continuation of application No. 15/097,003, filed on Apr. 12, 2016, now Pat. No. 10,293,565.

(51) Int. Cl.
| | | |
|---|---|---|
| *B29D 35/12* | (2010.01) | |
| *A43B 3/34* | (2022.01) | |
| *A43B 7/08* | (2022.01) | |
| *A43B 13/18* | (2006.01) | |
| *A61B 5/00* | (2006.01) | |
| *A61B 5/103* | (2006.01) | |
| *B29C 33/38* | (2006.01) | |

(52) U.S. Cl.
CPC .............. *B29D 35/122* (2013.01); *A43B 3/34* (2022.01); *A43B 7/088* (2013.01); *A43B 13/181* (2013.01); *A61B 5/1038* (2013.01); *A61B 5/6807* (2013.01); *A61B 5/7282* (2013.01); *B29C 33/3835* (2013.01); *B29D 35/12* (2013.01)

(58) Field of Classification Search
CPC .... B29D 35/122; B29D 35/12; B29D 35/128; A43B 3/34; A43B 7/088; A43B 13/181; A43B 13/187; A61B 5/1038; A61B 5/6807; A61B 5/7282; B29C 33/3835; A43D 1/02

See application file for complete search history.

(56) References Cited

U.S. PATENT DOCUMENTS

| | | | | |
|---|---|---|---|---|
| 10,293,565 | B1 * | 5/2019 | Tran ...................... | A43B 13/181 |
| 10,299,722 | B1 * | 5/2019 | Tran ...................... | A61B 5/112 |
| 2005/0071935 | A1 * | 4/2005 | Shah ...................... | A43D 1/025 |
| | | | | 12/146 L |
| 2007/0152379 | A1 * | 7/2007 | Jacobson ............. | B29C 43/3642 |
| | | | | 264/500 |
| 2008/0134541 | A1 * | 6/2008 | Bar-Haim ............. | A61B 5/1038 |
| | | | | 36/27 |
| 2009/0316965 | A1 * | 12/2009 | Mailling ............. | G01B 11/2545 |
| | | | | 382/128 |
| 2013/0204145 | A1 * | 8/2013 | Shah ..................... | A61B 5/0205 |
| | | | | 709/201 |
| 2014/0182170 | A1 * | 7/2014 | Wawrousek ............. | A43B 5/02 |
| | | | | 702/155 |
| 2015/0351665 | A1 * | 12/2015 | Ross .................... | A61B 5/0002 |
| | | | | 702/44 |

* cited by examiner

*Primary Examiner* — Mohammad Ali
*Assistant Examiner* — Sheela Rao
(74) *Attorney, Agent, or Firm* — PatentPC PowerPatent

(57) ABSTRACT

A footwear having a sole customized to a wearer's anatomy by receiving a foot model; generating an elevated foot model with a heel at a predetermined heel height from a ground and determining a structure to support a foot arch and a ball area of the foot model; and fabricating a high heel sole with the optimized structure to support the foot.

18 Claims, 10 Drawing Sheets

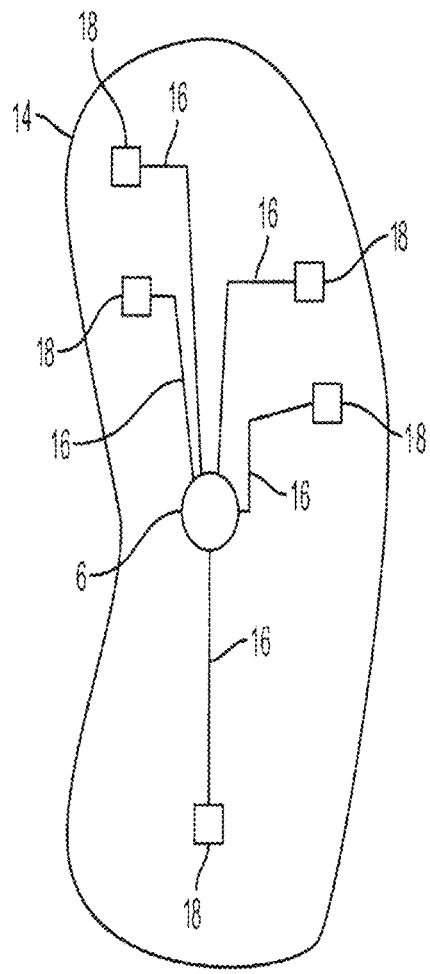

| |
|---|
| Capture 3D model of patient anatomy (30) |
| Isolate foot region (32) |
| Create 3D model with anatomically accurate shape and size of foot region (34) |
| Morph or project the shape/size of orthotics change to minimize stress onto the 3D model of patient (36) |
| Allow user to iterative change foot model shapes/ sizes until satisfied with new shape (38) |
| Allow user to select from a library of shoes to provide realistic simulation (40) |
| Custom fabricate the shoes to achieve desired shape and size (42) |

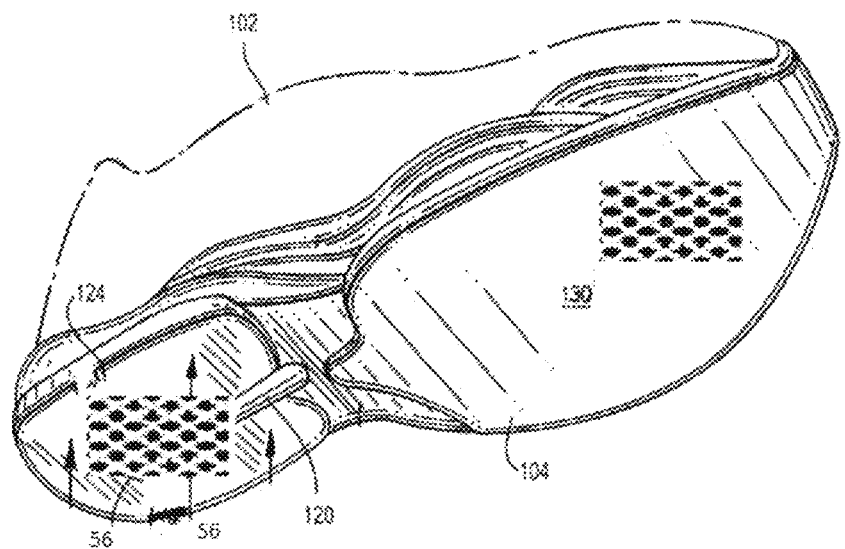

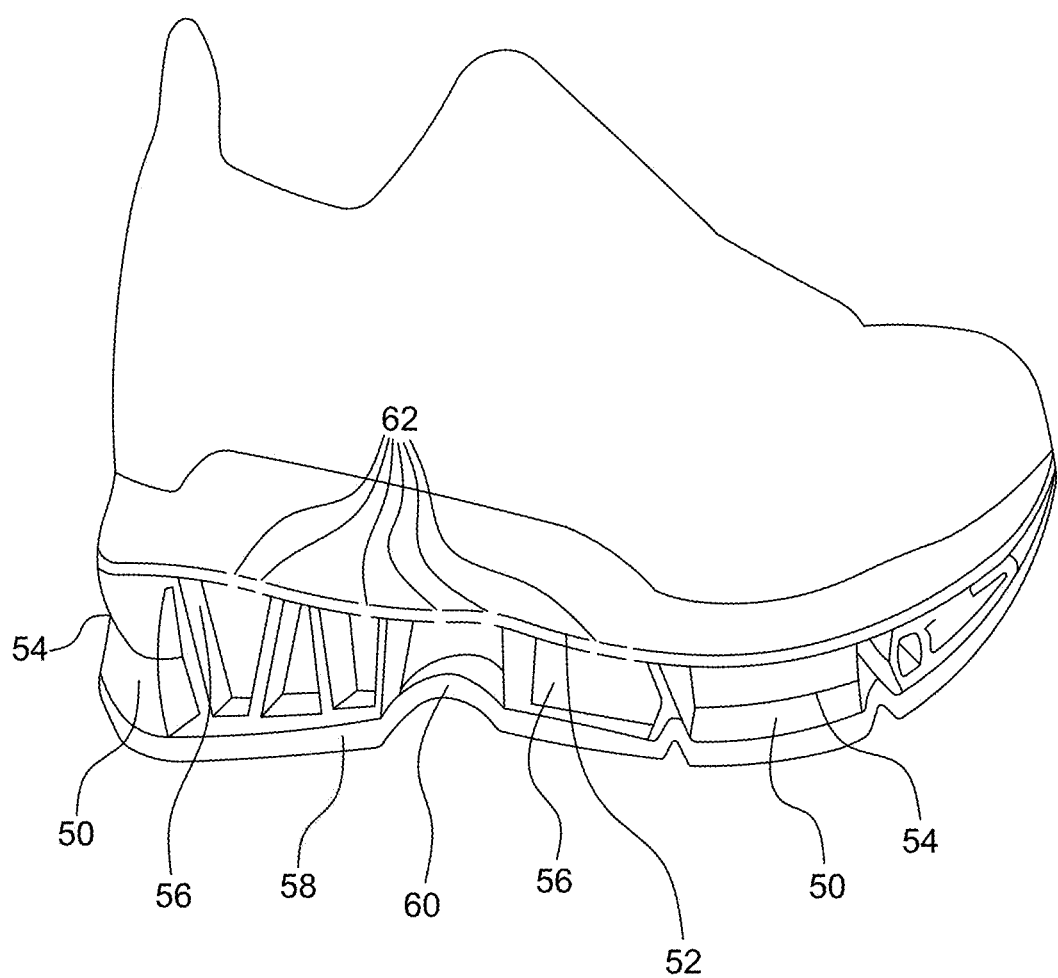
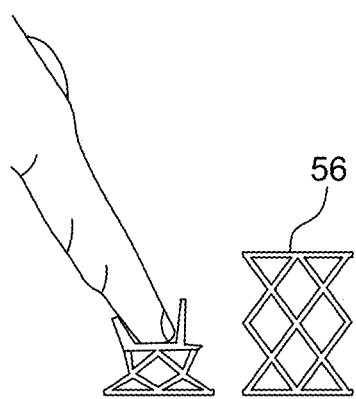
FIG. 1D

| |
|---|
| Establish patient registries and get permission for access to DBs (Apple Healthkit, Samsung SHealth, Microsoft HealthVault,...) |
| Collect health data covering all aspects of patient health: EMRs, provider DB, fitness wearable devices, pharmacy records, credit card purchass, phone purchases ... |
| Monitor calorie burn, EKG, physical activity via footwear device |
| Determine risk information of an individual for example, one or more of: risk of the individual contracting a specific disease; a population risk that indicates whether the individual can benefit from clinical intervention; a level of priority for the risk score; a disease flag that indicates the type of disease for which the individual is at risk; a likelihood of hospitalization score that indicates the probability that the individual will require hospitalization; and, a numerical risk score indicating probability of illness |
| Measure clinical and cost metrics |
| Establish and adhere to complex clinical practice guidelines and send provider with clinical practice guidelines |
| Perform disease risk-management outreach/ Educate patients and engage with patients |
| Track specific outcomes (success and failure) and find factors leading to success and vice versa |

FIG. 1I

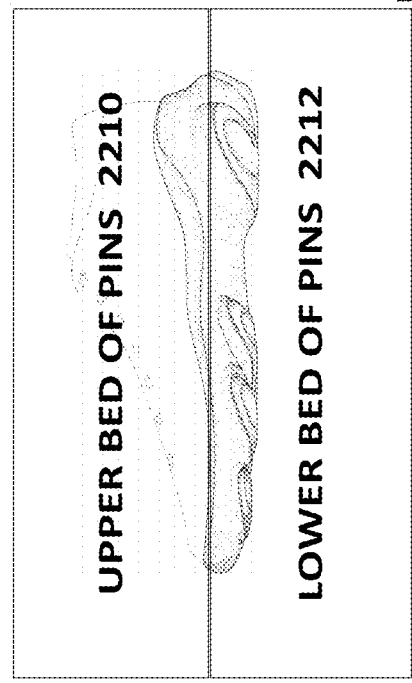

FIG. 2E

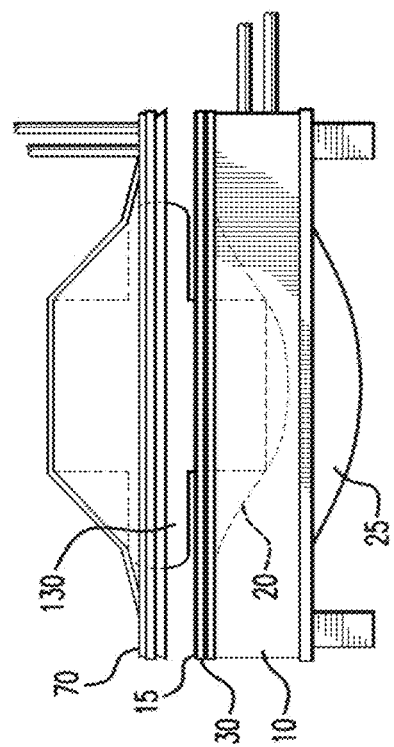
FIG. 3C
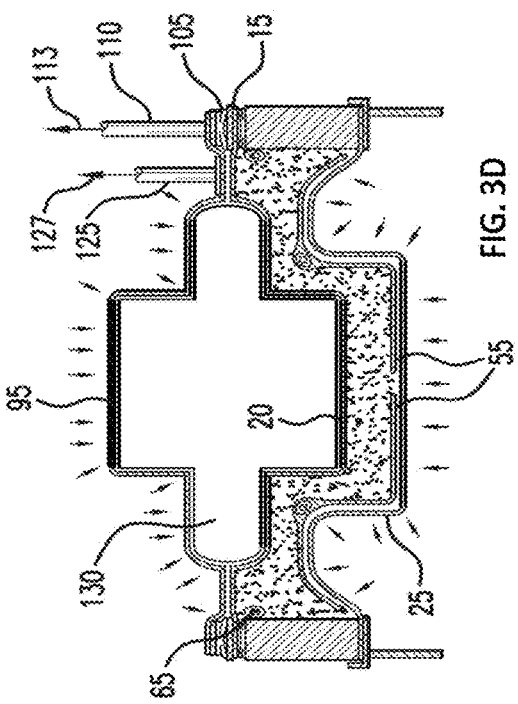
FIG. 3D
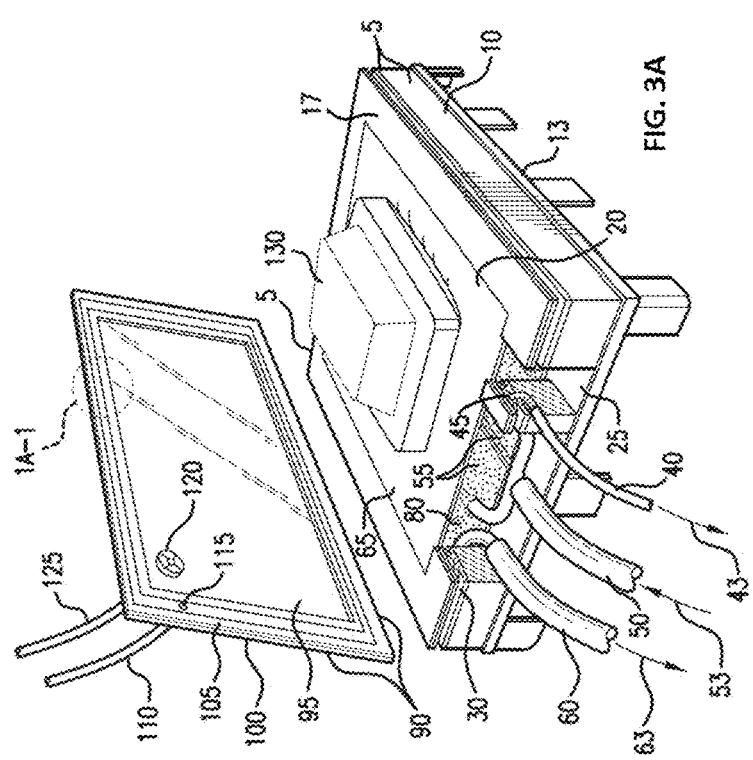
FIG. 3A
FIG. 3B

| |
|---|
| receiving a foot model into memory coupled to a processor (401) |
| generating an elevated foot model with a heel at a predetermined heel height from a ground and determining a structure to support a foot arch and a ball area of the foot model (403) |
| fabricating a high heel sole with the optimized structure to support the foot (405):<br><br>    forming a reformable master shape from the foot model with the optimized structural lattice;<br><br>    holding a volume of particles inside a container<br><br>    infusing the volume with a liquid to mobilize the volume of particles<br><br>    pressing the reformable master shape into the membrane with atmospheric pressure to form a mold of the sole<br><br>    depositing a sole material into the mold |

FIG. 4

SYSTEMS AND METHODS FOR MASS CUSTOMIZATION

The present system relates to mass-customization.

BACKGROUND

The increase in demand for shoes for sports and outdoor activities such as walking, running, hiking, and playing tennis, basketball and like sports has prompted many advances in shoe design to improve protection and comfort to the feet, ankles, legs, hips, etc., especially to improve cushioning, shock absorption, and stability at the heel.

Typically, the sole of the shoe and any design included in the sole is manufactured before the shoe is assembled using steel cutting dies and die-cutting machinery that create the tread design of the sole. Sole designs can also be created through injection molding, with the assembly taking place after the production of the sole. With these methods the bottommost layer of foam or rubber has the design die cut or molded into it. Once the bottom layer has been molded, or die cut and the die cut material removed, the footwear is assembled, and the bottommost layer of the sole is adhered to the rest of the footwear. Because of the cost of producing the steel cutting die or producing a mold for injection molding, these two production methods are cost-effective for creating large numbers of the same style of tread pattern but are typically not cost effective for generating a small number of shoes.

SUMMARY

A number of aspects are disclosed herein. Systems and methods are disclosed for digitizing 3D models of the foot for subsequent engineering and fabrication of foot-related products such as shoes and inserts, among others. Systems and methods are disclosed for mass customized design and fabrication of foot-related products such as shoes and inserts, among others. Systems and methods are disclosed for corrective footwear. Systems and methods are disclosed for customizing shoe/footwear appearance. Systems and methods are disclosed for custom inserts. Systems and methods are disclosed for performing health management based on foot traffic and other health data. Systems and methods are disclosed for Multi-Phase 3D manufacturing, and in on embodiment of footwear and shoes. Systems and methods are also disclosed for monitoring a user's fitness or health using foot products. Additionally, systems and methods are disclosed for managing population health based on the foot products.

In one particular aspect, a footwear having a sole customized to a wearer's anatomy, the sole formed by receiving a 3D model of a sole having a volume, generating a structural lattice inside the volume of the sole, updating the structural lattice to provide strength while using reduced material, optimizing the structural lattice to maximize energy absorption by the sole, and 3D fabricating the sole with the optimized structural lattice; and sensors coupled to the sole to detect foot pressure and movement data. In one embodiment, the footwear communicates with a network to monitor the wearer's health, the network having computer code to: saving the weight and movement data from the footwear into a health data repository separate from the clinical data repository; mining the clinical data repository and health data repository for patients sharing similarity with the wearer, including one or more similar biomarkers associated with health conditions; identifying at least one similar health conditions and identifying one or more corrective actions recorded in the repository and the result of each action for the one or more health conditions; presenting the corrective action and result to the wearer and recommending an action to reduce risk from the predicted health condition; and monitoring the health condition using updates in the clinical data repository and health data repository.

Advantages of the system may include one or more of the following. The system provides highly functional shoes that are customized to each wearer at a reasonable cost of manufacture. Further, the system provides the ability for the user to design his/her own shoe appearance for full consumer satisfaction. The system can be used to mass-customize other products such as protective head gear, custom seats, among others. The system's sensors can detect falls, epileptic seizures and heart attacks in older people and susceptible individuals—and then send alarm signals to caregivers or emergency response teams. The shoe sensors can be used in combination with interactive gaming and Virtual Reality environments and augmented feedback systems to facilitate home-based rehabilitation for physiotherapy, patients with heart disease, and ageing individuals. Using sensors in the foot, the efficacy of treatments and outcomes of clinical trials can be better assessed. They help to track physiological changes from chronic conditions, as well as the progress of treatments on a continuous basis. By combining physiological sensors with activity monitors in the foot, the system can provide early detection of symptoms and adverse changes in a patient's health status—facilitating timely medical interventions.

BRIEF DESCRIPTION OF THE DRAWINGS

The exact nature of this system as well as advantages thereof will be readily apparent from consideration of the following specification in conjunction with the accompanying drawings in which like numerals designate like parts through the figures thereof and wherein:

FIG. 1B is a block diagram illustration of footwear with pressure sensors.

FIG. 1C shows an exemplary process executed by the hardware of FIG. 1A.

FIG. 1D shows an exemplary shoe sole with shock absorbing arms formed with lattices, while FIG. 1E shows another shoe providing enhanced shock protection against heel impacts.

FIG. 1I shows an exemplary process to collect data from shoes and predict patient with health issues and proactively assist patients.

FIGS. 2A-2E show exemplary systems and techniques for manufacturing in volume with a wide range of materials for fabricating shoes at mass customization scale.

FIGS. 3A-3D show exemplary system for fabricating shoe products using a reformable material and shaping system, which is commonly assigned with the instant systems and methods.

FIG. 4 shows an exemplary process to produce a mass-customized high heel shoe, while

DESCRIPTION

The following describes systems and methods for mass-customization of objects and devices. In one example, mass-customized shoe fabrication is described. This is done first by generating a 3D model of the feet, adjusting the model to optimize foot performance or compensate for foot deformities, rendering the model as a reformable 3D physical model, and fabricating a pair of shoes using rapid mass-customized production techniques that can fabricate each shoe sole in less than 10 minutes.

Foot Shape Sensing and 3D Modeling

Figure 1A:
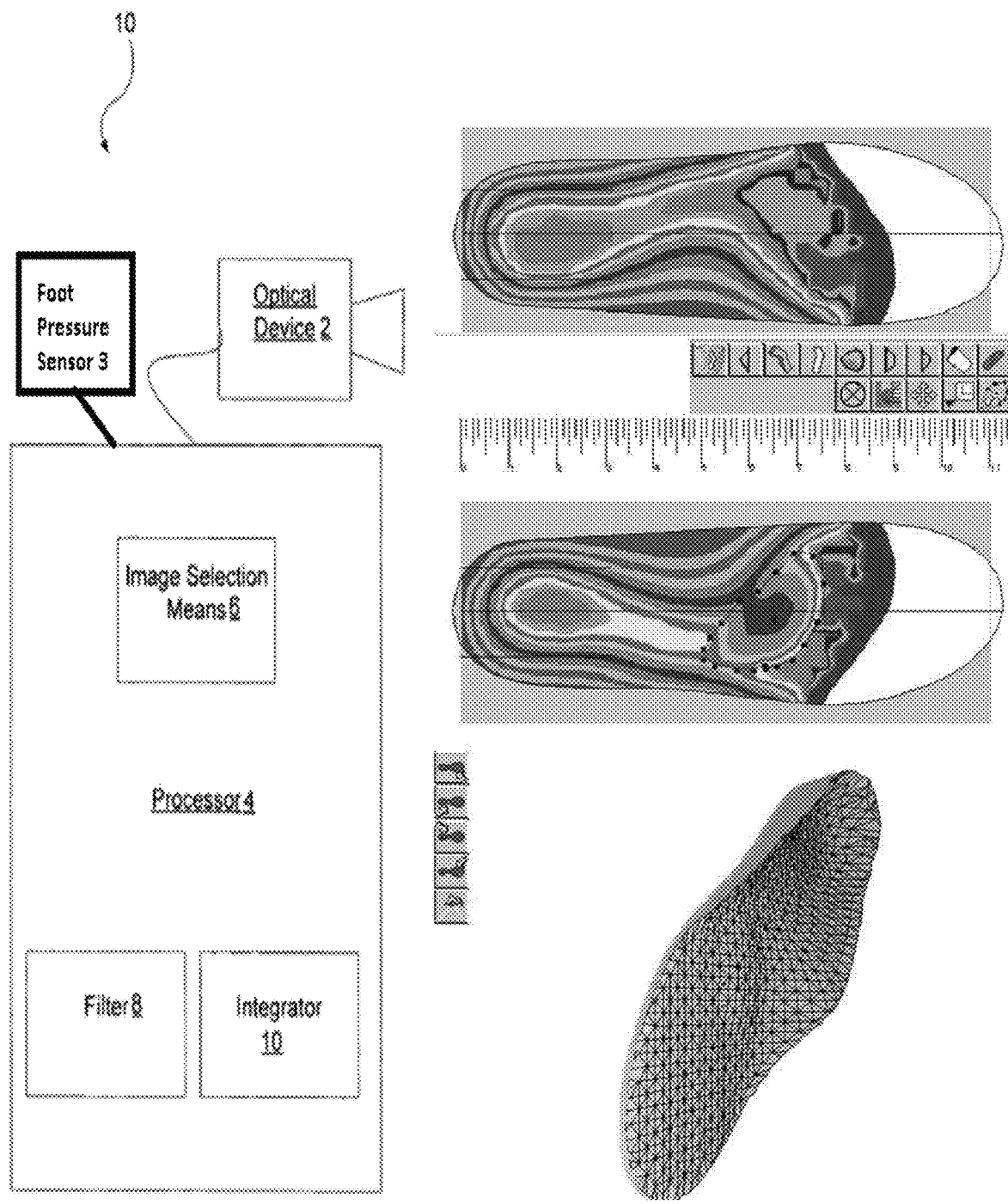
FIG. 1A shows an exemplary system to aid foot professionals such as physicians, sport doctors and foot orthodists to fabricate custom shoes to optimize the walking/running experience for a patient.

FIG. 1A shows an exemplary system to aid foot professionals such as physicians, sport doctors and foot podiatrists to fabricate custom shoes to optimize the walking/running experience for a patient. In this system, a foot pressure sensing system (14) and a 3D imaging system (10) senses the patient's foot conditions. The 3D imaging system (10) generally includes a camera or optical device (2) for capturing 3D images and a processor (4) that processes the 3D images to construct a 3D model. According to one exemplary embodiment, the processor (4) includes means for selecting 3D images (6), a filter (8) that removes unreliable or undesirable areas from each selected 3D image, and an integrator (10) that integrates the 3D images to form a mosaic image that, when completed, forms a 3D model.

One embodiment uses a camera in a smart phone as the optical device (2) to generate the 3D model from a plurality of images of the user's feet. The process breaks the foot images into individual points and calculates depth based on how they distort as the phone camera is moved and thus 3D geometry is generated with a live camera view. Another embodiment combines static pairs of photos to capture a single 3-D view of a scene. In one embodiment, the system photographs a patient's body in 3D, captures linear and volumetric measurements, and creates an exact three dimensional replica of the foot on screen. The doctor examines this model with the patient during the consultation, and performs proposed changes to the shoes which can be rendered to the patient to visualize the expected result in advance of an actual shoe production. In another embodiment, a 3D webcam is used with two cameras spaced roughly the same distance apart as human eyes, for the stereoscopic effect. 3D data acquisition and object reconstruction can be performed using stereo image pairs. Stereo photogrammetry or photogrammetry based on a block of overlapped images is the primary approach for 3D mapping and object reconstruction using 2D images. Close-range photogrammetry where cameras or digital cameras can be used to capture the close-look images of objects, e.g., body part such as feet, and reconstruct them using the very same theory as the aerial photogrammetry.

In yet another embodiment, the optical device (2) illustrated in FIG. 1A can be, according to one exemplary embodiment, a 3D camera configured to acquire full-frame 3D range images of objects in a scene, where the value of each pixel in an acquired 2D digital image accurately represents a distance from the optical device's focal point to a corresponding point on the object's surface. From this data, the (x,y,z) coordinates for all visible points on the object's surface for the 2D digital image can be calculated based on the optical device's geometric parameters including, but in no way limited to, geometric position and orientation of a camera with respect to a fixed world coordinate, camera focus length, lens radial distortion coefficients, and the like. The collective array of (x,y,z) data corresponding to pixel locations on the acquired 2D digital image will be referred to as a "3D image". Alternatively, the 3D camera can simply be two cameras spaced apart at a predetermined distance to provide 3D perspective capture. 3D image integration can be done using pre-calibrated camera positions to align multiple 3D images to merge the aligned 3D images into a complete 3D model. More specifically, cameras can be calibrated to determine the physical relative position of the camera to a world coordinate system. Using the calibration parameters, the 3D images captured by the camera are registered into the world coordinate system through homogeneous transformations. While traditionally effective, this method requires extensive information about the camera's position for each 3D image, severely limiting the flexibility in which the camera's position can be moved. The data capture can be viewed in an exemplary modeling system, according to one exemplary embodiment. The exemplary modeling system can support 3D image acquisition or capture, visualization, measuring, alignment and merging, morphing, editing, compression and texture overlay, all controlled using a database manager.

Next, using a CAD tool, a professional can specify shoe soles as biomechanical medical appliances that are custom made to correct a wearer's specific foot imbalance. Features are specified that affect insole comfort and effectiveness, such as the medial/lateral arch shape and offset, insole contour and thickness, shock absorbing heel pad, cushioning top layer, insole length and shape to maximize flexibility in 1st MPJ joint, and heel cup shape and depth.

The plastic body of the custom orthotic helps to re-align the foot by redirecting and reducing certain motion that takes place during the gait cycle. The finished shoes are made from precise 3D scans or imprints of the wearer's feet. The custom orthotics help position the foot so the wearer will be using the right muscles at the right time, minimizing fatigue and allowing his/her muscles to be used more efficiently.

Sensors can be incorporated into the mass-customized shoe products. Sensors and wearables can be integrated into various accessories such as garments, hats, wrist bands, socks, shoes, eyeglasses and other devices such as wristwatches, headphones and smartphones. Multiple digital health sensors can be integrated into sensor networks comprising other body-worn sensors and/or ambient sensors. Some monitoring systems can assist the gathered sensor and wearbles data to be uploaded to a remote site such as a hospital server for further clinical analysis. With the advent of cloud-computing, many wearable sensor systems can now be easily upgraded without the need for user installation of software in their monitoring devices, which makes it easier and cheaper to maintain the health monitoring system networks.

The resulting 3D model can be synthesized as a physical device using the systems and methods disclosed below for shaping a reformable material by holding a volume of particles inside a container having a first elastomeric membrane surface; infusing the volume with a liquid to mobilize the volume of particles; and pressing a master shape into the membrane with atmospheric pressure. Alternatively, the model can be printed using various 3D printing techniques such as selective laser sintering, among others.

Monitoring of Foot Pressure and Health Parameters

In one embodiment, in addition to the 3D modeling, actual foot pressure can be captured and used for treatment or for analysis to optimize the wearer's walking/running/climbing performance, among others. The foot pressure can be captured prior to fabrication of the shoes to optimize the shoe to the wearer. Alternatively, the foot pressure can be captured during use to optimize wearer performance.

FIG. 1B is a diagram illustration of footwear 4 with pressure sensors 18. Footwear 4 may be a removable insert for a shoe. Footwear 4 may also be a sole of a shoe, a sandal, a sock, sock type device, or a boot. Footwear 4 contains a plurality of pressure sensors 8 connected by connections 16 to a medical node 6. Pressure sensors 18 may be resistive pressure sensors, but are not limited to resistive pressure sensors and can be a variety of other types of pressure sensors as well as other physiological and biomechanical sensors. In either case, medical node 6 receives raw data from pressure sensors 8 and generates pressure data for transmission to a local base station. Although FIG. 1B only depicts five pressure sensors, it is understood that the number of pressure sensors may vary. As many pressures sensors as needed are contemplated. Medical node 6 can process the raw data from pressure sensors 18 to generate the pressure data. The transmitter is used to transmit the pressure data to the base station 10 such as a Bluetooth PC or mobile phone, for example. In operation, pressure sensors 18 sense pressure from a foot placed on them. The pressure sensor can be piezoelectric sensors, capacitive sensors, or resistive sensors. For example, where pressure sensors 18 are resistive sensors, the resistance in primary pressure sensors 18 varies as different pressure and/or force is applied to them. Medical node 6 sends current through pressure sensors 18 and determines the pressure at each pressure sensor 18 from the resistance detected. Based on the pressure, the shoe can be customized to compensate for any unsuitable pressure experienced by the wearer and optimize the walking experience.

In addition to pressure sensing, other personal data can be captured. For example, the sensors can include foot bioimpedance sensors that use bioelectrical impedance analysis (BIA) to estimate the heart rate by amplifying the pulsatile impedance component superimposed on the basal impedance. One embodiment detects the heart rate (HR) from bioimpedance measured in a single foot. Four electrodes are used for measurement of bioimpedance signal; two electrodes for injecting current and the other two to capture the voltage signal from human body. The bio-impedance signal shows deflections corresponding to systole and diastole activity as a measure of heart rate. The electrodes embedded in the footwear 4 apply a 50 kHz voltage between the outer electrode pairs and measure the drop in voltage across the inner electrode pairs in one embodiment. An impedance converter AD5933 separates impedance into real and imaginary part using discrete Fourier transform. The real and imaginary values of the measured bio-impedance signal are processed by a processor to obtain a continuous signal. The bioimpedance signal obtained after de-noising using adaptive thresholding. For heart rate detection, synchronous demodulator plays vital role by demodulating the bio-impedance signal from current carrier. To achieving high CMRR in signal in analog differential synchronous demodulator for AC signals, the signal is synchronously demodulated using the floating-capacitor with high CMRR. An impedance analyzer is used for getting bio-impedance signal. Wavelet thresholding methods can be used for noise removal where wavelet coefficients are threshold in order to remove their noisy part.

Another embodiment measures heart rate and/or EKG with sensors directly provided in the footwear 4 or using external wearable devices and such data combined with foot-ground contact information is used for ambulatory estimates of maximal aerobic power from foot. The user's maximal rate of oxygen uptake sets the upper limit for sustained physical activity and is the standard measure of aerobic fitness.

Figure 1F:
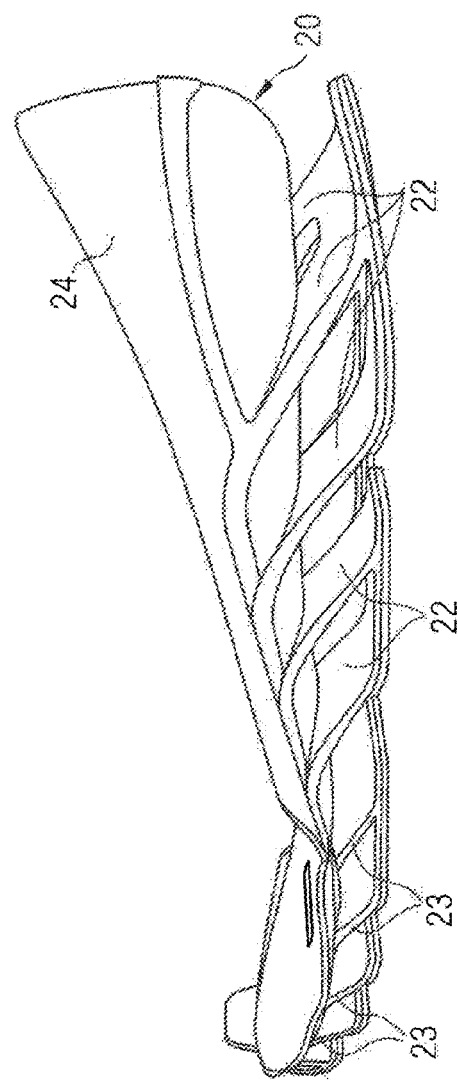
FIGS. 1F and 1G show embodiments with piezoelectric energy generator and shock absorbing elements, while FIG. 1H show operation of the shock cancelling footwear.
Figure 1G:
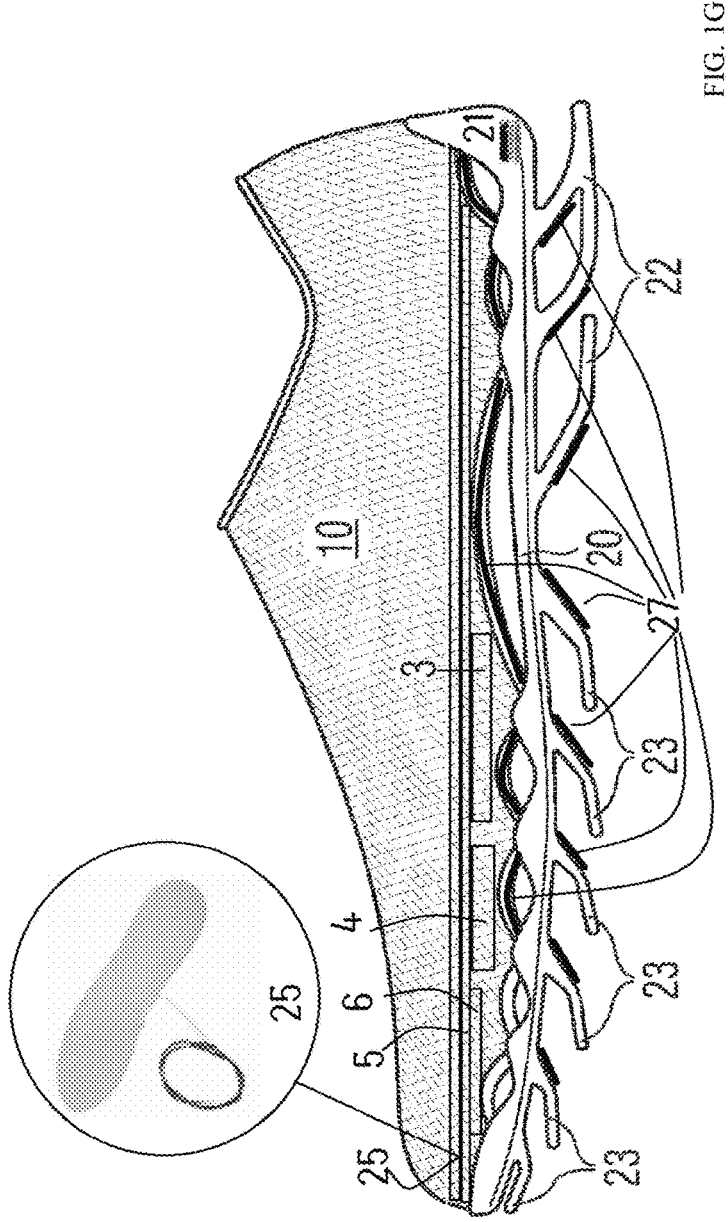

The footwear 4 can include piezoelectric elements that generate electricity and also can be actuated to cancel or dampen vibrations, as shown in FIG. 1F and FIG. 1G. In this piezoelectric embodiment, a shoe body is positioned above a base that includes a plurality of spring blades or leaf spring elements. Each spring blade has a top portion that extends from the base in a curved manner and a bottom portion secured to a blade foot. The blade can be plastic springs, which get compressed with each foot strike and recoil as the wearer proceeds through the gait cycle. In one embodiment, the base and the spring blade can be a piezoelectric composite that is directly molded into the shape of the base and the spring blades. The base can be an energy storage device, as detailed below. In another embodiment, the base is connected to individually tuned blades designed to propel runners. In one embodiment, 16 blades are composed of a highly elastic, piezoelectric polymer that is angled forward for high energy return in any environment. In addition, each blade is tuned to provide support in each phase of a runner's stride. The shoe can spring back with each step and propel a runner forward. The blades have different thicknesses and angles, which can influence the amount and direction of that energy return. Each blade is "tuned" differently to correspond to its position on the shoe, as well as to take into account body mass; men and women will get shoes with the appropriate amount of flex and response.

In an embodiment, the base can have a flexible and stretchable battery composed of strain free LiFePO4 cathode, Li4Ti5O12 anode and a solid poly ethylene oxide (PEO) electrolyte as a separator layer. Featuring solid thermoplastic electrolyte as a key enabling element this battery is potentially extrudable or drawable into fibers or thin stripes which are directly compatible with the weaving process used in smart textile fabrication. In an embodiment, a materials system for the design of a drawable lithium polymer battery with a view of eventually obtaining a battery-on-fiber is disclosed. The cathode material used in one embodiment is LiFePO4. While the base or sole can be the battery, the upper or flexible portion covering the foot can also include the battery or a suitable energy harvesting device such as solar cell.

The shoe has an upper surface (upper) that can be fabric, leather, or synthetic materials for cooling/warming the foot. One embodiment of the shoe 10 covers the upper surface with a solar electricity generator whose output is connected to a power regulator. Inside the shoe, a sole contains a piezoelectric device covering the entire foot is used to generate electricity. In one embodiment, the sole can be a piezo sole from Smart-Material Corp. of Sarasota, FL. The shoe also contains electronics such as CPU, transceivers, energy store (such as batteries or super-capacitors) and power regulator. The regulator can accept electric output from a variety of sources including piezoelectric devices and solar cells, for example. The sole plate can include a connector such as a micro USB connector to recharge a flexible energy storage device such as a flexible battery, or alternatively can be a flexible supercapacitor. The shoe can also receive recharge through inductive charging or other wireless charging systems. In one embodiment, the human foot electrically touches a pad on the shoe to provide contacts for a BAN communication network with sensors mounted on the wearer's body. As noted above, the sensors can be an EMG detector, EEG detector, an EKG detector, an ECG detector, a bioimpedance sensor, an electromagnetic detector, an ultrasonic detector, an optical detector, a differential amplifier, an accelerometer, a video camera, a sound transducer, or a digital stethoscope. The bioimpedance sensor can determine one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss, heart attack, stroke attack. The sensor can also communicate with an indoor position sensor, a motion sensor, a door sensor, a bathroom sensor, a water overflow sensor, an exercise equipment sensor, a smoke detector, an oven sensor, a cooking range sensor, a dish washer sensor, a cabinet door sensor, a refrigerator sensor, a refrigerator container sensor, a kitchen water flow sensor, a dish sensor, a bowl sensor, a chair sitting sensor, a sofa sitting sensor, a bed sensor, a weight sensor, a television viewing sensor, a radio listening sensor.

Corrective Footwear

Once the feet are digitized, corrective shoe adjustments can be done. FIG. 1C shows an exemplary process executed by the hardware of FIG. 1A. In this process, the system captures 3D model of patient (30). The process then isolates the patient's foot region (32). Next, the process models shape and size of the foot adjustments (34) and morphs or projects the shape/size of the shoe change onto the 3D model of patient (36). The process allows the professional or the patient to iterative change shoe support shapes/sizes until the patient is satisfied with new shape (38). The process can also allow the user to select from a library of shoes to provide realistic simulation (40). When the patient selected his or her shape/size, then the system fabricates the custom shoes (42).

In one embodiment, the sole is customized to the user's foot shape based on the captured data. A user can wear the foot sensor, run a quick lap on a treadmill, and instantly generate data to form a custom-made pair of 3D printed running shoes, tailored to the cushioning needs of his/her individual foot and capable of enhancing his/her athletic performance.

The 3D model of the foot is applied along with the pressure sensor data to create optimal footwear. Computer software such as Autodesk Crispin Shoemaker CAD software can be used to adjust an upper surface of the sole to provide an orthotic footbed. The method includes optimizing the orthotic footbed to support the foot, align a wearer body, balance weight distribution, increase stability, reduce foot fatigue and stress on wearer joint.

One embodiment is a diagnosis and a system for design of patient-specific orthotics focused principally on dealing with the kinetics of pronation. In the functioning foot there are specific relationships between the anatomical structures commonly identified from both the frontal plane and the sagittal plane of reference. Instability can result from a misalignment between the forefoot and rear-foot which prevents the foot from functioning in a fully integrated manner. However such a simple structural (kinematic) classification as this overlooks the critical matter of how muscular energy is transmitted through anatomical structures in such a way as to confer normal motion (kinetic function) on the foot. For example, the pronation force about the sub-talar joint axis is known to increase as a result of structural misalignment. But an analysis in kinetic terms would account for the origin and magnitude of the pronation force and why this force affects the sub-talar joint. Once the problem is presented in kinetic terms, the anatomical structures are seen to play their part in the resolution and transmission of forces rather than suggesting their source.

The system also models kinetic processes in the foot using Kirby's dynamic equilibrium between the sum of pronation and supination forces occurring about the sub-talar joint axis. ("Rotational Equilibrium" theory (Kirby, K. A. 2001 "Sub-talar joint axis location and rotational equilibrium theory of foot function" JAPMA 91(9): 465-487)), the content of which is incorporated by reference. Assessed from the sagittal plane of reference, the foot has been described as a compound pivot made up of three key pivots. The three key sagittal plane pivots can be named the "Heel rocker" the "Ankle Rocker" and the "Forefoot Rocker". Foot pronation results when a restriction occurs at either the ankle pivot or the forefoot pivot during gait. Restriction is revealed by the inability of the ankle or forefoot rocker to function normally. Restriction can be anatomical or physiological in origin and its extent can be influenced by footwear or orthotics or both. If restriction at a key pivot sites persists of foot becomes chronically unstable, pronation becomes endemic. This process can lead to deterioration in pivotal function and further instability.

The fabrication of an orthotic shoe for a patient's foot can be:
(a) wearering the foot to one or more of the following tests and ascribing a test value(s) within a predetermined set of relative values for each test which is indicative of one or more properties of the patient's foot:
(i) supination resistance test (as defined); and
(ii) Jack's test (as defined);
(b) recording each test value in a database;
(c) comparing the test values to control values indicative of one or more predetermined orthotic designs stored in the database; and
(d) selecting an orthotic design(s) from the predetermined orthotic designs dependent on that comparison.

The process may further include one or more of a skeletal integrity test, a fascial chord tension test, an ankle joint stiffness-lunge test, a principal activity velocity test, a sagittal plane morphology test, and a hamstring stiffness test. More explanation of the various tests is as follows:
(a) Supination Resistance Test—This is the amount of force required to resupinate the foot. With the patient standing in a relaxed weight bearing position, the force is graded on various levels and recorded from very low to very high. This index reveals where the centre of pressure is to be applied to the foot by the orthotic device, whether towards the back or the front. Foot integrity is also estimated from the amount of change in arch amplitude observed when the foot goes from a non-weight bearing position to a weight bearing. The change in arch amplitude may be measured within a range of five increments categorized from very low to very high; if the amplitude changes by two increments, the foot is classified as a foot with poor integrity, whereas if the change is just one increment the foot would be classified as one with good integrity. If there is no change then the integrity measure is scored as excellent. These integrity measures give further information for application of the design parameters that relates to the amount of rear foot to fore foot support.
(b) Windlass mechanism test—Jack's Test and Fascial Chord Tension Test. The force required to lift the hallux when the patient's foot is in a full weight bearing position is determined by The Jacks Test. When the hallux is lifted, the foot automatically begins to resupinate. The force to initiate the foot resupination is graded on three levels form low to high. This index provides additional information as to the placement of the centre pressure in the orthotic design. Fascial Chord Tension Test is as follows. With the foot non-weight bearing, the first metatarsal is dorsi-flexed and the prominence of the fascial chord is recorded. The prominence of the fascial chord is graded from low to high. This parameter is important as this allows the design to be modified to accommodate the fascial chord by way of a fascial groove. It is important to be able to adjust the design this way to help protect and facilitate the windlass effect. The orthotic design may require further adjustment including wedging in the rear foot to help push the chord out of the way.

(c) Sagittal plane morphology test. This categorizes the foot in terms of the gradient, the anterior calcaneal surface and the foot apex position. The gradient is evaluated as low, medium, or high. The foot apex position when combined with the gradient is categorized as rear, central, or forward, providing key information on the amount of soft tissue that surrounds the anterior heel area and can affect the amount of rear foot orthotic contour applied in the design.

(d) Hamstrings tension test. This is a test indicating the amount of tension in the hamstrings so as to determine the possible compensatory impact on the ankle joint in the close kinetic chain. Hamstring tension is graded on three levels low, medium and high. When the tension is categorized as high changes are made to the design so as to facilitate sagittal plane function.

(e) Lunge test. Failure in this test implies that greater ankle joint facilitation must be provided for in the design. The design will reflect the increased force needed to establish foot resupination.

(f) Principal activity velocity test. The principle activity velocity is defined as the level of activity the device is being designed for whether that is predominantly standing or moderate walking or running. The activity is graded on three levels from low to high. This is recorded as an index. When applied to the design it influences whether there is a need to more closely contour to the foot type or wedge more the rear foot area of the orthotic. The greater the velocity the greater the force of correction required and the further back the device apex should be.

Custom Appearance

The footwear can be custom produced at the request of a customer, who can specify the nature of the customization for one or more pairs of footwear. Each shoe of a pair of the footwear may have a different design, message or message portion designed into it and rendered using the bed of pins described below to make the custom shoe design messages or shapes, and then the bottom sole can be fabricated using the reformable bed described below. Once the negative is fixed in the reformable bed, suitable materials for the bottom sole can be deposited and cured and can include rubber, plastic, or foam. Further customization can be done by a Computerized Numerical Control (CNC) where component design can be integrated with computer-aided design (CAD) and computer-aided manufacturing (CAM) programs. The device can be programmed to use a number of different tools-drills, saws, and so on. Alternatively a number of different machines can be used with an external controller and human or robotic operators that move the component from machine to machine. Regardless, a series of steps needed to produce a part can produce a part that closely matches the original CAD design in a highly automated fashion. In accordance with aspects of the subject matter disclosed herein through the use of reformable bed and a suitably programmed CNC tools, customized footwear with custom cut sole designs, can cost effectively be created in small quantities and yet scalable for mass-customization.

1. A method of producing a component of customized footwear, the method comprising:
    capturing the 3D model of a foot and adjusting the 3D model to customize a shape to the foot to optimize foot performance;
    using a rapid prototyping machine such as 3D printer or a bed of pins to render a positive model of the shape; and
    impressing the positive model into a reformable mold to form the component of the footwear.

2. The method of claim 1, wherein the component comprises a sole.

3. The method of claim 1, comprising fabricating a plurality of components in parallel.

4. The method of claim 1, comprising generating a providing a series of plates comprising a receiving plate comprising a negative cavity shaped to receive a shoe and prevent the shoe from moving during cutting and wherein a thickness of the receiving plate is approximately a thickness of a sole of the shoe; securing the shoe comprising an upper and a sole, using the series of plates positioned on a computer numerical control machine table; and cutting a specified design into a bottom surface of the sole of the shoe using a computer numerical control machine.

5. The method of claim 1, comprising joining the component with an upper to form a shoe.

6. The method of claim 5, wherein the shoe comprises a jogging shoe, basketball shoe, soccer shoe, running shoe, climbing shoe, flip flop, sandal, or boot.

2. The method of claim 1, wherein the reformable mold comprises sand having a liquid state and a solid state.

Shock Protection

In one embodiment, the sole is not completely filled with material, but is formed as a lattice structure. The system generates triangulated surfaces for export to additive manufacturing (AM) processes. Implementing a process that coverts a CAD object into an image, known as voxelisation, the company uses an image-based method which allows designers to generate implicitly defined periodic lattice structures suitable for additive manufacturing applications and finite element analysis (FEA). The system generates robust lattice structures can overcome the problems faced with hollowing out a part to reduce weight and optimize designs prior to 3D printing. Cellular lattice structures can be used to replace the volume of CAD and image-based parts, reducing weight whilst maintaining optimal performance. In this way, the shoes can be light weight yet strong and provide shock impact absorption during running for the wearer.

Topology optimization can be used to drive the material layout including the lattice regions. From this new topology optimization implementation, the system can identify void regions in the design space, where the material can be removed, regions where solid material is needed, and regions where lattice structure is required. This allows the system to generate the optimal hybrid or blended solid-lattice design based on desired functionality of the part.

Lattice structures can be considered as porous structures. In the case of topology optimization, the semi-dense elements are like the porous media. To refine the design, a second-phase involves a detailed sizing optimization where the end diameters of each lattice cell member are optimized. This allows for further weight reduction while meeting design requirements, such as buckling, stress, and displacement.

FIG. 1D shows an exemplary shoe sole with shock absorbing elements formed with lattices. The shoe illustrated comprises one half of a symmetrical pair of footwear of a type that is commonly worn during sports and outdoor activities, such as walking, running, hiking, and playing tennis, basketball and like sports. FIG. 1D shows a side view of a shoe with a first embodiment of a shoe sole 50 according to the system, which takes this knowledge into account. A plurality of separate deformation elements 56, 60 are arranged between an outsole 58 and a load distribution plate 52. Deformation elements 56 made out of rubber or foamed materials are arranged in particularly sensitive areas of the sole, whereas lattice or honeycomb-like deformation elements may be arranged in other areas. Lattice structures such as those formed during 3D printing are formed as the arm structures of the elements 56 in one embodiment, and in another embodiment the entire sole is made up of lattices. One or more deformation elements 60 made out of rubber or foamed material are arranged at the rear end of the heel part of the sole in order to optimally cushion the peak loads on the foot arising during the first ground contact. In contrast thereto, honeycomb-like deformation elements 56 are preferably provided in the front section of the heel part to assist the rear end deformation element 60 and to assure in case of its failure, for example due to low temperatures, a minimum of elasticity of the shoe sole 60. The distribution of the deformation elements 56, 60 on the medial and lateral sides of the sole as well as their individual specific deformation properties can be tuned to the desired requirements, for example avoiding a supination or an excessive pronation, etc. In particular this can be done by using the above mentioned possibilities for an individual adaptation of the deformation properties of each individual honeycomb-like deformation element by a suitable geometrical structure and/or an appropriate material selection.

In another embodiment, the sole can be made of a piezoelectric material which generates electricity when the wearer walks. FIGS. 1F and 1G show embodiments with piezoelectric energy generator and shock absorbing elements.

In addition, the piezo material can be actuated to generate a vibration that cancels incoming shock on the wearer. In one embodiment, the system tracks the shock such as the foot contact patterns and generates an anti-vibration signal to cancel the shock generated when the foot contacts the ground. In this embodiment, a processor receives foot ground contact using an accelerometer. The stride pattern is determined, and the next foot ground contact is detected, and the piezo material is actuated with a counter signal to cancel the expected shock. This is similar to the noise cancellation, except the vibration/shock is canceled.

Figure 1H:
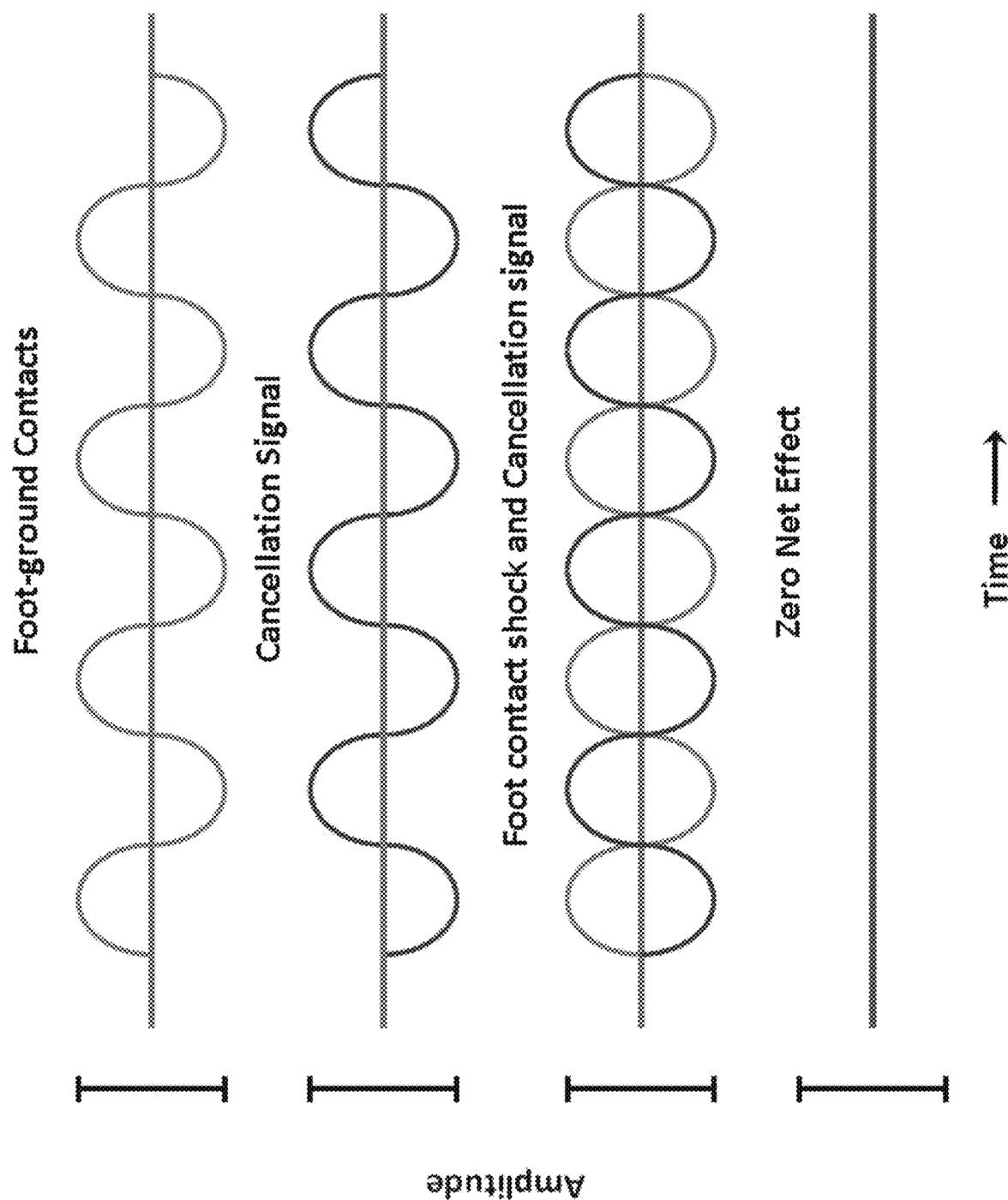

In one hybrid embodiment, the shoes incorporate passive and active isolation elements. The passive component consists of springs which support the load weight and provide isolation over a broad spectrum. These springs provide a basic level of isolation in the lower frequencies and excellent isolation in the higher frequencies (above 200 Hz). They also support the load while allowing for travel of the actuators in the active component. The performance of the springs is augmented and corrected by an active isolation component. The active isolation component consists of vibration sensors, control electronics, and actuators. The vibration sensors are piezo accelerometers. A plurality of sensors in each isolation system are positioned in different orientations to sense in all six degrees of freedom. The piezo accelerometers convert kinetic vibration energy into electrical signals which are transmitted to the control electronics, an example of which is shown in FIG. 1H. The electronics reconcile and process the signals from the various sensors using a processor. The electronics then send a cancellation signal to the actuators. The actuators generate vibrations that are equal to the incoming vibrations but out of phase in relation to the incoming vibrations. This results in cancellation of the incoming vibrational noise, leaving the wearer undisturbed. This process occurs within 5-20 milliseconds of a vibration entering the system.

Perspiration Protection

The shoe also provides a plurality of breathing openings 62 on the top of the soles. In this embodiment, a strip of Goretex™ or suitable material selectively permeable to air but not to water, or the like, can interface with the openings 62 and guard entrance into the foot chamber, yet allows breathability. The material is selectively permeable to air but not to water in the form of plugs covered in a microporous material which is permeable to air but not to water, to be inserted in a corresponding cavity provided in the internal area of the sole in such a way as to allow a water proofed closure of the internal end of the holes opening into the cavities themselves. Any other materials having its same properties can also be used, that is to say all those materials which counter the passage of water but not of air. These materials can finally have a variable thickness as required in order to achieve the necessary strength.

An arch-support may be provided so that the air is directly channelled inside the and therefore in an ideal position for being expelled to the outside. Implementations can include the following:

1. Transpiring sole structure comprising a sole having computer fabricated lattice structure including holes and means which are selectively permeable to air but not to water, wherein said holes open along part of the outer edge of said sole and wherein at least one cavity is provided inside said sole wherein said holes open, said means which are selectively permeable to air but not to water being attached for hermetic closure of said holes.

2. Transpiring sole structure according to claim 1, wherein said means which are selectively permeable to air but not to water, attached for a water proof hermetic closure of said hole are attached on the outlet of said holes.

3. Transpiring sole structure according to claim 1, wherein said means which are selectively permeable to air but not to water, attached for a water proof closure of said holes are attached inside said holes.

4. A transpiring sole structure according to claims 1 and 2, wherein said one cavity at least is in the form of a front cavity wherein the holes provided on the front part of the sole open, and a rear cavity wherein the holes provided on the heel of the sole open.

5. A transpiring sole structure according to claims 1 and 2, wherein said one cavity at least is in the form of a pair of right and respectively left front cavities, in which the holes provided on the right and respectively left front part of the sole open, and a pair of right and respectively left rear cavities, in which the holes provided on the right and respectively left rear part of the sole open.

6. A transpiring sole structure according to claims 1 and 2, in which said sole is of the cellular sole type, wherein said one cavity at least is in the form of perimetrical cells of said cellular sole, said series of holes opening on the external lateral walls of said cells.

7. A transpiring sole structure according to the previous claim, wherein passages are provided through the internal lateral walls of the internal cells of the cellular structure, said passages placing said cells in direct communication one with the other.

8. A transpiring sole structure according to claims 1 and 2, in which said sole is of the solid sole type, wherein said one cavity at least is in the form of a slot, extending substantially parallel to the outer edge of said solid sole, said series of holes opening on the external lateral wall of said slot.

9. A transpiring sole structure according to any one of claims 4 to 8, wherein said means which are selectively permeable to air but not to water are in the form of a strip of a microporous membrane which is permeable to air but not to water, covering the internal end of said series of holes which open inside said one cavity at least, said strip being attached to the external lateral wall of said one cavity at least by any known technique chosen from among gluing, sealing and waterproofed stitching.

10. A transpiring sole structure according to any one of claims 4 to 8, wherein said means which are selectively permeable to air but not to water are in the form of a series of microporous membranes which are permeable to air but not to water, each membrane of said series of membranes covering the internal end of a corresponding hole of said series of holes which open in said one cavity at least, said series of membranes being attached to the external lateral wall of said one cavity at least by any known technique chosen from among gluing, sealing and waterproofed stitching.

11. A transpiring sole structure according to any one of claims 4 to 8, wherein said means which are selectively permeable to air but not to water are in the form of at least one plug provided at said one cavity at least, said one plug at least having an external shape identical to said one corresponding cavity at least so as to be inserted perfectly therein, and wherein the external lateral wall of said one plug at least in contact with the external lateral wall of said one corresponding cavity at least is covered with a microporous membrane which is selectively permeable to air but not to water.

12. A transpiring sole structure according to the previous claim, wherein said one plug at least is made in a material which is permeable to air but not to water so as to allow a passage of air from and to the external environment.

13. A transpiring sole structure according to claim 11, wherein said one plug at least is hollow internally and has at least the external lateral wall and the upperwall perforated to allow a passage of air from and to the external environment.

14. A transpiring sole structure according to claims 11 to 13, wherein said membrane which is selectively permeable to air but not to water and which covers the external lateral wall of said one plug at least is attached to said lateral wall of said one corresponding cavity at least by any technique chosen from among gluing, heat-sealing, water proofed stitching or waterproof thrust joint.

15. A transpiring sole structure according to claims 1 and 3, wherein said means which are selectively permeable to air but not to water are in the form of a series of elements for transpiration corresponding to said series of holes, each element of said series of elements comprising an assembly of a first, a second and a third part, said first part being in the form of a hollow plug with open internal base and micro-perforated external base, and having such a shape so as to adapt to the corresponding hole wherein it is hermetically inserted, said second part being in the form of a layer of material which is selectively permeable to air but not to water, to be placed for a water proof closure of said open internal base, said third part being in the form of a counter-plug, axially open and inserted in said plug to block said layer between the internal lateral wall of said plug and the external lateral wall of said counter-plug.

16. A transpiring sole structure according to any one of the previous claims, wherein an arch-support, transpiring or perforated above, is provided, attached to the sole, wherein when said arch-support is perforated, the holes must involve at least the area above said one cavity at least.

17. A transpiring sole structure comprising a sole provided with holes and means which are selectively permeable to air but not to water, wherein said holes open along all or part of the external edge of said sole and in that said holes open directly on the upper surface of said sole, said means which are selectively permeable to air but not to water being attached for a water proof hermetic closure of said holes.

18. A transpiring sole structure according to the previous claim wherein said holes opening directly on the upper surface of said sole are covered by said means which are selectively impermeable to air but not to water formed by a membrane in material which is selectively impermeable to air but not to water, perimetrically attached onto the outline of the upper surface of the sole by any technique chosen from among gluing, sealing and waterproofed stitching.

Fluid Chambers for Shock Absorption

In another implementation, an exemplary embodiment of a shoe providing enhanced shock protection against heel impacts is illustrated in the exploded view of the sole FIG. 1E. The shoe 100 comprises a soft, flexible upper 102 that conformably surrounds an upper portion of a wearer's foot (not illustrated), and a sole 104 that is attached to the upper and thereby held between the wearer's foot and the ground or other contact surface (not illustrated). The upper 102 of the shoe 100 conventionally includes an opening through which the wearer's foot (not illustrated) is inserted into the shoe, a toe box, a vamp, a tongue, a pair of flaps disposed on opposite sides of and overlapping the tongue, and a lace extending through eyelets (not seen) in the flaps to secure the shoe on the wearer's foot, in a conventional manner. The upper may incorporate a laminated construction comprising sewn and/or bonded layers of soft, flexible leathers, plastic and/or cloth, and may have an interior surface that is padded for additional comfort.

The sole 104 includes an insole (not illustrated), a midsole (not illustrated), and an outsole that preferably comprises a strong, resilient, wear-resistant elastomer of compression-molded, synthetic rubber, e.g., neoprene or polyurethane. The outsole functions to absorb, i.e., store and dissipate, a portion of the shock and impact forces acting on the wearer's foot, but its primary functions are to increase the frictional coefficient between the shoe and the ground or other contact surface, thereby affording the wearer's foot with a non-slipping "traction", for which its lower surface 130 may be provided with cleats, lugs, lands and grooves, or the like (not illustrated), and to resist wear-abrasion of the lower surface of the shoe caused by its frictional engagement with the contact surface.

In other embodiment, the sole 104 can have fluid filled chambers for shock absorption. A heel cushioning component, preferably comprising a plurality of fluid-filled cushioning members in the sole 104 for cushioning heel impacts during use of the footwear. A lower surface 130, may be provided with cleats, lugs, lands and grooves, or the like (not illustrated), to resist wear-abrasion of the lower surface of the heel cover 108 caused by its frictional engagement with the contact surface. Each cushion can be constructed through molding sheets of plastic resin in molds configured with protrusions to provide the indentations in the material. One mechanism for forming each cushion is through thermoforming. Generally, thermoforming is a process of shaping plastic resin by heating a sheet or film of the plastic to a temperature at which the resin is sufficiently pliable to be shaped into a desired form and then forcing the material into a one-sided mold. Each cushion is preferably constructed by heating a first thermoplastic sheet to its forming temperature, heating a second thermoplastic sheet to its forming temperature, forcing the first thermoplastic sheet into a first mold configured to provide an upper molded sheet, forcing the second thermoplastic sheet into a second mold configured to provide a lower molded sheet, and joining together the two molded sheets by bonding, gluing, welding, fusing, coupling or the like. The molded sheets are configured to indent either or both of the upper and lower molded sheets at selected points or areas to provide internal support members. A particularly preferred construction method is to close together the upper and lower molded sheets while the material is at its forming temperature such that the upper and lower molded sheets are fused or welded together at their contact points or areas.

The sole and the cushion can be made of rubber or can be made of a thermoplastic resin. Preferable materials are those which are easily thermoformable into desired flexible configurations. Materials which can be thermoset after molding and retain the flexible characteristics for the sole components of the present system are included within the scope of preferred thermoformable materials. Thermoset resins solidify or set irreversibly when heated due to crosslinking between the polymer chains. Crosslinking can be achieved by using nucleating agents, mold temperatures above the materials forming temperature, radiation, etc. A thermoset resin once set or cured cannot be softened again by heating. Thermoset resins are generally characterized by high thermal stability, high dimensional stability and high rigidity and hardness and include resins such as polyesters and urethanes.

Thermoplastic resins can be either crystalline or amorphous and can be repeatedly softened by heating. Amorphous thermoplastics include acrylonitrile-butadienestyrene (ABS) copolymer, styrene, cellulosics and polycarbonates. Crystalline thermoplastics include nylons, polyethylene, polypropylene and polyurethane. Examples of particularly preferred materials for use in the present system include thermoplastic polyurethanes, nylons, polyesters, polyethylenes, polyamides and the like.

In accordance with another feature of the present system, the cushioning are sealed cushions having different resistances to compression, for example, by being filled with air, or other gas, or liquid at different pressures, e.g., below, at, or above atmospheric pressure, or by controlling the number, size and/or configuration of the indentations. The indentations 126 make that part of the cushion stiffer in compression than another part of the cushion without the indentations. For example, a difference in stiffness for compression between the medial side of the shoe and the lateral side of the shoe can be achieved. Or, a smaller hemispherical radius may be used for the indentations on one side of the shoe. These variations may be used to provide effective pronation or supination control through differences in compression between the medial and lateral sides of the shoe.

Thus, the stiffness or softness of each cushioning member is controllable and selectable at different areas of the heel. This feature enables the shoe to be designed with adjustable cushioning against heel impacts during use of the footwear.

1. A method of manufacturing a heel assembly for footwear, comprising:
   fabricating a sole with a lattice structure interior to absorb shock while minimizing footwear weight and material usage; and
   fabricating one or more heel cushioning components on the sole.

2. The method of claim 1, and configuring the heel cushioning component as a plurality of fluid-filled cushioning members, and spacing the cushioning members apart angularly around the heel post.

3. The method of claim 2, and forming a plurality of dividers on the outsole to extend radially of the heel post, and spacing the dividers angularly apart, and positioning and holding each cushioning member between a pair of the dividers.

4. The method of claim 1, comprising constituting the outer heel cover of a wear-resistant material.

5. The method of claim 2, comprising adhesively mounting the outer heel cover on the cushioning members in the assembled position, and adhesively mounting the cushioning members on the outsole in the assembled position.

6. The method of claim 2, comprising filling each cushioning member with air.

7. The method of claim 6, comprising juxtaposing a pair of sheets apart for each cushioning member, and forming a plurality of indentations in each sheet of the pair to extend toward the other sheet of the pair, and integrally connecting the indentations of the sheets of each pair to each other.

8. The method of claim 7, comprising configuring each indentation with a generally hemispherical shape, and configuring common welds formed at the integral connections of the indentations of the sheets of each pair to lay in a plane centrally between the sheets.

9. The method of claim 2, comprising configuring the cushioning members to have different resistances to compression.

Custom Insert

The system can work with conventional shoes by fabricating a custom insert based on the pressure sensor and the 3D information generated by the camera. The inserts can have a resistive heating element to warm up the foot. Sensors in the inserts can track user activities all day long. Calorie consumption can be determined continually. Shocks can also be measured continuously. Such inserts can include the following:

1. An article of footwear comprising: an insert having computer fabricated lattice structure therein and a heel member; the heel member and the insert are attached forming an insert system; and wherein the insert system is attached to an interior surface of the article of footwear.

2. The article of footwear according to claim 1, wherein the heel member and the insert are attached using a mechanical fastener.

3. The article of footwear according to claim 1, wherein the heel member includes a hole.

4. The article of footwear according to claim 3, wherein the hole of the heel member is configured to receive a protruding region disposed on the insert.

5. The article of footwear according to claim 4, wherein the protruding region is generally circular and the hole is generally round.

6. The article of footwear according to claim 4, wherein the protruding region is larger than the hole thereby creating an interference fit.

7. The article of footwear according to claim 1, wherein an outer surface of the insert system is smooth.

8. The article of footwear according to claim 1, wherein the heel member includes a first releasable fastener configured to attach to a second releasable fastener fixed to the inside surface of a footwear collar.

9. An insert for customizing an article of footwear comprising: a heel member configured to be removably insertable into a heel section of an upper of the article of footwear; and an insole portion attachable to the heel member and extending from the heel member towards a toe section of the upper of the article of footwear.

10. The insert of claim 9, wherein the heel member is attached to the heel section of the upper.

11. The insert of claim 10, wherein the heel member is attached to the upper with a hook-and-loop connector.

12. The insert of claim 11, wherein a section of the hook-and-loop connector is flush-mounted to the heel member, and wherein a corresponding section of the hook-and-loop connector is flush-mounted to the upper.

13. The insert of claim 9, wherein the insole portion is interference fitted to the heel member.

14. The insert of claim 9, wherein the insole portion is substantially flush to a sole portion of the article of footwear when inserted into the article of footwear.

15. The insert of claim 9, wherein the insert customizes a fit of the article of footwear.

16. The insert of claim 9, wherein the insert customizes performance of the article of footwear.

17. A foot insert fabricated by generating a 3D model of the feet, adjusting the model to optimize foot performance or compensate for foot deformities, rendering the model as a reformable 3D physical model, and fabricating the foot insert using rapid mass-customized production techniques that can fabricate each shoe sole in less than 10 minutes.

Real-Time Weighing System

The shoe can contain a weighing system to provide real-time measurement of the wearer's weight. Alternatively, a shoe pad insert or a sock or an adhesive band-aid can contain the weighing elements for temporarily measuring the wearer's weight. The system can have an array of force sensing resistors or weight sensitive sensors such as piezoelectric sensors. One embodiment can provide a resistor array in the form of a resistive (carbon) sheet with interdigitated contacts that can be shorted when weight is applied to change the overall resistance of the resistor. The resistor is calibrated to convert a predetermined resistance to a particular weight. The resistor can be flexible polymers to deal with loading conditions. In a liquid sensing embodiment, a fluid cavity or an array of fluid cavities is provided with a liquid that is displaced or pressurized as a function of weight. The array of cavities may be constructed to handle different pressures and sensitiveness. For example, a large cavity can be positioned under the foot section that absorbs most of the weight, and a small cavity can be positioned near the center of the foot as that part receives light pressure. With the single or array of cavities, a calibrated pressure sensor is used to detect weight. Alternatively, a pressure sensor can be embedded in the shoe, insert, sock, or band-aid to directly measure weight without the fluid cavity. The system can include temperature and altimeter sensors to better predict weight and to capture health parameters, for example. Using the sensors, a wearer can review his or her weight at nearly any time. Runners using such a system and device to know their hydration loss; chiropodists may wish to monitor weight distribution over a patient's feet; and athletic trainers may wish to analyze weight distribution and forces. In one embodiment, only a portion of the foot need to be covered, covering a certain percentage of the overall weight; and that percentage is scaled to a user's full weight. Weight and compression forces monitored in a shoe or shoe insert, in accord with the system, can further assist in gauging caloric and/or physical effort.

The weight sensors can communicate with processor in the sole or can communicate with a wireless phone using a personal area network such as Bluetooth or with a remote processor using WiFi, for example. The shoe weight is known and can be subtracted from the total weight to arrive at the wearer weight. Precise weight and heart rate measurement data can be used as part of a population health management system to keep patient weight to an ideal health. The weight information can be used to detect short term loss of water such as after marathon, race, soccer/football game, or intense outdoor activities such as hiking, for example. If weight loss indicative of dehydration, the processor can let the wearer know to drink water and rehydrate, for example. As the sensors also detect foot/ground impact, they can detect improper walking/running postures and report to users or doctors for corrective actions.

1. A system for determining weight, comprising:
   at least one sensor for insertion into a shoe and for generating signals indicative of weight and movement of the shoe;
   a processor configured to process the signals to determine at least one of: weight, speed and distance traveled of a person with the sensor.

2. The system of claim 1, the receiving device further comprising a mobile device or a watch having a wireless receiver to receive the information to display one of: weight, speed and distance.

3. The system of claim 1, the sensor being non-interfering with normal wear of the shoe by the person and being selectively insertable into and alternatively removable out of the shoe.

4. The system of claim 1, the sensor being part of a shoe insert that is insertable and removable from the shoe.

5. The system of claim 1, wherein the sensor comprises one of an accelerometer and a piezoelectric element.

6. The system of claim 1, comprising an audio player being configured to audibly recite weight, speed, or distance to the person.

7. The system of claim 6, further comprising headphones for connection to the MP3 player, for reporting the speed and distance traveled to the person.

8. The system of claim 1, wherein the sensor is in a shoe, a shoe insert, a sock, a band-aid.

9. The system of claim 1, comprising a phone having a wireless receiver to receive the information.

10. The system of claim 9, the phone reporting the information to the person through one or both of headphones connected with the cell phone and a display of the cell phone.

11. In a shoe, the improvement comprising:
    a weighing scale for selective insertion within the shoe, the movement monitoring device being non-interfering with normal wear of the shoe by a person and configured to generate wireless motion signals indicative of weight, speed and distance traveled of the movement monitoring device when inserted within the shoe.

12. In the shoe of claim 11, the further improvement comprising a watch for capturing the wireless motion signals and displaying one or both of the speed and distance traveled.

13. In the shoe of claim 11, the further improvement wherein the MP3 player audibly recites one or both of the speed and distance traveled to the person.

14. In the shoe of claim 11, the further improvement wherein the MP3 player displays one or both of the speed and distance traveled to the person.

15. In the shoe of claim 11, the further improvement wherein the movement monitoring device is both insertable and removable from the shoe.

16. In the shoe of claim 11, the movement monitoring device comprising (a) one of an accelerometer and a piezoelectric element and (b) a wireless transmitter.

Monitoring Device

A shoe-mounted or shoe-integrated device can monitor shoe usage and indicate when the shoe has exceeded its useful life. The sensor can detect events of the footgear due to activity of a wearer. The events can be impact events or rotational events, but are not limited to such events. For detecting impact events, the sensor can be an accelerometer responsive to motion. For detecting rotational events, the sensor can be a Hall-effect sensor, which can be responsive to a rotating element, such as a Ferris element. The processor can count the events detected by the sensor and maintain a cumulative event total. The processor can then compares the cumulative event total to an event threshold, which can be calculated from the predetermined number of events and an individualized factor. The individualized factor can include at least one of the wearer's weight, the climate where the footgear is worn, a type of predominate surface on which the footgear is worn, the wearer's age, the wearer's foot pronation or running style (such as whether the user is a heel striker or toe striker), and the wearer's injury history. The sensor, processor, and display can be secured within the footwear and communicates with a smart phone or a computer using a PAN such as Bluetooth and the sensor can be powered by a coin cell battery, solar cell, or piezoelectric electric generator.

The device can estimate distances run or can measure the shoe's operating parameters, such as cushioning. In a particular embodiment, the device can include a sensing unit, a programmable processor interpreting data from the sensing unit, and an indicator for notifying the wearer of the shoes' status. The processor can be programmed during manufacturing to incorporate typical variable values that are relevant to measuring shoe life. The processor can also be field programmed by the retailer or end user to enter individualized, wearer-specific variable values.

In one embodiment, a wear monitor can indicate when a shoe or component may have exceeded its expected useful life. The indication can be triggered by a measure of use, such as steps taken or distance accrued in the shoes, either through estimation or actual measurements. The monitor can take into account varies parameters related to the wearer of the shoe and environmental factors to more accurately determine when a pair of shoes has reached a wear out period. By employing sensors, the monitor can also be measure certain operating parameters of the shoe, such as the loss of a critical amount of resilience, and indicating to the wearer that the shoes are no longer adequate to protect the wearer from injury. The wear monitor can be fabricated into the shoe during manufacturing or can be a portable stand-alone device and can employ various technologies to provide a status indication to the wearer.

Another particular embodiment can include a method for estimating wear to a component of footgear based on the expected functional life of the component, as determined by a predetermined number of events. The method can include calculating an event threshold based on the predetermined number of events and an individualized factor, counting the events detected by a sensor, maintaining a cumulative event total, and comparing the cumulative event total to the event threshold. The method can also include displaying a representation of the comparison on a display device.

The individualized factor can include at least one of the wearer's weight, the climate where the footgear is worn, and a type of predominate surface on which the footgear is worn, the wearer's age, the wearer's foot pronation or running style (such as whether the user is a heel striker or toe striker), and the wearer's injury history.

The processor can calculate an event threshold based on the predetermined number of events and individualized factor, count the events detected by a sensor, from the counting, maintain a cumulative event total, and compare the cumulative event total to the event threshold. The individualized factor can include at least one of the wearer's weight, the climate where the shoe is worn, and a type of predominate surface on which the shoe is worn, the wearer's age, the wearer's foot pronation or running style (such as whether the user is a heel striker or toe striker), and the user's injury history.

1. A device for monitoring wear to a component of footgear having computer fabricated lattice structure therein based on the expected functional life of the component, as determined by a predetermined number of events, the device comprising: a sensor to detect events of the footgear due to activity of a wearer; a processor to count the events detected by the sensor and maintain a cumulative event total and to compare the cumulative event total to an event threshold, the event threshold calculated from the predetermined number of events, predicted lattice stress over time, and an individualized factor; and a display to indicate the relationship between the cumulative event total and the event threshold.

2. The device of claim 1 wherein the events are impact events.

3. The device of claim 2 wherein the sensor is an accelerometer responsive to motion.

4. The device of claim 1 wherein the events are stride events.

5. The device of claim 4 wherein the sensor is responsive to a flexible element.

6. The device of claim 5 wherein the flexible element is a piezoelectric sensor.

7. The device of claim 1 wherein the individualized factor includes at least one of the wearer's weight, the climate where the footgear is worn, and a type of predominate surface on which the footgear is worn, the wearer's age, the wearer's foot pronation, and the wearer's injury history.

8. The device of claim 1 further comprising a housing for the sensor, the processor, and the display.

9. The device of claim 1 wherein the footgear is a shoe and the component is a sole of the shoe.

10. The device of claim 1 wherein the display is integrated into a logo design on the footgear.

11. The device of claim 10 wherein the display changes color when the relationship reaches a specific value.

12. The device of claim 10 wherein the display includes a chemical indicator.

Population Based Health Analysis and Treatment

FIG. 1I shows an exemplary process to collect fitness data from shoes and predict patient with health issues and proactively assist patients. The process includes one or more of the following operations:

Establish patient registries and get permission for access to DBs (Apple Healthkit, Samsung SHealth, Microsoft HealthVault, . . . )

Collect health data covering all aspects of patient health: EMRs, provider DB, fitness wearable devices, pharmacy records, credit card purchase, phone purchases . . .

Monitor calorie burn, EKG, physical activity via footwear device

Determine risk information of an individual for example, one or more of: risk of the individual contracting a specific disease; a population risk that indicates whether the individual can benefit from clinical intervention; a level of priority for the risk score; a disease flag that indicates the type of disease for which the individual is at risk; a likelihood of hospitalization score that indicates the probability that the individual will require hospitalization; and, a numerical risk score indicating probability of illness Measure clinical and cost metrics Establish and adhere to complex clinical practice guidelines and send provider with clinical practice guidelines Perform disease risk-management outreach/Educate patients and engage with patients Track specific outcomes (success and failure) and find factors leading to success and vice versa The system includes a predictive modeling to compute risk information of an individual. The predictive modeling module may be adapted to compute or provide one or more of: a disease level that indicates the risk of the individual contracting a specific disease; a population risk score containing a numerical risk score that indicates whether the individual can benefit from clinical intervention; a level of priority for the risk score; a disease flag that indicates the type of disease for which the individual is at risk; a likelihood of hospitalization score that indicates the probability that the individual will require hospitalization; and, a numerical risk score indicating probability of illness based on analysis of pharmacy data of the individual.

The system also includes a predictive modeling module adapted to create a summary report comprising risk information of the individual. The predictive modeling module is adapted to format the risk information to comport with a note format of the workflow management module. To transmit the risk information to the note of the workflow management module, the predictive modeling module is disposed in communication with the workflow management module. The risk information may include one or more of a population risk score, a likelihood of hospitalization risk score, a pharmacy risk score, each of which may be transmitted to the note of the workflow management module by the predictive modeling module.

The present system also provides, in one of it aspects, a system for managing the health of a population comprising a predictive modeling module adapted to compute a risk level of an individual and adapted to generate a reminder when the risk level increases relative to a previously computed risk level. The system also includes a workflow management module disposed in communication with the predictive modeling module, where the workflow management module has an interface for receiving the reminder from the predictive modeling module.

In addition, the present system provides methods for managing the health of a population. In these aspects the present system provides a method for managing the health care of a population, comprising providing a workflow management module comprising an interface for receiving a health insurance claim; computing risk information of an individual; formatting the risk information to comport with the format of the health insurance claim; and providing the formatted risk information to the workflow management module in a claim field of the health insurance claim. Computing the risk information may include one or more of computing a disease level, computing a population risk score, computing a level of priority for the risk score, computing a likelihood of hospitalization score, and computing a pharmacy risk score. In another of its aspects, the present system provides a method comprising providing a workflow management module having an interface for receiving a note containing information about an individual; creating a summary report comprising risk information of the individual; formatting the risk information to comport with a note format of the workflow management module; and transmitting the risk information to the note of the workflow management module. Further, the present system provides a method comprising providing a workflow management module having an interface for receiving a reminder; computing a risk level of an individual; generating a reminder when the risk level increases relative to a previously computed risk level; and providing the reminder to the workflow management module.

Healthcare data refers to any healthcare or medical care data related or relevant to a patient. Healthcare data may include, but is not limited to, clinical data and healthcare-related financial data. Clinical data, as used herein, refers to any healthcare or medical data particular to a patient. In embodiments, clinical data can be medical care or healthcare data resulting from or associated with a health or medical service performed in association with a clinician in a healthcare environment (e.g., lab test, diagnostic test, clinical encounter, ecare, evisit, etc.). Clinical data may include, but is not limited to, a health history of a patient, a diagnosis, a clinician assessment, clinician narrative, a treatment, a family history (including family health history and/or family genetics), an immunization record, a medication, age, gender, date of birth, laboratory values, diagnostics, a test result, an allergy, a reaction, a procedure performed, a social history, an advanced directive, frequency and/or history of healthcare facility visits, current healthcare providers and/or current healthcare provider location, preferred pharmacy, prescription benefit management data, an alert, claims data, a vital, data traditionally captured at the point of care or during the care process, a combination thereof, and the like. In the same or alternative embodiments, the clinical data may include medical compliance information. In certain embodiments, medical compliance information refers to a level of compliance of a particular patient with one or more prescribed medical treatments, such as medications, diet, physical therapy, follow up healthcare visits, and the like. In one or more embodiments, the clinical data may include data obtained from the natural language processing of one or more clinical assessments and/or clinical narratives.

In certain embodiments, healthcare-related financial data can refer to any financial information relevant to a patient, such as insurance data, claims data, payer data, etc. Such healthcare data (e.g., clinical data and healthcare-related financial data) may be submitted by a patient, a care provider, a payer, etc. In certain embodiments where the healthcare data is being submitted by anyone other than the patient, the patient may be required to approve of such submission and/or may opt-in to or opt-out of having such healthcare data being submitted.

One embodiment uses local storage on the mobile phone of data collected by other devices and an an app is provided to interpret sensor data. The phones have fingerprint sensor security, and the mobile app is the point of aggregation for all the user's different health data. The health data is captured by the footwear and also by third party sensors (Nike+, Withings Scale, Fitbit Flex etc) and tie data from all fitness hardware into a cohesive whole.

In one embodiment, sensors in the device of FIG. 1B-1G can communicate with a mobile phone and transmit user activity or inactivity to networks that allow information access and provide support on the back end. Having a network or backbone that a much broader population base can seamlessly connect to will fuel more meaningful data comparisons and analysis and distill useful information. The network can then aggregate data from the footwear with other health information—data from across a certain geography or specific diagnosis, for example—to create a more complete picture of group health.

Creating healthcare communities from which to collect data is a way to crowd source valuable healthcare information. By bringing together people with a common interest such as weight loss, the footwear devices serve as a mechanism to build engagement and at the same time compile information. In one embodiment, the information is used by health payors or insurers to prompt patients to change their lifestyles. The more employers, insurance companies, or healthcare payors know about a population's health, the more steps they can take to keep them healthy. For instance, patient data entered into electronic health records at practices and hospitals could reveal allergies, health histories, and medication use. Combined with information collected through the footwear, providers will have more complete and essentially real-time data to treat and manage the health of individual patients, as well as patient populations. The cumulative sum of data captured from many individuals about a health condition or population can be used to move the population to healthier conditions. In one embodiment, health plans can offer incentives to members willing to sign up for designated footwear health programs and join in a "game" to be fit.

The system reduces healthcare costs by identifying trends and commonalities among certain populations—thereby enabling better preventive care. In addition to engaging patients and aiding personal wellness, they can move healthcare beyond individual monitoring and treatment toward more effective population health management.

By engaging and empowering patients to take an active role in data collection, the footwear applies inconspicuous foot data with analytics to improve health. One embodiment uses Google Maps to display health activity traffic; showing healthcare patterns based on real time reporting of anonymous data from healthcare footware devices. Healthcare organizations can tap the power of that data to engage patients and develop more effective and more personalized approaches to care, thereby lowering the overall cost of care.

The system identifies pre-detectable characteristics of a health condition, such that future incidents of the health condition may be predicted, i.e., before the health condition occurs for disease prevention. One implementation includes capturing data from mobile fitness devices and establishing a plurality of health related characteristics associated with the population including walking status, weight, calorie burn. The characteristics include a plurality of pre-detectable characteristics with a relationship between the health related characteristics and at least one health condition, and analyzing at least a portion of said population in response to the relationship.

Another embodiment includes establishing at least one pre-detectable characteristic associated with a health condition, applying an intervention in response to the characteristic, monitoring a success characteristic of the intervention, and determining a cause of the success characteristic.

Another embodiment builds a repository of health related characteristics associated with the population, the characteristics including a plurality of pre-detectable characteristics; and a processor configured to receive the health related characteristics, establish a relationship between the health related characteristics and at least one health condition, and analyzing at least a portion of the population in response to said relationship.

A population, as used herein, is any group of members. The population may include a high level of members, for example a group including one or more of the five kingdoms of living things, or a subgroup, for example a group including humans of a certain age range. The population may include living and/or dead members. The analysis may include predicting a likelihood of a member developing the health condition, in response to the relationship. The health condition may be any type of physical or mental health condition, disease, and/or ailment. In addition, the analysis may include predicting the incidence of the health condition. The analysis may also include performing a simple yes/no prediction regarding whether a member will likely develop the health condition. The analysis may be used to enable the management of a health care program, such as a program associated with a corporation, or a program offered to the public by a health care consultant or provider. If the analysis is associated with a corporation's healthcare program, the population may include some or all of the employees and retirees of the corporation, and associated spouses and dependents. The population may include other associated groups of the corporation, such as consultants, contractors, suppliers and/or dealers. The population may include participants from multiple corporations and/or the general public. If the health care program is offered to the public, the population may include members of the public, organizations, and/or corporations.

The health related characteristics may include a plurality of health characteristics, lifestyle characteristics and/or family health characteristics associated with the members of the population. Health characteristics may include characteristics indicative of a specific member's health. For example, lifestyle characteristic may include weight, heart rate, walking gait, sitting gait, running gait, exercise or activity as detected by accelerometers, diet, and other factors detectable by fitness devices such as watches, phones, or foot sensors detailed above. For other example, health characteristic may include medical characteristics (e.g., what medical visits, processes, procedures, or test have been performed associated with the member, the number of days the member has spent in a medical facility (e.g., a hospital), the number of visits the person has made to a doctor, etc.), drug characteristics (e.g., what type and amount of drugs are being consumed), a death characteristic (e.g., information associated with a death certificate), an absenteeism characteristic, disability characteristics, characteristics associated with existing health conditions, etc. Family health characteristics associated with the member may include information associated with the family medical history of a specific member. For example, a history of a particular health risk within the family, e.g., heart failure, cancer, high blood pressure, diabetes, anxiety, stress, etc. Lifestyle characteristic may include a specific member's behavior characteristic(s), of which some or all may be modifiable lifestyle characteristics. A modifiable lifestyle characteristic may include an exercise characteristic (e.g., does the member exercise, how often, what is the exercise, etc.) and/or a nutrition characteristic (e.g., what types of food does the member eat, and how often). Nutrition characteristics may also include the amount of salt consumed during a designated period (e.g., a day), and the amount of fat and/or saturated fat consumed during a designated period. In addition, modifiable lifestyle characteristics may include whether the member drinks alcohol (and if so how much), a drug intake characteristic, (i.e., does the member take drugs, and if so how often, what kind, and how much), a weight characteristic (e.g., what does the member weigh, what is the member's desired weight, is the member on a diet, what is the member's weight indicator e.g., obese, slightly overweight, underweight, normal, etc.), a smoking characteristic (does the member smoke and if so how much), a safety characteristic (what are the member's driving characteristics e.g., does the member where seat belts, have one or more infractions associated with driving under the influence, or speeding tickets, etc.). In addition, modifiable lifestyle characteristics may include a hypertension characteristic, a stress characteristic, a self-care characteristic, a self-efficacy characteristic, a readiness to change characteristics, and a prophylactic aspirin therapy characteristic.

In one embodiment, the health related characteristics may also include one or more of the following: demographic characteristics, the member's location or geography, age, gender, employment status, employment type, and/or work characteristics of the member. The health-related characteristics may be obtained through one or more of several sources, such as medical claims, drug claims, and/or self-reported characteristics (or data). In one embodiment, self-reported characteristics may be collected from the population. The amount and type of self-reported characteristics collected associated with the population is implementation dependent and may vary based upon the participation of the population, the relevance of the information to the different members of the population, and the analysis to be performed. Therefore the self-reported characteristics established may be associated with a subset, or portion, of the established population, or the entire population. The self-reported characteristics may include one or more health characteristics, family health characteristics, and lifestyle characteristics associated with a member of the population. The self-reported characteristics, also referred to as self-assessments, may be obtained through the use of one or more health related questionnaires submitted to the member. Examples of questionnaires include physical questionnaires, electronic questionnaires (e.g., located on a health related web-site), questionnaires filled out during a phone or personal interview, etc. The responses to the questionnaires may include a member's self assessed health related characteristics. The characteristics may include a self-efficacy characteristic and/or a readiness to change characteristic. A readiness to change characteristic is a characteristic indicative of a members readiness to change one or more behaviors, activities, or characteristics. A self-efficacy characteristic, as will be discussed, includes an indication of a member's belief in their ability to succeed in changing a lifestyle characteristic. For example the self-assessment questionnaire may specifically ask the member: does the member believe they can change their lifestyle or a specific aspect of their lifestyle, is the member willing to attempt to change an aspect of their lifestyle and if so, how successful do they think they will be, how important do they think it is to change one or more specified lifestyles, etc. Alternatively, one or more questions may be asked of which the answers may provide indirect indicators of whether the person actually does believe they can change aspects of their lifestyle, and also whether the member is actually ready to change a particular aspect of their lifestyle.

In one embodiment, the health related characteristics of the population are associated with self-reported biometric characteristics. For example, the sources of the health related characteristics may be self-reported biometric sources. That is, the sources of the health related characteristics are sources other than the direct physical examination of a member (e.g., where members provide a biological sample etc). The distinction is based on the issue that due to the size of the population, it may not be possible to analyze all of the members by having detailed examinations (e.g., blood samples, urine samples, etc.) of all, or even a substantial portion of the population. Therefore, in one embodiment, the health analysis is based on information that is obtained second-hand, without having physically examined a specific member to directly obtain the desired health related characteristics. Of course, if the described analysis indicates a particular member needs to be physically examined based on likelihood of occurrence of a health condition, that examination may occur. In one embodiment, the health related characteristics may related to non-intrusive characteristics, i.e., characteristics that do not directly involve the physical examination or taking of biological samples of a member by a physician. For example, a blood sample may be considered intrusive data because it involves the taking of a sample from a member.

The collected health related characteristics may be stored in a repository. The duration of storage is implementation dependent, but in general the more information available for analysis, the more accurate the results will be. Therefore, a historical repository of five to ten years may be established. In some embodiments, characteristics may be available throughout the working career of the members, e.g., if their employer collects self-reported information, medical and/or drug claims. The historical repository aids analysis in several ways, including reducing the impact of recall bias. Recall bias is what may happen when a member acquires a particular health condition, and then attempts to recall what factors may have contributed to the condition. The members recollection may be biased by any number of issues including their ability to accurately remember all the desired information. Therefore a historical repository aids in providing accurate information for analysis.

The established health related characteristics may be used to analyze the health of the population. In one embodiment, as illustrated in a second control block 104, a prevalence of a health condition within the population may be established. The prevalence of a condition may be described as the current existence of a condition. The prevalence of a health condition among a population may be described as the number or percentage of members that have a specific health condition. Establishing the prevalence of a condition in a population may include determining which members currently have a specific health condition. The prevalence of a health condition may be established by analyzing the health related characteristics associated with one or more members of the population and responsively establishing whether one or more members has the condition. For example, the prevalence may be established by analyzing information associated with medical claims and/or drug claims associated with the population.

Medical claims may include any type of health related correspondence between a health analyst or provider (e.g., doctor, physician, medical laboratory, hospital, medical support group such as x-ray providers, etc.), and a member of the population and/or a health care insurer, provider, or manager, for the member (e.g., corporation (employer) or third party insurer/manager, etc.). In one embodiment, the healthrelated correspondence may include health codes such as E/M (Evaluation and Management) codes, Current Procedural Terminology (CPT) codes, and International Classification of Diseases (ICD) codes. ICD codes provide coded information associated with the treatment, health, and/or a condition of a member. These codes may include information associated with the professional services performed, the specific procedure(s) performed, and why the procedure(s) was performed. Therefore, analysis of ICD, CPT, and/or E/M codes may be used to establish whether a member has a particular health condition.

A drug claim may include any type of medication related correspondence between a medication provider (e.g., doctor, pharmacist, etc.), and a member of the population and/or a health care insurer, provider, or manager for the member (e.g., corporation (employer) or third party insurer/manager, etc.). In one embodiment, the correspondence may include codes or identification systems such as Group Product Index (GPI). The GPI provides a numbering system associated with the medication a member receives, and/or medication prescribed for a member. The GPI enables the identification of the type of drug, manufacturer, strength, associated dosage, and associated medication form (e.g., pill, tablet, liquid, etc.).

In one embodiment, information associated with at least one medical and/or drug claim may be used to determine the prevalence of a condition, e.g., whether a member has one or more specific health conditions. For example, if a medical claim indicates a particular procedure has been performed, then that procedure may be correlated to one or more potential health conditions associated with that procedure. Analogously, if a drug claim indicates that a member is being prescribed and/or receiving a particular medication, then that medication may be correlated to one or more potential health conditions associated with that medication. In this manner, the information associated with the medical and/or drug claims may be analyzed to establish a prevalence of a condition. The analysis may be performed on each member of the population, or a subset thereof.

In one embodiment, information associated with multiple medical and/or drug claims may be analyzed based on established criteria, to establish the prevalence of a health condition. For example, multiple medical and/or drug claims may be cross checked with each other to establish the prevalence of a health condition. An individual medical or drug claim may contain erroneous or misleading information. For example, there may be instances where a medical procedure is performed to test for a health condition, without definitively establishing the condition exists in the member. Analysis of the resulting medical claim may lead someone to erroneously believe the person had the healthcondition (e.g., based on the types of procedures being performed). Therefore, using one medical or drug claim may not provide an accurate indication of the presence of a health condition. Additional medical claims and/or drug claims may be analyzed to establish one or more healthrelated characteristics of a member, such as the prevalence of a health condition. In one embodiment, multiple medical and/or drug claims, separated by a time period (e.g., a minimum duration) may be analyzed. The separation in time increases the confidence level regarding the determination that a particular health claim, or health related characteristic, exists. For example, two claims of the same type (e.g., two medical claims or two drug claims), separated in time by at least three months, may be analyzed to determine if a member has a health condition.

If the first claim indicates a condition exists, and a second claim indicates the same condition exists, then the member may be assumed to have the condition associated with the medical claims. The two claims may sequentially occur, or be separated by one or more other medical and/or drug claims. In addition, a claim of one type (e.g., medical claim) may be cross checked with a claim of another type (e.g., drug claim). If the two claims correlate, then the member may be considered to have the particular condition. The two different types of claims may also be separated by a designated time period, e.g., three months, to further establish that the condition actually exists. In one embodiment, the time separation is established such that the two claims represent independent indicators, as opposed to two claims associated with the same medical event (medical checkup or medication collection). Additional criteria may include that the claims being correlated should occur within a particular time period of each other. For example, if two claims indicating a particular health condition are separated by five years in time, there is a chance that the claims were inaccurate anomalies as opposed to indications of the existence of the health condition. Therefore, a maximum duration between claims being cross checked may be established (e.g., one year). In one embodiment, the maximum duration between cross checked claims may be dependent upon the condition at issue. For example, some health conditions may be more likely to have multiple claims occur within a specific time duration. While other health conditions may not manifest themselves in multiple medical claims in that same specified time duration. Therefore, the duration between claims may be implementation and health condition dependent.

When claims are received, they may be manually or automatically analyzed. For example, when a claim is received, it may be analyzed to establish associated health characteristics. The health characteristics may then be cross checked with information from other claims in an attempt to verify one or more of the health characteristics. The analysis may include correlating the claim with a table of potential health characteristics associated with claim information. The information may be compared with previous claim information to determine if prior claims indicated the same, or similar health related characteristics. If the cross check indicates one or more prior claims indicated the same health related characteristic, then the member may be assumed to have the health related characteristic (e.g., the health condition). If no prior claim information correlates with the current claim information, then the current claim information, and the correlated health related characteristics may be store to be compared with future claims that are to be receive. In one embodiment, if a strong correlation exists between the health related characteristics associated with multiple claims, and a sufficient time period exists between the claims, then the member may be determined to have the characteristics. Alternatively, machine learning such as classical, Bayesian, and/or statistical analysis techniques may be used to correlate and cross check one or more medical and/or drug claims with one or more health related characteristics and/or health conditions. For example, neural networks may be trained to associate information associated with medical and/or drug claims with particular health related characteristics and/or health condition. Then when a claim is received, it may be analyzed to establish potential health related characteristics and/or health conditions. The neural network may be able to provide a weighted analysis such that the results have an associated confidence factor. If multiple claims separated in time indicate the same or similar health related characteristics, the resulting neural network analysis may provide a higher confidence indicator than if just one claim indicated the characteristics. Therefore, as prevalent health conditions are established based on medical and/or drug claims, the claims may be further analyzed to establish a relationship capable of automatically detecting a prevalence based on the available medical and/or drug claims.

In one embodiment, the medical and/or drug claims may be analyzed as they are received. Alternatively, there may be a repository of one or more previous medical and/or drug claims associated with the member(s). For example, repositories may be created that include a members historical health related characteristics over a time period (e.g., the last five-ten years). These repositories may be maintained by the health care provider, insurer, analyzer, and/or manager. These repositories may be analyzed to establish a prevalence of a condition among the population.

In one embodiment, self-reported characteristics may be analyzed to establish the prevalence of a condition, e.g., among one or more members of a population and/or the population as a whole. For example, a member may specifically indicate that they have a particular condition such as high blood pressure, diabetes, smoking, overweight, among others. Alternatively the analysis of one or more of the family history, lifestyle, or health characteristics indicated through the self assessments may indicate that the member likely has a particular condition. In this case additional follow-up may be performed with the member to determine if they actually have the condition, or know that they have the condition. In one embodiment, a relationship may be established to determine the existence of a condition among a particular member and/or among the population.

In one embodiment, medical claims, drug claims, and self-reported characteristics may be used to establish the prevalence of a particular condition among the population. Alternatively, as indicated above, the prevalence of a condition may be established based on one or more of the sources of information (e.g., medical claims, drug claims, and/or self-reported characteristics). The prevalence may be established manually or through an automated process such as the use of statistical analysis techniques as mentioned above. The decision of what information (or sources of information) to use may be based on what information is available for the population, or for a particular portion of the population. For example, some portions of the population may not have a historical data base of information available for analysis. In addition, some portions of the population may not have associated medical claims, drug claims and/or self-reported characteristics. Therefore the type and amount of information to be analyzed to establish the prevalence of a disease is implementation dependent and may be based in part on the type of information available for a particular population, or portion thereof.

A relationship may be established between the health related characteristics and one or more health conditions. In one embodiment, the relationship is established in response to the prevalence of the health condition. The relationship may then be modified based on future occurrences, or rates of occurrences of the condition. Alternatively, the relationship may be established by analyzing future occurrences or rates of occurrence of the condition without accounting for an initial prevalence of the condition. In one embodiment, as described below, the relationship may be used to predict an incident or occurrence of a disease, e.g., an occurrence of a disease among a particular member or among a population in general. Information gained from establishing the prevalence of the condition may be used to establish the relationship. For example, the health related characteristics associated with the members determined to have a particular condition may be analyzed to establish a relationship associated with a likelihood of developing the condition. In one embodiment, the predictive relationship is different than the analysis to determine the prevalence of a condition because the prevalence analysis may be used to establish who has the condition. However, the occurrence predictor may be used to establish the health related characteristics that are needed to predict the likelihood of developing the health condition. In one embodiment, all of the health related information associated with a member having a condition, or all of the health related information believed to be potentially relevant to a health condition that a member has, may be analyzed to establish the relationship. The health related information to be analyzed may be historical data that pre-dates the incidence of the health condition.

The analysis and associated relationship may indicate the pre-detectable characteristics associated with a health condition. Pre-detectable characteristics are characteristics that impact the chance of acquiring risk factors associated with a condition. A pre-detectable characteristic may be associated with more than one risk factor and/or more than one health condition. A heart attack is an example of a health condition. Risk factors associated with a heart attack may include obesity, age, and gender. A risk factor may be described as one form of a heath related characteristic that is a known, believed, or hypothesized to be an indicator of acquiring a health condition, or increasing the risk of acquiring the health condition. Risk factors usually have one or more pre-detectable characteristics associated with them. Pre-detectable characteristics associated with obesity, or being overweight, include dietary characteristics, such as the amount of saturated fat, fiber, and calories consumed during a time period. By reducing the amount of saturated fat consumed (a pre-detectable characteristic), the chances of acquiring the associated risk factor may be reduced (e.g., reduced chance of being overweight). If the chances of acquiring a risk factor is reduced or eliminated, then the chances of acquiring an associated health condition (e.g., the heart attack) are also reduced or possibly eliminated. As will be discussed, one embodiment of the present disclosure is associated with identifying pre-detectable characteristics associated with a health condition, and then predicting an incident of the condition associated with a particular member based on the particular health related characteristics associated with that member. Intervention recommendations may then be tailored to the particular pre-detectable characteristics exhibited by the particular member. In one embodiment, the collected health related characteristics may be detailed and extensive in order to acquire the desired information that may be associated with possible pre-detectable characteristics. By the nature of the analysis being performed, the pre-detectable characteristics may not be initially known. Therefore, monitoring of future occurrences of the condition, and analysis of the associated health-related characteristics enables the predictive relationship to evolve as new information is available.

The details of the establishment of the relationship will be described below. However, in general, the health related information associated with the population will be analyzed to establish the relationship. The analysis may include the use of statistical analysis techniques such as classical, Bayesian, and/or machine learning analysis techniques to analyze the health related information. For example, neural networks may be trained using all the health related characteristics of the members having a particular condition.

Then, the health-related characteristics of a member of the population may be delivered to the neural network for analysis. The resulting analysis may provide a weighted answer indicative of the likelihood the person will acquire the condition. In addition, review of the neural network may provide insight into which health characteristics are more relevant to acquiring the condition. These characteristics may then be reviewed to establish the pre-detectable characteristics associated with the condition. For example, the relevant health related characteristic may be a pre-detectable characteristic, or may have associated pre-detectable characteristics. Therefore, depending on the specific implementation used, the analysis may be able to indicate the health related characteristics that are most relevant to the prediction of a particular health condition.

The relationship may be used to analyze the population with respect to the health condition. For example, the relationship may be used to predict the likelihood of developing a condition associated with the population, or a portion thereof. As such, the relationship may be used to predict a future incident or occurrence of the health condition. In one embodiment, the health related information associated with one of the members of the population may be analyzed using the established relationship. The analysis may indicate, or predict, whether the member will develop a particular disease, which may include the likelihood the member will develop the particular disease. The analysis may be used to predict the occurrence of the disease based upon the established pre-detectable characteristics. In addition, this analysis, or information resulting from the analysis may be used to predict an incidence of the health condition, e.g., over a specified period of time, how many members will develop the disease, or what is the likelihood of a particular portion of the population developing the disease over a specified time period.

In one embodiment, depending on the health condition associated with the analysis, the analysis may also establish a predicted time period in which the incident may occur (e.g, the next year, next five years, next ten years, etc.). In addition, the analysis may establish a stage of the condition associated with a particular member. For example, some conditions may have definable stages of the onset of the disease.

In one embodiment, a likelihood of developing the condition may be established based upon the analysis. For example, some analytic techniques produce information associated with the likelihood of having the incidence, e.g, a confidence level. Therefore, the analysis may include classifying all or a portion of the population with respect to one or more conditions, based on the likelihood of the particular members having an incidence of the disease, based on the particular stages of the condition the population members fall within, and/or based on the predicted time period associated with the incidence. In this manner the population may be classified, or ranked, with respect to the likelihood of developing a condition, the time period in which the development may occur, and/or the stage of the condition the member is in. As described below, this classification, or ranking of the population, or a portion thereof, with respect to one or more conditions enables, specific interventions to be applied to specific members based on predicted risk, and also enables the management of the population as a whole, and the intervention and associated cost, etc. Therefore, the population may be analyzed to establish a likelihood of developing of one or more conditions, among one or more members of the population.

An intervention may be recommended in response to the likelihood of developing the health condition. Factors that may be used to select the appropriate intervention include the predicted likelihood the member will develop the health condition and the pre-detectable characteristics the member exhibits that are associated with the condition. For example, the more likely the person is to acquire a particular condition, the more aggressive the intervention recommendation may be. Other health related characteristics may also be used to determine the appropriate intervention, such as the self-efficacy characteristic and/or readiness to change characteristic associated with the member, and the likelihood of success of the intervention. The cost of the intervention may also be a factor in intervention selection. The role of intervention cost may be based on the premise that there is a finite amount of money available to administer health care interventions to the population. Therefore, one use of the analysis may be to determine how the interventions may be applied in a cost effective manner, while providing the best benefit for the population. For example, given the choice between recommending an intervention that is 60% effective and an intervention that cost twice as much, but is only 62% effective, the decision may be to apply the less expensive, yet effective intervention, and use the "savings" in other areas of the health care program.

One implementation may include the step of establishing a success characteristic associated with the intervention. The success characteristic may include a characteristic associated with the success of the intervention, e.g., did the intervention succeed (or assist in succeeding) the prevention or delay of the incidence of the health condition. The success characteristic may include characteristics associated with whether the intervention was used, to what degree the intervention was used, why the intervention was, or was not used, and how effective was the intervention in light of how much it was used. Some of these success characteristics may be established shortly after recommending the intervention (e.g., was the intervention used and why or why not, to what degree the intervention was used, if not used what would it take to motivate the member to use, etc.), while other success characteristics may not be established for a period of time (e.g., if used, how successful was the intervention).

Success characteristics may be collected in several ways. Fitness sensors on the phone, watch, or foot can detect changes leading to/from success and provide appropriate warnings to the user or an assigned health coach. The characteristics may also be collected through medical and/or drug related information. For example, an intervention may include a recommendation that the member visit a medical provider (e.g., doctor), have a medical test performed, and/or be prescribed a particular drug. The members medical and/or drug claims may be monitored to determine if the recommendation was followed. For example, if over a particular time period, e.g., three months, there is no indication from reviewing medical claims, that the member visited a medical provider, then the assumption may be made that the member did not follow the recommendation. In light of this, a health care counselor or provider may be notified, and the member contacted to verify they did not follow the recommendation, and determine why the recommendation was not followed (if indeed it wasn't). This may be done by monitoring claims either manually or in an automated fashion, e.g., through the use of a computer program. For example, once an intervention is recommended, a computer related program may be configured to automatically review medical, drug claims, and/or self assessment characteristics to monitor characteristics of whether the recommended intervention was performed. In addition to fitness device reporting or through claims reporting, the success characteristics may be collected through self-reported data (e.g., targeted questionnaires, interviews, one on one phone calls such as counseling phone calls, etc.). For example, if a particular intervention recommended a medical visit, the targeted questionnaire or counseling call may specifically inquire as to whether the medical visit was made, and why or why wasn't the visit made.

In one example, the success characteristics, may include information indicative of a persons self-efficacy, and/or readiness to change. For example, if the established predictive relationship indicates that a particular member is at risk for a heart attack, and part of the pre-detectable characteristics associated with a heart attack is that the member is eating too much saturated fat, an intervention recommendation may include recommending a change in lifestyle, e.g., increased exercise such as running, walking, or swimming. The success characteristics may indicate that the person did not engage in any exercise (e.g., on a subsequent self assessment). Upon further follow up (e.g., within the same questionnaire or counseling session, or in a later one), the member may indicate that they don't enjoy exercising and/or they don't perceive the need to do so. Alternatively, the member may indicate that they tried running, but their knees hurt, so they stopped, and/or they did not have access to a swimming pool. That is, while they are willing to engage in a recommended intervention, the specific intervention recommended did not work for them. Alternatively, the member may indicate that while they enjoy working out, they do not have time outside of their work and family activities to engage in the recommended intervention. The measured characteristics may also indicate that the recommended intervention was followed. In this case, information may be obtained regarding why the recommendation was followed.

The success characteristics may be used in several ways. In one embodiment, analysis may be performed with the success characteristics to establish a relationship capable of indicating or predicting a members engagement of an intervention, or willingness to engage in a particular intervention, or in any intervention. For example, the health related information, including the success characteristics, associated with members who have been recommended a particular intervention, may be analyzed. The analysis may result in a relationship that is able to establish the likelihood a particular member will follow a particular recommendation, based upon the specific health related information associated with the member. In one embodiment, the success characteristics may be used to establish a relationship capable of indicating or predicting a particular member's engagement of any recommendation, or willingness to engage in any intervention. In one embodiment, the analysis may include establishing a relationship capable of predicting a member's readiness to change stage. That is, in one embodiment, readiness to change categories may include a pre-contemplation, preparation, and action stages. If a member is in a pre-contemplation stage, they may not be willing to engage in any intervention. In the preparation stage, a member may be willing to pursue a particular intervention, but not just any intervention, or they may be willing to pursue interventions, but have not started. In the action stage, the member may be ready to take action in the appropriate intervention. By classifying a member into a readiness to change category, interventions may be further tailored for the individual member. For example, if a member is in the pre-contemplation stage, then the selected intervention may include additional counseling and/or educational literature associated with the seriousness of the potential condition, and the risk associated with this particular member of acquiring the condition if no action is taken. In addition, the intervention associated with the preparation category may include customizing the proposed intervention to the interventions the member is more likely to pursue. In this manner, self-efficacy and readiness to change characteristics associated with a particular intervention, may be analyzed with other self-efficacy and readiness to change characteristics associated with other interventions, and applied to the population as a whole where appropriate. That is, some established self-efficacy and readiness to change characteristics may be generalized (e.g., by creating a predictive relationship) and applied to the whole population to predict a particular members likelihood to engage in a particular intervention, or an any intervention. The analysis may include using statistical analysis (e.g., neural networks, regression analysis, etc.) to establish a relationship that is able to predict a members willingness or ability to pursue a particular intervention. In this manner a relationship may be developed and used in future instances such that when a member is predicted to have an incidence of a condition, the recommended intervention may be based upon indirect indicators of a members self-efficacy or readiness to change, as well as direct indicators (e.g., specific questions such as: are you willing to reduce your smoking).

For example, potential interventions may include an exercise regimen, a dietary regimen or a medication, to reduce the risk of a condition. The exercise regimen may indicate the highest success rate if followed, the medication the lowest success rate if followed. In addition, the member may provide strong direct indications of self-efficacy and readiness to change characteristics. However, the established participation predictive relationship may indicate that members with similar health characteristics (e.g., job requiring long hours, area of the country not conducive to exercise during the winter, and number of dependents in the family), that the member is not likely to follow through on an exercise regimen (e.g., due to time constraints from the job and family and inclimate weather). However, based on the other members, it may be predicted that this member is most likely to follow through a dietary change. Therefore, the intervention may be targeted to either changing the dietary habits of the individual.

In addition, the analysis of the success characteristics and associated health related characteristics may include establishing a relationship able to indicate a potential success of a particular intervention. For example, the success of an intervention may be established by monitoring/analyzing the health related information for an extended period of time. The health related information, including characteristics indicative of the incidence of the health condition may be monitored after the intervention is applied, and compared to health related characteristics expected if the intervention had not been applied (e.g., whether an incidence of the health condition would occur, when it would occur, when the stages of the incidence (if any) would occur. In addition, the health related characteristics may be analyzed to determine if any immediate changes in health care characteristics occurred. For example, if the health condition is a heart attack, and one of the pre-detectable characteristics associated with heart attacks is a members consumption of high saturated fats, then one intervention recommendation may be a dietary program. The health care characteristics may be monitored to determine if the dietary program was successful in reducing the members saturated fat consumption, and/or whether the dietary program was successful in eliminating or delaying the incidence of the health condition. Therefore the success of the intervention may be monitored with respect to eliminating or delaying the health condition, and/or eliminating or reducing a cause associated with the health condition. The results of the intervention monitoring and associated health related characteristics may be used to further refine the decision process regarding which intervention to recommend.

The health related characteristics, including the success characteristics, may be used to select one or more interventions for a particular member at risk of a particular condition. In addition, the health related characteristics may be used to establish a relationship that associates one or more interventions with particular health related characteristics and a health condition. The success characteristics may indicate that interventions have varying degrees of success based upon the health related characteristics such as the physical characteristics of the individual engaged in the intervention, the thoroughness of the use of the intervention, the willingness of the person to pursue, etc. For example, assume there are two potential interventions for a health condition. Assume intervention 1, if followed 100%, is 90% effective, and if followed 50% is 30% effective. In addition, assume intervention 2, if followed 100% is 60% effective, and if followed 50% is 45% effective. Depending on the health related characteristics of a particular member, the best chance of preventing or delaying the condition (or eliminating a cause of the condition) may lie with pursuing intervention 2. For example, if the self-efficacy characteristic, or readiness to change characteristic is low, this may be an indication that the member won't follow through completely with the recommendation. Therefore, the second intervention may be pursued that may have a better impact than the first intervention given that neither intervention is used completely. Therefore, a relationship may be developed that is able to predict the effectiveness of a particular intervention in general, e.g., if the intervention is used X %, then it will be Y % effective. This information may be used to make an intervention recommendation to a member or, to engage in further correspondence (interviews, follow-up questionnaires, etc.) with the member. For example, the member may be notified of the preferred intervention, but of the concerns that they are not going to fully engage the intervention. If they don't fully engage the intervention then there is an alternative intervention that is preferred. In addition, a relationship may be established to predict the usage of an intervention by a particular member, based upon the health related characteristics of the member. The relationship may also be able to predict the success of a particular intervention based on the predicted use of a member (e.g., based on the members self-efficacy, readiness to change, and or other health related characteristics). In addition, interventions may have varying success among different members, even if pursued to the same degree. Therefore, the recommendations may be modified based on any previous engagement by the member in an activity related to an intervention. For example, health related characteristics associated with the member and the activity the member engaged in may be used to tailor the specific recommendation provided.

In one embodiment, the success characteristics associated with a particular member may be used to further refine, or establish, a recommended intervention for the member. In addition, the success characteristics may be used to refine the analysis (e.g., relationship) that correlates a member of a population with a particular intervention, based on the health related characteristics of the member.

A relationship is established between the health related characteristics and a health condition. The type of analysis used to establish the relationship is implementation dependant and may vary as a function of the data available information being requested (e.g., explain the similarities/dissimilarities of the health related characteristics of members having the condition, predict future incidences, or both). The analysis may be dependent on the number of dependent variables (e.g., the health condition(s) associated with data) and/or independent variables (e.g., health related characteristics) that are being analyzed in the relationship and/or the objective of the analysis being performed. For example, the analysis may include the use of statistical analysis techniques such as classical, Bayesian, and/or machine learning techniques. Classical analysis techniques may include multivariate statistical techniques simple regression, multiple regression, factor analysis, item analysis multivariate analysis of variance, discriminant analysis, path analysis, cluster analysis, multidimensional scaling, rule induction, and/or least squares estimation. In one embodiment, multiple regression may be used to determine the relationship between one dependent variable (e.g., whether a person has diabetes) and multiple independent variables (i.e., multiple other health related characteristics, such as weight, gender, age, dietary habits, walking/running/exercise, etc.). Other techniques, such as in factor analysis, cluster analysis, and multivariate techniques may be used when the desired relationship is associated with multiple dependent variables and multiple independent variables. Generic model-fitting or classification algorithms e.g., neural networks (e.g., back propagation, feed-forward networks, etc.), meta-learning techniques such as boost, etc., may be applied for predictive data mining. Predictive data mining techniques may be desired when the accuracy of a prediction is of higher priority, regardless of whether or not the models or techniques used to generate the prediction is interpretable or open to simple explanation. That is, data mining techniques may be desired when the objective is to predict the future occurrence of a health condition, as opposed to analyze the existing relationship among the health related characteristics that leads to the health condition. As mentioned, the selection of the particular analysis technique(s) is implementation dependent and may be based on factors such as user preference, the data to analyze, and the number of dependent and/or independent variables, the objectives of the analysis. Therefore, in one embodiment of the present disclosure, the person analyzing the health of the population may specify the analysis techniques to be used, or the analysis system may automatically determine the appropriate technique(s) to use.

In one embodiment, data analysis using deep neural network techniques may be used to establish a predictive relationship between the health related characteristics and one or more health conditions. For example, the health related characteristics associated with members known to have a particular health condition, may be used to "train" the neural network. There are several types of neural network models. The selection of which model or combination to use may be implementation dependent, and implementation accuracy may vary based on model used, data analyzed, and desired objective of the model. In one embodiment, the model used is a back propagation network. The back propagation network may receive the health related characteristics associated with the members known to have a particular health condition, along with the characteristics of members known not to have the characteristic. The resulting "trained" neural network may then be able to receive the health related characteristics of a member to predict whether they will acquire the health condition. In one embodiment, the neural network output is a number (e.g., between zero and one), that may be used to indicate that the member has a determined likelihood of having an incidence of the condition (e.g., 75%), if they do not already have it. As was discussed above, the resulting likelihood of occurrence may be used to rank the population in terms of likelihood of acquiring the condition. This ranking may then be used to prioritize intervention strategies.

In addition to establishing a likelihood of occurrence of the health condition, the internal organization of the neural network may be analyzed to determine which health related characteristics where most relevant to the condition. For example, a back propagation network includes multiple weighted interconnections between the input factors and the output. The weighted interconnections may be reviewed and correlated with the input health related characteristics. In this manner, the characteristics having more relevance (e.g., a higher weighting value) may be identified. These relevant characteristics may then be reviewed to establish the pre-detectable characteristics of associated with the health condition. For example, the established health related characteristics may already be pre-detectable characteristics (e.g., the amount of salt consumed per day, the amount of saturated fat consumed per day). However, if the established health related characteristics are not pre-detectable characteristics, then further analysis may be performed to break the characteristics into the pre-detectable characteristics. For example, if being overweight is established as a relevant health related characteristic, then further analysis may be performed to determine what pre-detectable characteristics lead to being overweight, and which of these pre-detectable characteristics did members being analyzed exhibit. In one embodiment, all of the factors associated with being overweight may be treated as being relevant. Alternatively, the potential pre-detectable characteristics are used to further refine the relationship to establish which of the pre-detectable characteristics plays a role in being overweight, when overweight is a factor in having a particular health condition, e.g., diabetes.

In one embodiment, if multiple regression is the analysis technique used, an equation associated with the relationship may be: $Y = b1X1 + b2 \times 2 + \ldots bnXn + c$, where the b's are the regression coefficients, representing the amount the dependent variable Y (e.g., likelihood of contracting a health condition) changes when the independent variable (the X's, e.g., the health related characteristics) change 1 unit. The c is the constant, where the regression line intercepts the y axis, representing the amount the dependent variable Y will be when all the independent variables are 0. In one embodiment, a determination may be made regarding whether any transformation (e.g., log functions, square roots, etc.) are needed to the proposed relationship (or equation). For example, should the log of a health related characteristic be used in the relationship, should the square root of a health related characteristic be used in the relationship, etc. As will be discussed, the form of the equation, e.g., whether one or more transformations are used, may be determined by the user, by the analysis system, or a combination thereof.

In one embodiment, different relationships may be created, e.g., using different transformations or different health related characteristics for the multiple regression analysis, and analyzed to determine which relationships perform better than others. Goodness of Fit analysis techniques such as R2, RMS, P Value, F ratios, standard error, etc., may be used to establish performance characteristics of the relationships. For example, techniques such as R2, which establish the percent of variance in the dependent variable (e.g., the part characteristic cost), explained collectively by the independent variables (e.g. the other part characteristics). By using R2, for example, an assessment may be made regarding which relationship best explains the variance in the dependent variable in response to the independent variables. RMS provides an indication of which model best predicts future aspects of a part, or part to be designed.

In one embodiment, a threshold level of desired performance may be established for the relationship. If the relationship does not meet the threshold level of desired performance, then the user may be notified that the established relationship does not meet the desired level of accuracy, the desired level of ability to explain the variance in the dependent variable in response to the independent variables, or desired level of ability to predict future characteristics of the part. If multiple relationships are being compared with each other, and none of them exceed the desired level of success, then the user may be notified of which relationship performed best, but that none of them met the desired threshold. If multiple relationships are tested and one or more exceed the threshold, the best one may be selected, or they may all be provided to the user for selection.

One method for performing population health management includes establishing a plurality of health related characteristics associated with the population; establishing a relationship between the health related characteristics and at least one health condition; and analyzing at least a portion of said population in response to said relationship. The system can predict a likelihood of at least one of said members developing said at least one health condition, in response to said relationship and/or the members health related characteristics. The system can determine a prevalence of a health condition within said population in response to said health related characteristics. The plurality of health related characteristics associated with said population can be done by establishing a plurality of self-reported characteristics associated with at least a portion of said population. A prevalence of the health condition can be determined by: establishing a plurality of claims associated with at least one os said members, said claims including at least one of a drug claim and a medical claim; cross checking said plurality of claims (such as over a period of time, or over a number of tests); and establishing said prevalence in response to said cross checked claims. The system includes predicting a member's likelihood of developing a condition with a stage of said condition in response to said prediction. The system can predict a time period associated with said development. The system can classify said population in response to said prediction, and then prioritize treatment of the population in response to said prediction.

The system can recommend an intervention in response to said predicted likelihood of development. This can be done by establishing a plurality of intervention recommendations associated with said condition; establishing a success characteristics of said recommended intervention; establishing at least one of a readiness to change characteristic and a self-efficacy characteristic of said member; and recommending said intervention in response to said plurality of intervention recommendations, associated intervention success characteristics, and member health related characteristics, said health characteristics including said self-efficacy and said readiness to change characteristic.

The system can monitor failure/successful characteristic of said intervention, and determining causes resulting in said success characteristic. The system can capture a plurality of self-reported data associated with at least a portion of said population having said condition. The self-reported data includes at least one of a lifestyle characteristic, a family history characteristic, and a health characteristic. The predictive relationship can be done by establishing at least one objective of said relationship; dynamically selecting a statistical analysis technique in response to said objective; and establishing said relationship in response to said statistical analysis technique. The predictive relationship can be applied to at least a portion of said population; and predicting a likelihood of developing said condition in response to said application.

The system can be configured to analyze the health of a population having multiple members. In one embodiment, the method includes the steps of establishing a plurality of health related characteristics associated with the population, the characteristics including a plurality of pre-detectable characteristics, establishing a relationship between the health related characteristics and the health condition, and predicting an incident of the health condition associated with at least one of the members, in response to the relationship. The health condition may be any type of physical or mental health condition, disease, and/or ailment. For exemplary purposes the method and system will be discussed as they may relate to the health condition diabetes. A repository of health related characteristics associated with a population may be collected. The health related characteristics may be collected through sources such as medical claims, drug claims, and self-reported information. The characteristics may include health characteristics, lifestyle characteristics, and family history characteristics. The characteristics may include the amount of saturated fat, unsaturated fat, fiber, salt, alcohol, cholesterol, etc. that a member consumes in a give time period. The characteristics may include weight characteristic, such as a members weight, BMI (Body Mass Index), abdominal girth, etc. The characteristics may also include the person's blood pressure, standing heart rate, exercise habits (type and duration), and whether the member has hypertension. The health related characteristics of the population may be analyzed to establish the prevalence of diabetes among the population. For example, a medical claim having an ICD code with the prefix 250 is an indicator that the member may have diabetes. In addition, drug claims having a medication code descriptive of an anti-diabetes medication are indicators that the member has diabetes. The medical and/or drug claims are analyzed to determine if two claims indicating a member may have diabetes, and that are separated by at least three months, occur. If two claims meeting the criteria are identified, then the member is determined to have diabetes. For example, if two separate ICD codes in the 250 occur, separated by at least three months, or one such ICD code occurs and one drug code for anti diabetes medication occur, e.g., separated by at least three months, then the member may be determined to have diabetes.

Once the population has been analyzed to establish who has diabetes, the historical health related characteristics of the diabetics are then used to establish a relationship between diabetes and the health related characteristics. For example, the health related characteristics are used to establish a neural network model, or regression model. The trained neural network and/or regression model will then be able to predict the likelihood a member of the population will acquire diabetes. In one embodiment, the neural network will also be able to establish who has, or may acquire, the related diabetic characteristics of metabolic syndrome and or glucose intolerance. Alternatively, these may be inputs to the neural network if available.

The established relationship may be reviewed to determine what the pre-detectable characteristics associated with diabetes are. For example, it may be determined that salt intake, consumption of saturated fats, and alcohol consumption are three leading pre-detectable characteristics of acquiring diabetes. In addition, it may be determined that smoking is not a pre-detectable characteristic associated with diabetes. The population may then be reviewed using the established relationship. The health related characteristics of each member of the population not known to have diabetes may be analyzed using the relationship. The analysis may indicate the likelihood the person will acquire diabetes (e.g., 75% likely). In addition, the pre-detectable characteristics associated with diabetes that are exhibited by the person may be identified. In this manner, the likelihood of the acquiring diabetes may be established along with what pre-detectable characteristics are the primary contributors to this particular member having diabetes.

Once the population's health related characteristics are analyzed, the population may be ranked by the individual member's likelihood of acquiring diabetes. In this manner, the type of intervention may be recommended based on the risk of acquiring diabetes, and the pre-detectable characteristics the member exhibits. In one embodiment, the interventions may be recommended by using another relationship (or an elaboration of the predictive relationship) to automatically make the recommendation based on the health related characteristics of the member, which may include the likelihood of acquiring diabetes and specific pre-detectable characteristics exhibited, self-efficacy and readiness to change characteristics of the member, etc. In one embodiment, the intervention may include additional questionnaires or interviews to acquire more specific information associated with diabetes from the individual. Other forms of intervention include one on one counseling to convince the member of the seriousness of diabetes, the risk of acquiring diabetes associated with them, the ability to delay or prevent the onset of diabetes by changing specified lifestyle characteristics, and the specific actions the member may take to modify specific aspects of their lifestyle associated with the pre-detectable characteristics. For example, if dietary issues are causing the member to be overweight, the intervention may include, suggested changes to dietary consumption, cookbooks directed towards the desired diet, or even corporate sponsored diet counseling or involvement in a commercial diet control program. The specific intervention recommended may be based on the likelihood of acquiring diabetes the person has, the members willingness to change their diet and belief that they will be successful in long term dietary change, and how much of a factor dietary issues were in establishing this particular members likelihood of acquiring diabetes.

Once the intervention recommendation is provided additional monitoring may occur to determine if the member followed through with the recommendation (including why they did or didn't follow through), whether the intervention helped reduce the targeted characteristic (e.g., the targeted pre-detectable characteristic), and when the intervention did reduce the targeted characteristics, whether the ultimate occurrence of diabetes was either delayed (which may be a subjective determination) or prevented altogether. The results of this monitoring may then be used to update the established relationships. In addition, as incidents of diabetes occur, the health related characteristics of effected member may be used to further refine the established predictive relationship. In this manner, the health of the population may be analyzed and managed relative to diabetes.

The system can receive data from electronic medical records (EMRs), activity data from patient watches and wearable devices, population demographic information from govt databases, consumer profile information from credit card companies or consumer sales companies, provider (doctor, dentist, caregiver) entered information, one or more output registry databases. The EMRs may span multiple applications, multiple providers, multiple patients, multiple conditions, multiple venues, multiple facilities, multiple organizations, and/or multiple communities. Embodiments of the EMRs may include one or more data stores of healthcare records, which may include one or more computers or servers that facilitate the storing and retrieval of the healthcare records. In some embodiments, one or more EMRs may be implemented as a cloud-based platform or may be distributed across multiple physical locations. Example embodiments of the EMRs may include hospital, ambulatory, clinic, health exchange, and health plan records systems. The EMRs may further include record systems, which store real-time or near real-time patient (or user) information, such as wearable, bedside, or in-home patient monitors, for example. It is further contemplated that embodiments of the EMRs may use distinct clinical ontologies, nomenclatures, vocabularies, or encoding schemes for clinical information, or clinical terms. Further, in some embodiments, the EMRs may be affiliated with two or more separate health care entities and/or venues that use two or more distinct nomenclatures.

In embodiments, the EMRs described herein may include healthcare data. As used herein, healthcare data refers to any healthcare or medical care data related or relevant to a patient. Healthcare data may include, but is not limited to, clinical data and healthcare-related financial data. Clinical data, as used herein, refers to any healthcare or medical data particular to a patient. In embodiments, clinical data can be medical care or healthcare data resulting from or associated with a health or medical service performed in association with a clinician in a healthcare environment (e.g., lab test, diagnostic test, clinical encounter, ecare, evisit, etc.). Clinical data may include, but is not limited to, a health history of a patient, a diagnosis, a clinician assessment, clinician narrative, a treatment, a family history (including family health history and/or family genetics), an immunization record, a medication, age, gender, date of birth, laboratory values, diagnostics, a test result, an allergy, a reaction, a procedure performed, a social history, an advanced directive, frequency and/or history of healthcare facility visits, current healthcare providers and/or current healthcare provider location, preferred pharmacy, prescription benefit management data, an alert, claims data, a vital, data traditionally captured at the point of care or during the care process, a combination thereof, and the like. In the same or alternative embodiments, the clinical data may include medical compliance information. In certain embodiments, medical compliance information refers to a level of compliance of a particular patient with one or more prescribed medical treatments, such as medications, diet, physical therapy, follow up healthcare visits, and the like. In one or more embodiments, the clinical data may include data obtained from the natural language processing of one or more clinical assessments and/or clinical narratives.

In certain embodiments, healthcare-related financial data can refer to any financial information relevant to a patient, such as insurance data, claims data, payer data, etc. Such healthcare data (e.g., clinical data and healthcare-related financial data) may be submitted by a patient, a care provider, a payer, etc. In certain embodiments where the healthcare data is being submitted by anyone other than the patient, the patient may be required to approve of such submission and/or may opt-in to or opt-out of having such healthcare data being submitted.

In embodiments, activity data can refer to health actions or activities performed by a patient outside of, or remote from, a healthcare environment. Embodiments of activity data may include one or more data stores of activity data, which may include one or more computers or servers that facilitate the storing and retrieval of the activity data. In some embodiments, the activity data may be implemented as a cloud-based platform or may be distributed across multiple physical locations. Example embodiments of the activity data may include nutrition information and/or exercise information for a patient. In certain embodiments, at least a portion of the activity data may be recorded utilizing a personal fitness tracker, a smart phone, and/or an application provided by a smart phone. In various embodiments, the activity data may include data obtained from a patient's car. For example, in such embodiments, the activity data include data on the amount of driving the patient does versus the amount of walking the patient does.

In one or more embodiments, the activity data may be submitted by a patient, a third party associated with a personal fitness tracker and/or smart phone (such as a software developer or device manufacturer), a care provider, a payer, etc. In certain embodiments where the activity is being submitted by anyone other than the patient, the patient may be required to approve of such submission and/or may opt-in to or opt-out of having such healthcare data being submitted.

The patient and/or population demographic information may include age, gender, date of birth, address, phone number, contact preferences, primary spoken language, technology access (e.g., internet, phone, computer, etc.), transportation (e.g., common modes of transportation), education level, motivation level, work status (student, full-time, retired, unemployed, etc.), and/or income. In certain embodiments, the patient and/or population demographic information may include community resource information, which may include, but is not limited to, fitness facility information, pharmacy information, food bank information, grocery store information, public assistance programs, homeless shelters, etc. In embodiments, the motivation level can include the level of motivation a particular patient has for maintaining their health, which may be derived from other information (e.g., data from personal fitness tracker, indication the patient regularly visits a clinician for check-ups, consumer profile information, etc.). Embodiments of the patient and/or population demographic information may include one or more data stores of demographic information which may include one or more computers or servers that facilitate the storing and retrieval of the demographic information. In some embodiments, the patient and/or population demographic information may be implemented as a cloud-based platform or may be distributed across multiple physical locations. In embodiments, the patient and/or population demographics may be obtained through any source known to one skilled in the art. For example, in certain embodiments, at least a portion of the patient and/or population demographic information may be submitted by a third party that relies on census data. In various embodiments, the patient and/or population demographic information may be obtained from more than one source. In one embodiment, the patient may submit any or all of the patient and/or population demographic information. In certain embodiments, all or a portion of the patient and/or population demographic information may be anonymized using techniques known to one skilled in the art.

In one or more embodiments, the consumer profile information may include any or all of the spending habits of one or more patients within a population. For instance, in certain embodiments, the consumer profile information may include information associated with grocery store purchases, athletic or exercise equipment purchases, restaurant purchases, and/or purchases of vitamins and/or supplements. Embodiments of the consumer profile information may include one or more data stores of consumer profile information which may include one or more computers or servers that facilitate the storing and retrieval of the consumer profile information. In some embodiments, the consumer profile information may be implemented as a cloud-based platform or may be distributed across multiple physical locations. In one embodiment, a patient may provide the consumer profile information, for example, by linking checking account and/or checking account purchase information to at least a portion of the population health management system and/or to a health insurance carrier.

The care provider information may include any information relating to a particular care provider or healthcare facility. In one embodiment, the care provider information may include information relating to the number of healthcare providers and their specialties at a particular care provider location. In the same or alternative embodiments, the care provider information may include information relating to non-personnel type resources at a particular care provider location, such as the amount and types of medications and/or the amount and types of surgical or other medical equipment. In one embodiment, the care provider information may include one or more of address and contact information, accepted payer information, status on accepting new patients, transactional systems, primary spoken language, hospital affiliations, and/or care delivery models. In embodiments, the care provider information may include information relating to the availability of any or all resources at a particular healthcare facility including personnel and/or non-personnel resources. Embodiments of the care provider information may include one or more data stores of care provider information which may include one or more computers or servers that facilitate the storing and retrieval of the care provider information. In some embodiments, the care provider information may be implemented as a cloud-based platform or may be distributed across multiple physical locations. In one embodiment, the care provider information can be provided by a healthcare provider, and/or a third party, such as an insurance provider or management entity.

Information in the output registry databases may be categorized or classified according to, for example, claims, diagnoses, wellness, satisfaction, population directories, and the like. In various embodiments, each output registry may be used by, for example, a healthcare organization to manage the health of a population segment. In one or more embodiments, each output registry may be condition specific. By way of example, a healthcare organization or clinician may manage diabetic patients within a proscribed geographic area. The condition in this example is diabetes mellitus and the output registry may help the healthcare organization manage a population segment with this condition. The output registry may, in one aspect, include identified patients within a population segment who have this condition or have risk factors that may lead to the development of diabetes, for example. The output registry may further include grouped patients within an identified segment by degree of severity or risk, such as those grouped by the grouping component of the population health server. The grouped patients in an output registry may facilitate the generation of interventions or action workflows designed to reduce disease severity or risk and to improve outcome. Additional uses for the output registries are to measure outcomes related to treatment interventions and also to attribute patients within the identified segment to appropriate healthcare providers (e.g., primary care physicians, care managers health coaches, specialists such as endocrinologists, podiatrists, and the like).

In embodiments, the plurality of EMRs may be associated with a plurality of healthcare providers, a plurality of patients, a plurality of medical conditions, a plurality of healthcare venues and/or facilities, a plurality of organizations, and/or a plurality of communities. In certain embodiments, in addition to or in place of the healthcare data, the system can receive activity data from fitness devices, demographic information, e.g., the patient and/or population demographic information; consumer information, e.g., the consumer profile information; and provider information, e.g., the care provider information.

The system can identify a population of patients based on a set of criteria, which may, in one example, be received from a clinician device such as a blood pressure unit, among others. In one or more embodiments, the set of criteria may include one or more medical conditions. In the same or alternative embodiments, the set of criteria may include demographic information of one or more patients, such as age, gender, race, and/or location of residence. In one or more embodiments, the system may utilize any or all of the information and data such as: healthcare data, e.g., the healthcare data present in one or more EMRs; activity data; demographic information, e.g., the patient and/or population demographic information; consumer profile information; and care provider information.

In certain embodiments, to identify as many people as possible in a population that may have or have a particular medical condition of interest, the system may utilize clinical data, such as lab test results, in combination with other healthcare data. In such embodiments, the particular medical condition can be any condition where specific types of clinical information, e.g., lab test results, may be used to identify one or more patients that have or may have that condition. Exemplary conditions may include, but are not limited to, diabetes and heart disease. For example, in embodiments, the system may utilize diagnostic information, medication information, and/or one or more lab test results to identify a patient as having or potentially having diabetes. In such embodiments, by using information from one or more lab test results, the system may identify one or more patients that have diabetes or may have diabetes, even if they have not been formally diagnosed with diabetes or have not been prescribed diabetes medication. In the same or alternative embodiments, the system may utilize lab test results in combination with other healthcare data to identify pre-condition patients, which may allow early intervention to prevent a patient from developing a particular condition.

In one or more embodiments, the system can identify subsets of a population not based on a medical condition. For instance, in such embodiments, the system can identify subsets of a population based on aspects of one or more patients in a population of patients, e.g., age, gender, primary spoken language, income level, healthcare motivation level, education level, technology access (e.g., phone, computer, etc.), contact preferences, work status (student, full-time, unemployed, retired, etc.), healthcare facility visit history and frequency, advanced directives, and/or consumer profile information.

In various embodiments, the system can identify subsets of a population based on non-medical aspects of patients, specific care provider information, and/or population and/or community based resources in order to enable actions and care planning, measure compliance, improve care transitions, optimize utilization of resources, and contain costs.

In one or more embodiments, the system can group a population of patients based on a clinically relevant data from the EMRs. For example, in embodiments, the clinical data may include one or more of medication information, laboratory values, diagnostics, clinical narratives, and clinician assessments. In the same or alternative embodiments, the clinical data may include data obtained from the natural language processing of one or more clinical assessments and/or clinical narratives. In certain embodiments, the system can group a population of patients based on diagnostic codes, intervention codes, insurance claims, and/or medication information associated with each patient. The system can also group patients using substantially similar attributes can include one or more of disease risk levels and/or scores, one or more disease stages, and/or one or more healthcare objectives. For example, in certain embodiments, the system can group a population of patients, such as a population of patients identified as having or potentially having diabetes, into at least two groups corresponding to Type I and Type II diabetes.

The system can group based on venue location, specialty, spoken language, readmission rate, medical and/or prescription compliance level, socioeconomic status, address, employment status, marital status, education level, age, sex, dependents, race, ethnicity, insurance status, and primary spoken language, associated healthcare support system, and/or utilization level of healthcare facilities (including pharmacies). The grouping can finely classify individual patients as having a low, medium, or high medication compliance risk based on information related to the ability to access a pharmacy, the ability to pay for medications, and/or the presence of medication gaps in the healthcare record. In other embodiments, individual patients may be grouped based on the number of appointments made, the number of appointments scheduled, the number of appointments attended, the number of missed appointments, the type of appointment, the date and time of the appointment, the visit location, the venue, and whether or not the patient acknowledged the appointment (e.g., was the patient aware of the appointment).

The system can predict patients as having a low, medium, or high level of compliance with filling prescriptions based, at least in part, on the number of prescriptions written, the number of prescriptions filled, and the date and time the prescriptions were filled.

In certain embodiments, by having particular patients in a particular registry associated with a specific medical condition, e.g., a registry having patients with Type I diabetes, a health system may be able to provide proposed plans specific to at least a portion of the patients in a particular registry. For example, in one embodiment, a Type I diabetes registry may be utilized to provide a proposed plan of care for a Type I diabetic patient, and a Type II diabetes registry may be utilized to provide a proposed plan of care for a Type II diabetic patient. In such embodiments, the proposed plans of care for the Type I and Type II diabetic patients may be different.

The system can predict problems or avoidable complications and can trigger events and alerts associated with the patient. In certain embodiments, the healthcare provider may also be provided with a prediction of problems the patient may encounter. In the same or alternative embodiments, the healthcare provider can also trigger events to happen, send alerts to people, and identify the potential of having an avoidable complication within the next twelve months. For example, the system may indicate that a patient has a high risk of a heart related issue, and trigger events and/or alerts so that the patient is seen by a cardiologist, is checked more frequently, and is confirmed to be taking the appropriate prophylactic medication. In certain embodiments, the system can predict: patient compliance levels for various treatments or medications; the need for transition care; readmission rates, emergency department re-entry rates, future healthcare costs; future patient attrition; comorbidity trending; and/or the amount of care provider resources needed based on patient population information.

In embodiments, the system can consolidate the healthcare data for a patient across all venues and healthcare facilities, e.g., for any or all of the EMRs associated with a particular patient. In such embodiments, this can allow all clinical support decisions across all venues and programs to be consolidated for the patient.

In one exemplary embodiment to handle diabetic conditions, the system runs the following rules or criteria for testing for diabetes or prediabetes in asymptomatic adults:

1. Testing should be considered in all adults who are overweight (BMI≥25 kg/m2 or ≥23 kg/m2 in Asian Americans) and have additional risk factors:
   physical inactivity
   first-degree relative with diabetes
   high-risk race/ethnicity (e.g., African American, Latino, Native American, Asian American, Pacific Islander)
   women who delivered a baby weighing>9 lb or were diagnosed with GDM
   hypertension (≥140/90 mmHg or on therapy for hypertension)
   HDL cholesterol level<35 mg/dL (0.90 mmol/L) and/or a triglyceride level>250 mg/dL (2.82 mmol/L)
   women with polycystic ovary syndrome
   A1C≥5.7%, IGT, or IFG on previous testing
   other clinical conditions associated with insulin resistance (e.g., severe obesity, acanthosis nigricans)
   history of CVD 2. For all patients, particularly those who are overweight or obese, testing should begin at age 45 years.

3. If results are normal, testing should be repeated at a minimum of 3-year intervals, with consideration of more frequent testing depending on initial results (e.g., those with prediabetes should be tested yearly) and risk status.
   Categories of increased risk for diabetes (prediabetes)*
   FPG 100 mg/dL (5.6 mmol/L) to 125 mg/dL (6.9 mmol/L) (IFG)
   OR
   2-h PG in the 75-g OGTT 140 mg/dL (7.8 mmol/L) to 199 mg/dL (11.0 mmol/L) (IGT)
   OR
   A1C 5.7-6.4%
   Criteria for the diagnosis of diabetes
   A1C≥6.5%. The test should be performed in a laboratory using a method that is NGSP certified and standardized to the DCCT assay.*
   OR
   FPG≥126 mg/dL (7.0 mmol/L). Fasting is defined as no caloric intake for at least 8 h.*

OR 2-h PG≥200 mg/dL (11.1 mmol/L) during an OGTT. The test should be performed as described by the WHO, using a glucose load containing the equivalent of 75 g anhydrous glucose dissolved in water.*

OR

In a patient with classic symptoms of hyperglycemia or hyperglycemic crisis, a random plasma glucose≥200 mg/dL (11.1 mmol/L).

In another example for hypertension detection and management, the system applies rules on Definitions and Classification of Blood Pressure Levels

| Category | Systolic, mm Hg | | Diastolic, mm Hg |
| --- | --- | --- | --- |
| Optimal | <120 | and | <80 |
| Normal | <130 | and | <85 |
| High normal | 130-139 | or | 85-89 |
| Hypertension | | | |
| Stage 1 (mild) | 140-159 | or | 90-99 |
| Subgroup: borderline | 140-149 | or | 90-94 |
| Stage 2 (moderate) | 160-179 | or | 100-109 |
| Stage 3 (severe) | ≥180 | or | ≥110 |
| Isolated systolic hypertension | ≥140 | and | <90 |
| Subgroup: borderline | 140-149 | and | <90 |

Additive effect of hypertensinogenic factors (hatched areas) such as obesity and alcohol intake on hereditary systolic and diastolic BP can be accounted for in the BP. populations in which 1 (obesity) or 2 hypertensinogenic factors (obesity plus high alcohol intake) have been added. Notice that in these 2 populations the distribution curves are shifted to the right (high BP) and the number of hypertensive individuals is significantly increased when hypertensinogenic factors are added The system can aid in providing transition healthcare for one or more patients. For example, in certain embodiments, a population health server may provide transition management care associated with transportation of a patient to or from a healthcare venue for an appointment. Similarly, assistance for delivery of medication can be suggested if the patient does not have transportation.

1. A method of providing healthcare management services to a wearer, comprising:
    receiving 3D models of the wearer's feet and fabricating custom wearable devices with sensors to capture the wearer's weight and ambulatory activities;
    obtaining behavioral data from social network communications and mobile device usage patterns;
    saving the health data and behavioral data into a health data repository separate from the clinical data repository;
    mining the clinical data repository and health data repository for patients sharing similarity with the wearer, including one or more similar biomarkers associated with health conditions;
    identifying at least one similar health conditions and identifying one or more corrective actions recorded in the repository and the result of each action for the one or more health conditions;
    presenting the corrective action and result to the wearer and recommending an action to reduce risk from the predicted health condition; and
    monitoring the health condition using updates in the clinical data repository and health data repository.

2. The method of claim 1, comprising predicting in advance when the wearer needs medical attention based on the clinical data repository and the health data repository.

3. The method of claim 1, comprising identifying one or more doctors with cancellations or availability to treat the wearer to minimize delays and arranging one or more transportation providers to take the wearer to the doctor.

4. The method of claim 1, comprising determining dynamic trends related directly to the physiological states of the wearer during healthy and diseased states by detecting correlated patterns over time and unusual events.

5. The method of claim 1, comprising identifying health trends and features, assessing nonrandomness of the time-series, searching for spike events, and clusterizing the data to determine similar wearers.

6. The method of claim 1, wherein the health conditions comprise stroke, myocardial infarction, heart failure, and renal disease.

7. The method of claim 1, comprising:
    analyzing from the clinical repository blood pressure, obesity, insulin resistance, potassium intake, and calcium intake;
    analyzing from the health repository alcohol intake, salt intake, sedentary lifestyle, and stress; and
    presenting analytics and coaching the wearer to reduce blood pressure.

8. The method of claim 1, comprising analyzing obesity and alcohol consumption data.

9. The method of claim 1, wherein the health condition comprises diabetes.

10. The method of claim 11, comprising analyzing from the clinical repository blood pressure, obesity, insulin resistance, potassium intake, and calcium intake, and analyzing from the health repository sugar intake, sedentary lifestyle, and stress and presenting analytics and coaching the wearer to reduce blood pressure.

11. The method of claim 1, wherein the biomarker classifies the wearer as insulin resistant, insulin impaired, or insulin sensitive.

12. A method providing healthcare management services to a wearer, comprising:
    receiving a wearer's medical and family historical data;
    performing omic analysis on a sample of the wearer;
    detecting biomarkers indicative of a wearer health;
    periodically updating medical and family historical data, molecular analysis and biomarkers; and
    predicting a progression of the wearer's health.

13. The method of claim 17, comprising CT/CAT scan, MRI scan, PET scan, ultrasound, x-ray, mammogram, bone densitometry/scan, nuclear camera scan.

14. The method of claim 17, comprising analyzing circulating tumor DNA (ctDNA) and circulating tumor cells (CTCs).

15. The method of claim 17, comprising monitoring drug response or drug resistance.

Multi-Phase Manufacturing (MPM)

While conventional additive manufacturing 3D printers can be used for mass-customization of the shoes, the material available is limited and the print speed is slow, leading to fragile and expensive shoes. FIGS. 2A-2D show exemplary systems and techniques for manufacturing in volume with a wide range of materials are disclosed for fabricating shoes at mass customization scale. The system can also be further cleaned up after manufacturing using CNC for smoothing the soles, stitching fabrics onto the sole, or any other required post-processing manipulation of the fabricated shoes.

In one aspect, systems and methods are disclosed for shaping a reformable material by holding a volume of particles inside a container having a first elastomeric membrane surface; infusing the volume with a liquid to mobilize the volume of particles; and pressing a master shape into the membrane with atmospheric pressure.

In another aspect, a method to form an object includes infusing a liquid into a container having a first elastomeric membrane surface; pressing a master shape into the membrane with atmospheric pressure; and shaping a reformable material into the object according to the master shape.

In yet another aspect, a method to form an object includes infusing a liquid into a container having a frame with first and second elastomeric membranes; a first port to deaerate the volume of particles; and a second port to infuse the volume with a liquid for mobilizing the volume of particles; pressing a master shape into the membrane with atmospheric pressure; and shaping a reformable material into the object according to the master shape.

Implementations of the above aspects may include one or more of the following. The volume of particles can be deaerated. The liquid can be extracted through one or more screen elements placed proximal to the volume of particles. The atmospheric pressure continues to hold the particles in place against the elastomeric membrane when the master shape is removed from the outer surface of the membrane. The method includes heating and driving liquid from the particle volume. A residue of a binding adhesive is left to lock the particles into a continuous force-resisting mass. A complementary shape is impressed to the master shape in the membrane. A rigid outside frame can be used with top and bottom elastomeric membranes facing the top and bottom surfaces of the container. The master shape can be pressed against the top elastomeric membrane of the container by atmospheric pressure. The pressing operation includes applying a flexible vacuum cap which is sealed over the shape and against the container's top surface membrane; evacuating air from a space between the top membrane and the vacuum cap; extracting liquid from the volume; and pressing the particles within the container by atmospheric force acting in opposed directions against the vacuum cap and the bottom surface membrane. Air can be introduced into the vacuum cap, and then the cap and the master shape can be removed from the formed surface of the elastomeric membrane. The container is formed against the master shape. The method includes placing the master shape on an air-impermeable surface; placing a membrane of the container over the shape; and placing a vacuum cap or a vacuum-bagging film over the container to effect forming of the elastomeric membrane against the master shape. An envelope with a vacuum seal on its perimeter can be used to contain a mass of particles and to extract air from between the master shape and the envelope. The master shape can be placed on the top elastomeric surface of a first rigid-framed container and a membrane surface of a second container can be placed over the master shape. The second container fits inside the frame of the first container and a vacuum cap is placed over and sealed outside the second container against the surface membrane of the first container. The method includes evacuating the volume under the vacuum cap and pressing the master shape between the elastomeric sides of the first and second containers. The liquid is extracted so that the two volumes of particles are pressed together and against the membranes surrounding the contained shape. The vacuum cap can be vented with air and removed; the top container can then be removed; and the shape can then be removed from the membrane of the bottom container. The top container can be placed over the bottom container; and forming a closed, shaped cavity complementary to the surface of the master shape used to form the cavity. Two identical containers of either the first or the second container can be pressed around a master shape with or without using the vacuum cap. The containers can be joined and sealed by either a seal mounted on one or both of the containers or by seals mounted on a seal ring which fits between the two containers. The liquid can be extracted prior to the master shape being removed from the shaped reformable material. The liquid can be withdrawn to leave a residue of liquid on the shaped reformable material; and solidifying the residue. The method can include preforming a surface material over the master shape as with thermoforming or additive processing. The container walls can be air and liquid impermeable. An inelastic formable surface can be used that conforms to the master shape surface. A surface can be formed over the master shape to conform to the master shape and the shaped material surface can be pressed against the volume of particles without deforming the shaped material surface. The method includes providing a release surface to the master shape; pressing the master shape against the volume of particles to form the object against the release surface; and removing the object from the master shape with the release surface. The release surface can be applied to the master shape with a surface element covering the reformable material surface not overlaid with the master shape surface.

In another aspect, an apparatus to form an object in accordance with a master shape includes a container to hold a volume of particles, said container having a first elastomeric membrane surface; a first port to deaerate the volume of particles; and a second port to infuse the volume with a liquid for mobilizing the volume of particles; and a press coupled to the container to move the master shape into the membrane to shape a reformable material into the object according to the master shape.

Implementations of the above aspect may include one or more of the following. One or more screen elements can be placed proximal to the volume of particles to extract the liquid. Atmospheric pressure can be used to hold the volume of particles in place against the elastomeric membrane when the master shape is removed from the membrane. A heater can be used to heat and drive liquid from the particle volume. The container can be a rigid outside frame and top and bottom elastomeric membranes facing the top and bottom surfaces of the container, and wherein the master shape is pressed against the top elastomeric membrane of the container by atmospheric pressure. The apparatus can include a flexible vacuum cap sealed over the shape and against the container's top surface membrane; a third port to evacuate air from a space between the top membrane and the vacuum cap; and pressing of the particles within the container by atmospheric force acting in opposed directions against the vacuum cap and the bottom surface membrane. Air can be introduced into the vacuum cap and then the cap and the master shape can be removed from a surface of the elastomeric membrane. The master shape can be placed between an air-impermeable surface and the membrane of the container and wherein a vacuum cap or a vacuum-bagging film is placed over the container to form the elastomeric membrane against the master shape. An envelope with a vacuum seal on its perimeter can be used to contain a mass of particles and to extract air from between the master shape and the envelope. The master shape can be placed on the top elastomeric surface of a first rigid-framed container and placing a membrane surface of a second container over the master shape. The second container fits inside the frame of the first container and a vacuum cap is placed over and sealed outside the second container against the surface membrane of the first container. A vacuum pump can evacuate the volume under the vacuum cap and press the master shape between the elastomeric sides of the first and second containers. A pump can extract the liquid so that the two volumes of particles are pressed together and against the membranes surrounding the contained shape. The vacuum cap can be vented with air and removed; the top container is removed; and the shape is removed from the membrane of the bottom container and the top container is placed adjacent the bottom container to form a closed, shaped cavity complementary to the surface of the master shape used to form the cavity. The first and second containers can be identical and can be pressed around a master shape without using the vacuum cap. The containers can be joined and sealed by either a seal mounted on one or both of the containers or by seals mounted on a seal ring which fits between the two containers. A seal ring can be used to channel vacuum or air pressure between the containers and to hold the master shape in a precise orientation and position between the two opposed containers. An expander can be used within the container to press the particulate material against cavity walls of the container. The apparatus can include a second container cooperating with the first container to form a complementary cavity from the master shape; and a third container placed in the complementary cavity to replicate the master shape. A rigid frame or a flexible-edge frame can be used. The frame can form a continuous surface complementary to a master shape's surface. A second elastomeric membrane can be used, and the elastomeric membranes can overlap or abut each other. Additional containers each having a membrane can be used with the container's membrane to form a continuous surface of membranes. Further, additional containers can be used to form a shape complementary to the interior of a master cavity.

In another aspect, an apparatus to form an object in accordance with a master shape includes a container to hold a volume of particles, said container having a frame with first and second elastomeric membranes; a first port to deaerate the volume of particles; and a second port to infuse the volume with a liquid for mobilizing the volume of particles; and a press coupled to the container to move the master shape into the membrane to shape a reformable material into the object according to the master shape.

Implementations of the above aspect may include one or more of the following. The second membrane is bonded to the frame. The first membrane is mounted to a seal. A clamp can secure at least one membrane to the frame. One or more ports can be provided on the frame. Liquid, evacuation, and vacuum-activated seal tubes can be mounted to the frame. A rim evacuation screen element can be positioned in the frame. The frame can be rigid or flexible. A vacuum activated seal can be provided on the frame. A tube can be used for evacuating and filling the container. Double layer screens having feed elements to distribute and extract liquid through the volume of particles can be used. One or more screens can be used to conform to the master shape. One or more internal screens can be mounted with the particles flowing on both sides of each internal screen. The frame can have one or more containers joined together around the master shape or alternatively can have one or more containers joined by vacuum seals. One or more feed tubes can connect to an interior element inside the membrane. A flexible spine element can be used within an interior cavity of the container. One or more reinforcement fibers can be used, and in certain implementations, the fibers can be distributed in bundles within the volume of particles. An air pump or source can be used to provide internal pressurization. A vacuum source can provide a vacuum between a cavity in the container and the container. An air source and a vacuum source can alternately pressurize and vent the container to distribute the volume of particles therein. A seal ring can be used. The seal rings can be mounted against seals or can be mounted with attached seals. The attached seals can be vacuum activated. A second container can be joined with the container and wherein a vacuum is formed in an interior of the joined containers. The master shape can be mounted on the seal ring. Flanges can be mounted to control a mating line between opposed membranes of containers. A second container can be positioned within a cavity formed by an outside container. A vacuum seal can be used with a vacuum cap. A vacuum tube can be used that penetrates through the membrane. A vacuum cap with mounted container can be used in place of the membrane. One or more screen elements can be placed proximal to the volume of particles to extract the liquid. Atmospheric pressure holds the volume of particles in place against the elastomeric membrane when the master shape is removed from the membrane. A heater can be used to heat and drive liquid from the particle volume. The container can have a rigid outside frame and top and bottom elastomeric membranes facing the top and bottom surfaces of the container, and wherein the master shape is pressed against the top elastomeric membrane of the container by atmospheric pressure. An envelope with a vacuum seal on its perimeter can contain the mass of particles and extract air from between the master shape and the envelope. The master shape can be placed on the top elastomeric surface of a first rigid-framed container and a membrane surface of a second container placed over the master shape. An expander within the container can be used to press the particulate material against master shapes and against cavity walls of other containers. The apparatus can have a second container cooperating with the first container to form a complementary cavity from the master shape; and a third container placed in the complementary cavity to replicate the master shape. A second elastomeric membrane can be used that either overlaps or abuts the adjacent membrane. Additional containers each having a membrane coupled to the container can be used to form a continuous surface of membranes. Additionally, one or more additional containers can form a shape complementary to the interior of a master cavity.

In yet another aspect, a base station is disclosed to form an object in accordance with a master shape. The base station includes a liquid receiver; a vacuum source to evacuate air from the liquid receiver; an air compressor, pump or source to generate pressurized air; and a controller coupled to the liquid receiver, the vacuum source and the air compressor to form the object.

Implementations of the base station can include one or more of the following. Tubes can be used to provide vacuum and to control the flow of liquids to and from the receiver. Valves, sensors, and other circuits can be interfaced with the controller. An electrical power source can be used to provide power to operate valves, sensors, the vacuum pump and the air compressor. The controller can be a menu-driven process controller. A heater can be used to vaporize and expel liquid from containers of reformable material. The reformable material creates contours of the master shape or alternatively can be molded against a complementary surface of an elastomeric membrane. The liquid contains a soluble binder, which can be left on a shaped volume of particles. The binder locks a shaped volume of particles in place after the liquid is removed. The heater can be a radiant heater, a convective air heater, microwave heater, radio-frequency heater, or inductive heater. The heater can include one or more heating elements within the container. The heater is controlled by the controller. A container can be used to hold a volume of particles, said container having a frame with first and second elastomeric membranes; a first port to deaerate the volume of particles; and a second port to infuse the volume with a liquid for mobilizing the volume of particles; and a press coupled to the container to move the master shape into the membrane to shape a reformable material into the object according to the master shape. Alternatively, the container can have a first elastomeric membrane surface; a first port to deaerate the volume of particles; and a second port to infuse the volume with a liquid for mobilizing the volume of particles; and a press coupled to the container to move the master shape into the membrane to shape a reformable material into the object according to the master shape. The container can include a rigid outside frame and top and bottom elastomeric membranes facing the top and bottom surfaces of the container, and wherein the master shape is pressed against the top elastomeric membrane of the container by atmospheric pressure. The base station can also include a flexible vacuum cap sealed over the shape and against the container's top surface membrane; a third port to evacuate air from a space between the top membrane and the vacuum cap; and pressing of the particles within the container by atmospheric force acting in opposed directions against the vacuum cap and the bottom surface membrane. The master shape can be placed between an air-impermeable surface and the membrane of the container and a vacuum cap or a vacuum-bagging film can be placed over the container to form the elastomeric membrane against the master shape. The vacuum pump can be a mechanical pump or an air driven pump such as a Venturi pump. A second vacuum pump can be used. Isolating valves can be used, and a regulator and one or more valves can be used to pressurize a liquid tank. A vent valve can also be used to cycle from a vacuum source to a pressure source. A three-way valve can route air and vacuum to the liquid tank. A filter can be used to prevent particulate carryover. An air-liquid separator and/or a level indicator can also be used. A vacuum, pressure, liquid and temperature sensor can provide data to the controller for process control. A heat exchanger can be used to condense vapor. A slurry transfer tank can be connected to the container. The container can be a single unit, or can have a plurality of containers adjacent to or inside the container to form a cavity. The containers can be mated with a seal ring.

In yet another aspect, a method to shape a reformable material includes holding a volume of particles inside a container having a first elastomeric membrane surface; and infusing the volume of particles with a liquid; agitating the liquid to provide one or more surges of liquid to mobilize the volume of particles; and pressing a master shape into the membrane with atmospheric pressure.

Implementations of the above method may include one or more of the following. The method may provide locally distributed surges or globally distributed surges. The surges can exert differential liquid forces on particles to displace them relative to one another and facilitate their movement into a closely-packed volume. A differential pressure can be applied between a master shape side and a liquid-particle side of the membrane. The pressure between a vacuum cap and the membrane can be decreased to move the membrane in a first direction or increased to move the membrane in a second direction. The membrane is free to move relative to the master shape. Excess liquid can be removed to leave particles against the membrane. Air can be evacuated from space between the membranes. The particles can be packed against the membranes and the master shape. The liquid with the vacuum cap and membrane pressed against the master shape can pack the particles against the membranes and the master shape. The agitating operation can include pulsing or vibrating the liquid. The vibration frequency can be adjusted to displace one particle relative to another to keep the particles moving freely in relation to one another. The amplitude of the liquid pulsation can be proximally equal to a diameter of the particles. A first surge of liquid can be directed towards a desired transport direction and a second surge smaller than the first surge can be directed in an opposite direction to the transport direction. The agitating of the liquid can be used to minimize blockage. The method includes maintaining the volume of the container constant and completely filled to force the particles against the master shape. The method includes extracting transitional liquid from the container; and adding new liquid equal in volume to the transition liquid.

In yet another aspect, a shape-reformable composition includes a carrier medium having a carrier density; and a plurality of solid bodies having a density substantially similar to the carrier density, said solid bodies being transitionable from a formable state to a three dimensional solid shape. The bodies can have a density substantially lighter or heavier than that of the carrier if they have a high ratio of surface area to volume. The bodies can be stiff, flexible or elastomeric. The bodies can be regular or irregular and can be of substantially different types intermixed.

Implementations of the composition can include one or more of the following. The carrier medium fills voids or interstices between the solid bodies such that the voids or interstices are free of air or gas bubbles. The solid bodies can have near-liquid or fluent mobility during the formable state. The solid bodies can transition to the solid shape through an introduction and an extraction of a predetermined amount of the carrier medium. The solid bodies can be positioned in a container having a first elastomeric membrane surface. Liquid can be introduced to mobilize the volume of particles. A master shape can be pressed into the membrane with atmospheric pressure. The resulting solid shape is a stable, force-resisting shape. The solid bodies and carrier medium form a reversible state-changeable mixture. The carrier medium can be a liquid or a gaseous froth. The shape can be a reformable mold or a reusable template to capture dimensions of impressed shapes for transfer to a mold.

In other aspects, a system is disclosed for holding a volume of particulate material inside an air and liquid-impermeable container with at least one elastomeric membrane surface; deaerating the volume; infusing the volume with a liquid to cause it to be mobile; pressing a master shape into the membrane via atmospheric pressure; and extracting the liquid through one or more screen elements which are placed in or adjacent to the particle volume. The extraction causes atmospheric pressure to press the particles against the contours of the shape and against each other. This pressure continues to hold the particles in place against the elastomeric membrane when the master shape is removed from the outer surface of the membrane. The system further has a means to heat and drive liquid from the particle volume and, in certain embodiments, to leave a residue of binding adhesive which locks the particles into a continuous force-resisting mass.

Operation of one embodiment is as follows with a particular embodiment of the container which has a rigid outside frame and a membrane face on the top and bottom surfaces. With the particle volume infused by liquid, a master shape is pressed against the top elastomeric membrane of the container by atmospheric pressure, thereby causing the shape to impress a complementary shape in the membrane. This pressing is accomplished through use of a flexible or elastomeric vacuum cap which is sealed over the shape and against the container's top surface membrane, following which air is evacuated from between the top membrane and the vacuum cap. Liquid is then extracted from the volume and the particles within the container are pressed together by atmospheric force which acts on all exterior surfaces of the tool-bed but in particular in opposed directions against the vacuum cap and the bottom surface membrane. Air is then introduced into the vacuum cap, the cap removed and the master shape removed from the formed surface of the elastomeric membrane.

In another embodiment, the container is formed against a master shape with the process of liquid infusion, a pressing action via atmospheric pressure and a liquid extraction process. This embodiment is essentially a flat envelope with a flexible outside rim and two opposed elastomeric membranes. To use this embodiment a master shape is placed on an air-impermeable surface, a membrane of the container is placed over the shape, and either a vacuum cap or a vacuum-bagging film is placed over the container to effect forming of the elastomeric membrane against the master shape. The envelope may also have a vacuum seal on its perimeter and so has the combined function of containing a mass of particles and of serving to extract air from between the master shape and the envelope.

In implementations, there can also be a combined use of the first and second containers described above. A master shape may be placed on the top elastomeric surface of the first rigid-framed container and then a membrane surface of the second container is placed over the shape. The second container fits inside the frame of the first container and a vacuum cap is placed over and sealed outside the second container against the surface membrane of the first container. When the volume under the vacuum cap is evacuated the master shape is pressed between the elastomeric sides or faces of the two containers. Liquid is then extracted so that the two volumes of particles are pressed together and against the membranes surrounding the contained shape; the vacuum cap is vented with air and removed; the top container is removed; and the shape is removed from the membrane of the bottom container. When the top container is again placed over the bottom container, a closed, shaped cavity is formed which is complementary to the entire surface of the master shape which was used to form the cavity.

In yet another embodiment, a combination of containers can be used in which two identical containers of either the first or the second type may be pressed together around a master shape without use of the vacuum cap. In this case the containers are joined and sealed by either a seal mounted on one or both of the containers or by seals mounted on a seal ring which fits between the two containers. The seal ring may be further employed to channel vacuum or air pressure between the two containers and to hold the master shape in a precise orientation and position between the two opposed containers. The seal ring may also furnish access to the formed cavity for the purpose of injecting a moldable material into the cavity.

In yet another embodiment of the container the container itself is formed into a replica of a master shape, or into a shape complimentary to a master cavity by another combination of the elements and processes described above. The exterior of this third type of container may be formed entirely from an elastomeric material or may be formed from a combination of elastomeric, flexible and rigid materials. Though the container might be shaped against a single surface, it can also be shaped over substantially its entire surface by confining it within a master cavity formed by two or more closely-fitting mold parts. Key to this forming process is an expansion means within the third container which presses the particulate material against the cavity walls.

In another embodiment, there is combined use of the containers which employ the three types of containers described above for a single purpose. The first or second types can be used to form a complementary cavity from a master shape. The third type of container can then be placed in the cavity, which is now used as a master cavity, and the third type formed complementary to the master cavity contours, thereby creating a replica of the original master shape.

It can be appreciated that there are numerous variations of containers and varied combinations of containers which can be employed either to form a surface which is complementary to the exterior surface of a master shape in part or in whole, or to form a surface or surfaces complementary to the interior contours of a hollow master shape or master cavity. For instance more than one container of the first type (rigid frame) or second type (flexible-edge) can be employed to form a continuous surface complementary to a master shape's surface, with the elastomeric membranes of the containers either overlapping or being abutted together. Containers of the second type may also have a membrane and particle configuration that allows two or more of the containers to be "tiled" together to form a continuous surface of particle-backed membranes. Likewise two or more containers of the third type can be employed together to form a shape complementary to the interior of a master cavity.

In yet other embodiments, a forming system also includes a base station which provides evacuation of air, liquid infusion into and liquid extraction from the particle filled containers. The base station also furnishes vacuum forces to enable the forming operations to be performed on the various containers either singly or in combination. The base station comprises a liquid receiver; onboard vacuum system or provision to connect to an external vacuum source; an air compressor or provision for external connection to pressurized air; valves, fittings and tubing or piping to provide vacuum and to control the flow of liquids to and from the containers; an electrical power supply to operate the valves, process sensors and any onboard mechanical vacuum pumps and air compressors; and a menu-driven process controller to operate the base station.

In another embodiment, a forming system includes a heater which may be used to vaporize and drive out liquid from the particle filled containers, and further to heat any materials which may be used to recreate the contours of the original master shape through molding against the complementary surface of the formed elastomeric membrane. The vaporizing or drying process is especially advantageous when the liquid contains a soluble binder which remains on the pressed-together particles and locks the shaped volume of particles in place when the liquid has been driven out of the container. The heater may take numerous forms to include a radiant heater, a convective air heater, heating elements within the particle-filled container, and various types of inductive (e.g., microwave or radio-frequency) heaters. The heater may be powered and controlled by the base station and its controller, or the heater may be powered and controlled separately.

Next a reformable shoe making embodiment is detailed. In this system, the 3D model of the shoe as customized by the user or a doctor for the user is sent 1003 is provided to a reformable shape object fabricator 1006, which is detailed next. The fabricator 1006 renders a physical model of the 3D model and then applies a state-changeable mixture that includes uniform, generally ordered, closely-spaced solid bodies and a liquid carrier medium, with the liquid filling any voids or interstices between the bodies and excluding air or gas bubbles from the mixture. Within the mixture, the solid bodies can be caused to transition from a near-liquid or fluent condition of mobility to a stable, force-resisting condition. To create mobility, a small excess quantity or transition liquid is introduced to create a fluent condition by providing a slight clearance between the bodies which permits the gently-forced introduction of at least two simultaneous slip planes between ordered bulk masses of the bodies at any point in the mixture. Transition to the stable condition is caused by extraction of the transition liquid, removing the clearance between bodies and causing them to make stable, consolidated contact. FIG. 4A shows a computer controlled system for fabricating parts that whose dimensions are specified in a data file and rendered by a CAD/CAM software such as Solidworks or Autocad or even Paint, and the object described in the data file needs to be fabricated. Conventional printers print a layer at a time and can take significant time in making a single product. To accelerate the production process, the system of FIG. 4A takes 3D data from a computer with 3D CAD design 1002 and provides the information to an actuated 3D shape generator 1004 that is placed inside of a reformable object copier 1006. The 3D shape generator 1004 forms the 3D object, and the object copier 1006 reproduces copies of the formed 3D object in minutes, thus greatly accelerating production of mass-customized products which otherwise takes hours on a 3D printer.

The 3D shape generator 1004 is a complete computer actuated system that is enclosed in the object fabricator 1006. CAD data is downloaded by wire or wireless connection to the shape generator 1004. Based on the desired dimensions, one embodiment of the 3D shape generator 1004 forms a 3D object by having an array of computer controlled moveable pins whose height is adjusted in accordance with the CAD design file, and the overall shape is smoothed by a Lycra sheet or felt sheet. The pins or rods lift the felt or Lycra sheet to form a 3D object based on the CAD design file. In this embodiment, an array of N×N micro hydraulic actuators can be used to form the shape. This embodiment is a dense hydraulic planar pin-rod matrix array. Another embodiment actuates an N×N pin-rod matrix driven by servomotors. In either case, each pin-rod is controlled individually, similar to pixels on a screen except that the pixel has height as well.

In one embodiment, the N×N matrix can be an array of electro-mechanical pins positioned in a frame. The frame is adapted to hold the plurality of pins in a parallel position to one another in a series of columns and rows, such that the distal ends of the plurality of pins together form a flat virtual plane. Each pin of the plurality of pins includes an elongated housing member defining a linear axis therethrough, and a pin member adapted to slide linearly in either direction along the axis. Each of the housing member includes an upper electromagnet, and a lower electromagnet separated from the upper electromagnet. Each of the electromagnet is adapted to move its respective pin member linearly in either direction. Each of the pin member includes a linear potentiometer, a, magnet and an electronic transmitter attached to an opposite end to the distal end, such that when each of the pin members are moved linearly each respective linear potentiometer sends a signal to its respective transmitter which in turn sends an electronic signal describing its movement within its respective housing member, a plurality of electronic wires respectively connected to each transmitter, such that electronic signals can be relayed to and from each respective pin; an analog-digital converter connected to the plurality of electronic wires and adapted to convert the analog electronic signals relayed by the transmitters into digital format to be transmitted, processed, stored, and then converted back into analog form for return transmittal to the set of pins. A processor is connected to the converter and adapted to retrieve the electronic signals from the converter, store them, and retransmit them back to the converter when desired, such that a user can displace the pin members from the virtual plane in any pattern, have electronic signals sent, processed, stored, and returned to the same set of pins, or another separate set of pins, at a later time to thereby displace the pins to the same positions as the original pattern chosen by the user.

In one embodiment, the pin array device has each of the housing member of each pin comprise an upper frame upper electromagnet, upper spring, lower electromagnet, lower spring and shield along the entire upper frame wall to separate magnetic field between each interactive pin. The lower frame consists of the outer fixed part of the potentiometer and electronic transmission from electronic transmitter to both electromagnets. The pin consists of a magnet, a mobile portion of the potentiometer, electronic transmitter that picks up all the wire and sends position signal and feeds the power to both electromagnets via the lower housing. The electronic signal may be a Pulse Width Modulation signal, and the displacement of each of the pin members is proportional to the strength of the Pulse Width Modulation signal received by the electromagnets.

Figure 2A:
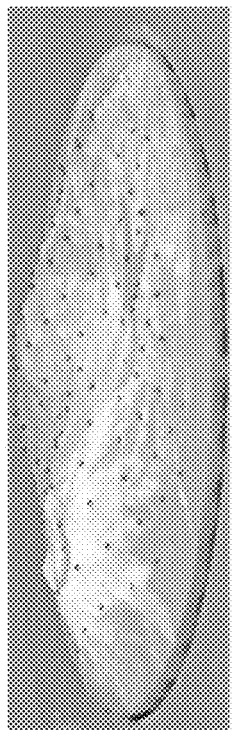
Figure 2B:
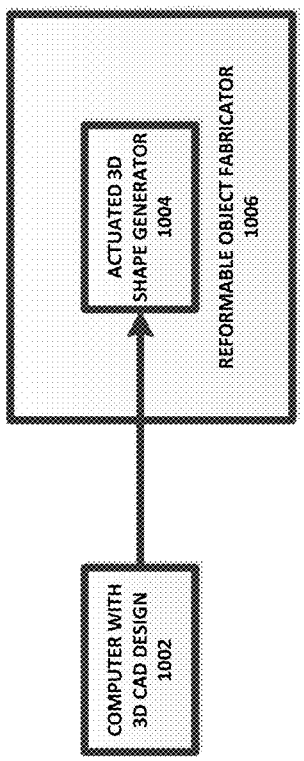

FIG. 2B shows the shape of the object when a felt cover or a Lycra cover is placed above the pins to form a 3D structure that can be digitally controlled using a CAD output to form a 3D object that can then be copied or fabricated using the reformable object fabricator 1006.

Figure 2C:
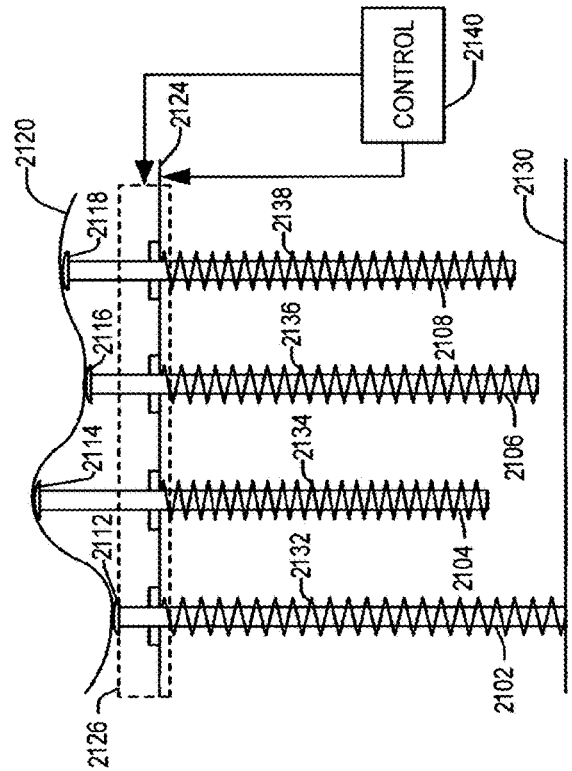
Figure 2D:
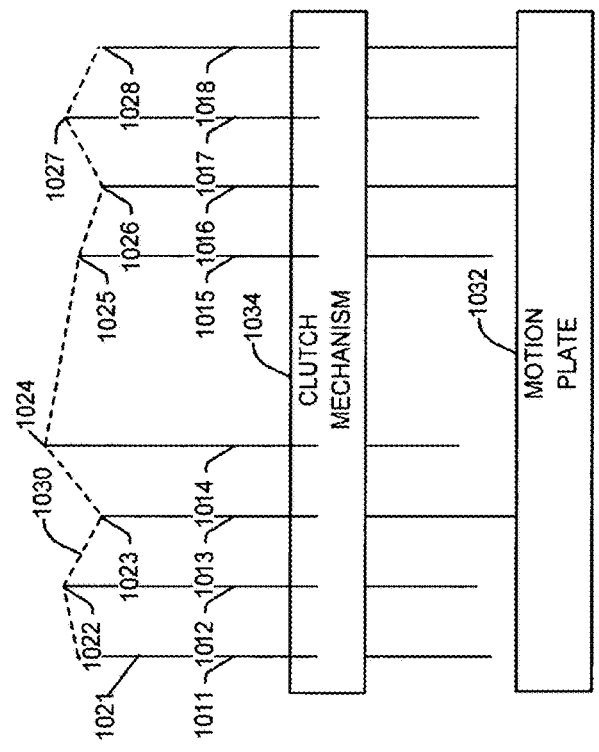

In yet another embodiment shown in FIGS. 2C-2D, the pins are moved by the action of a plate, common to all or a portion of the pins, that can extend and retract along a single axis of motion. A clutch mechanism cooperates with the moving plate to fix the pins at a desired position. In an exemplary embodiment, the shape generator 1004 can include a membrane covering the pins. A plurality of pins 1011-1018 arranged in an array such that respective head portions 1021-1028 associated with the pins collectively define a surface 1030. It will be appreciated that the area of array is not necessarily defined by two Cartesian dimensions. For example, the pins could be arranged along a spherical or hemispherical surface, with the array spanning the azimuthal and polar dimensions across the surface of the sphere. The position of a given pin (e.g., 1011) can be adjusted along an axis of motion.

In one embodiment, an optional motion plate 1032 can be provided to move the pins along the axis of motion as to adjust the position of the pins. The motion plate 1032 can be moved by reasonable mechanical or electromagnetic means.

For example, the plate 1032 can be moved via an electrical motor, a hydraulic assembly, or one or more solenoid coils exerting a magnetic force.

A clutch mechanism 1034 is operative to arrest the motion of a given pin at a desired position. The respective positions of the pins can be selected to deform the display surface into a desired raised image. The clutch mechanism can comprise reasonable means for selectively arresting the motion of the pins. For example, the clutch mechanism 1034 can comprise components for mechanically or magnetically engaging the pins.

One embodiment provides an upper plate with a plurality of apertures through which corresponding pins forming the object's surface can pass. The pins can include head portions with areas larger than that of their respective apertures, to more fully tessellate the display surface and to help maintain the pins within the apertures. The upper plate can house part or all of a clutch mechanism that selectively engages one or more pins to maintain the pins at a desired position. The upper plate houses one or more banks of solenoids that shift the position of one or more portions of the clutch (not shown) that physically communicate with the pins. In an exemplary embodiment, the solenoids shift the position of one or more bars such that they contact or release circumferential grooves on the surface of the pins. This embodiment also provides a lower plate and a base plate disposed parallel to the upper plate along one or more support posts. A lifting plate can be suspended between the lower plate and the base plate on one or more guide posts. The lifting plate can be raised or lowered via a motor and belt system to adjust the position of the pins. For example, the pins can be reset to a fully raised position by raising the lifting plate to its maximum height. The movement of the guide pins and the action of the clutch mechanism can be regulated by a processor.

FIG. 2D illustrates a side view of an exemplary computer shaped object that can be reproduced or fabricated formed in accordance with an aspect of the present system. As shown in FIG. 2E, two facing and opposite bed of pins 2210-2212 can form a 3D shape for the sole or insert. The insert and/or the shoe can be produced in discrete sizes such as US sizes 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, and 18, for example. Thus, a plurality of sized beds can be used, or one large pair of beds covering size 20 can be used to produce all other smaller sizes. Turning back to FIG. 2D showing one of the beds 2210-2212, the selected view of the 3D object creator comprises one row of four pins 2102-2108. It will be appreciated that a functioning computer controlled 3D object creator can contain a large number of pins arranged across multiple rows in order to reproduce the shape of the 3D object with high fidelity.

In an exemplary embodiment, the rows containing the pins 2102-2108 are staggered as to form a honeycomb pattern. Accordingly, the pins 2102-2108 are arranged in a plurality of linear rows and one or more staggered columns. Alternatively, the pins can be arranged in a Cartesian grid, such that both the rows and the columns are linear. It will be appreciated that other methods of arranging the pins can be utilized, and that the placement of the pins will vary with the necessary size and spacing of the pins, as well as the desired shape (e.g., flat, spherical, recessed) of the array.

In the illustrated display, the pins 2102-2108 have respective cap portions 2112-2118 that define a raised surface. The cap portions 2112-2118 can be covered by an elastic membrane or felt layer 2120 to provide a relatively smooth surface for the object. The use of the pin caps 2112-2118 and the membrane 2120 will depend on the application. The pins 2102-2108 pass through respective apertures in a stationary, outer plate 2124. The outer plate 2124 houses a clutch mechanism 2126 that acts to maintain the pins in their desired positions. In an exemplary implementation, the clutch mechanism 2126 can comprise a series of row bars and column bars having two associated positions. In a first, open, position, a given bar allows the pins within its associated row or column to move freely. In a second, restraining, position, the bar is moved to physically contact the pins at one of a plurality of evenly spaced grooves on the pin, maintaining the pin at its position. The spacing of the grooves corresponds to a desired resolution of the display 2100. The position of the bars can be changed via one or more banks of solenoids. In an exemplary embodiment, the bars are biased, by a spring or similar mechanism, to remain in the restraining position, until a solenoid is actuated to move the bar into an open position.

During operation, the pins can be reset into a fully extended position by a reset plate 2130. The reset plate 2130 can then be incrementally withdrawn to allow the pins 2102-2108 to retract toward the interior of the display device. In an exemplary embodiment, the reset plate 2130 is moved by a motor and belt arrangement. The pins 2102-2108 have associated springs 2132-2138, with each spring (e.g., 2132) attached at a first end to the underside of the outer plate 2124 and at a second end to the end of the pin (e.g., 2102) opposite the cap portion (e.g., 2112). When the pins 2102-2108 are fully extended, the springs 2132-2138 are compressed against the underside of the outer plate 2124. The springs 2132-2138 thus provide a tensive force on the pins 2102-2108 as to draw the pins toward the interior of the object being formed.

The movement of the reset plate 2130 and the operation of the clutch mechanism can be coordinated by a controller 2140 to adjust the position of the pins 2102-2108. The controller 2140 can provide information relating to the desired pin positions to the projector. The reset plate 130 can be incrementally withdrawn toward the interior of the object. In an exemplary embodiment, the reset plate 2130 withdraws in increments equal to the spacing between the grooves on the pins 2102-2108. After each retraction of the plate, the clutch mechanism 2126 can be selectively activated to release one or more of the pins, while leaving others secured. The tensive force provided by the springs 2132-2138 pulls the ends of the released pins flush against the reset plate 130, such that the released pins retract to a uniform level defined by the position of the reset plate. The secured pins remain at their previous level. The pins are then resecured by the clutch mechanism, and the plate is retracted by another increment. This process is repeated as the reset plate 2130 retracts to leave each pin at a desired level of extension.

In another embodiment, the pins pass through respective apertures in a stationary, outer plate housing a first portion of a clutch mechanism that acts to adjust the pins into desired positions. In an exemplary implementation, the first clutch portion can be piezoelectric restraints for the plurality of pins. In a default position, a given restraint loops around its associated pin, but allows the pin to move freely. Upon the application of an electrical current, the restraint contracts as to physically contact its associated pin at one of a plurality of evenly spaced grooves on the pin. This fixes the pin to the outer plate, maintaining the pin at a stationary position. The spacing of the grooves corresponds to a desired resolution of the 3D object being formed. The pins also pass through respective apertures in a moving plate which can be moved by a motor and belt arrangement. The moving plate houses a second portion of the clutch mechanism with piezoelectric restraints for the plurality of pins. The movement of the moving plate and the operation of the first/second clutch portions can be coordinated by a controller to adjust the position of the pins. The moving plate oscillates in a direction normal to the outer plate and a base plate between a first position, closest to the base plate and a second position, closest to the outer plate. In an exemplary embodiment, the first position and the second position are separated by a distance equal to the spacing between adjacent grooves. The pins begin in a default position, fixed to the outer plate by the first clutch portion. In an exemplary embodiment, the default position of the pins is a fully withdrawn position (e.g., the first clutch portion engages the uppermost groove of each pin). Since the default position of the pins is known, the controller can determine the distance between the default position and a desired position as a number of increments, as defined by the groove spacing of the pins. The controller can thus select one or more pins to extend by one or more increments. While the moving plate is in its first position, the selected pins are released by the first clutch portion. Simultaneously, the second clutch portion engages the selected pins, such that the pins are fixed to the moving plate. The moving plate can then be moved to its second position. Once the plate reaches the second position, the second clutch portion releases the selected pins, while the first clutch portion reengages the pins. It will be appreciated that the motion of the moving plate can be controlled by the controller such that the first clutch portion can engage the pins at a groove one increment below the default position. Accordingly, the selected pins are extended by one increment. This can be repeated a number of times, to allow one or more pins to be moved to a desired position up to a maximum extension. The final position of each pin will be determined by the number of times the first and second clutch portions are activated for the pin. This can be controlled by the controller according to the desired position of the pin. Once the pins have been positioned, the controller can direct the object fabricator 1006 to copy the 3D object formed by the pin grid 3D shape generator.

In another exemplary clutch mechanism, a pin can be encased in a solid restraining material having a low melting point. For example, the restraining material can be an alloy of lead and one or more other metals. The restraining material is contained in a container having a relatively high melting point. The clutch mechanism disengages by applying heat from a heat source to the restraining material in order to bring it to a liquid state. The heat source can be applied by a laser apparatus (not shown) directed on the restraining material or by a heating element associated with the container. In an exemplary implementation, the container is the heat source, producing resistive heat upon the application of an electrical current. While the restraining material is in a liquid state, the pin can move freely through the aperture. Once the heat source is deactivated, the restraining material cools and returns to a solid state, restraining the pin.

In yet another exemplary clutch mechanism, a wire has shape memory properties is looped around a pin. The material with shape memory properties has the ability to return to an imprinted shape when heated. A desired shape can be imprinted into the material by molding the material at a high temperature and maintaining the desired shape as it cools. Below a threshold temperature, the material is relatively flexible and can be deformed away from the imprinted shape with relative ease. Once the material is heated above the threshold temperature, however, it reverts back to the imprinted shape with some force. In an exemplary implementation, the wire is a formed from nitinol, an alloy of nickel and titanium. The wire is shaped such that the loop is opened around the pin and the pin can move freely through the loop. A current can be applied to the wire to heat the wire via resistive heating to a temperature greater than its threshold temperature. This causes the wire to return to its imprinted shape, engaging the pin as the loop closes. The wire returns to its imprinted shape somewhat forcefully, such that the tensive force on the ends of the wire is insufficient to restrain it. In an exemplary embodiment, the wire is looped around a groove in the surface of the pin to facilitate engagement of the pin. When the current is no longer applied, the wire 352 cools and returns to its more malleable state. Once the wire cools below threshold, the tensive force applied can once again deform the wire into an open shape, releasing the pin.

Form and Operation of Particle-Filled Containers

FIGS. 3A-D show a first container embodiment, a master shape and a vacuum cap, and further show a sequence of operations to create a shaped impression, complementary to the master shape, in the surface of one elastomeric membrane face of the container. Turning now to FIG. 3A, a container 5 is shown with a rigid container frame 10 and elastomeric top and bottom membranes 20 and 25, resting on a base 13 which separates the bottom membrane 25 from contact with any surface that the base 13 and the container 5 rest on. The top membrane 20 is bonded to a perimeter frame 17 so as to have an air-tight interface between the container frame 10 and the membrane 20. The container frame 10 is affixed to a continuous vacuum-activated seal 30 which is bonded to the container frame 10. The seal 30 is resilient and acts much like a suction cup to hold the perimeter frame 17 to the container frame 10. The bottom membrane 25 is bonded directly to rigid container frame 10 since the membrane 25 is not a working surface wearer to damage, in contrast to the working surface of membrane 20 which is subject to damage. In one embodiment, the bottom membrane 25 can be affixed by a perimeter frame and vacuum seal as described above. In yet another embodiment with more complexity, mechanical clamps and a pressure seal can be employed to affix either top or bottom membranes. Tubes 40, 50 and 60 penetrate a toolbed or a container frame 10. The tube 40 communicates with a seal 30 through an opening 45, and the seal 30 affixes the membrane 20 to the container 5 by a vacuum (indicated by arrow 43) acting through the tube 40. The vacuum seal 30 can be inactivated by introducing air through the tube 40, allowing the membrane 20 and the frame 10 to be removed in order to insert or remove a volume of particles from the container 5, or to replace a damaged membrane 20 or internal screen element. The tube 50 communicates with a main particle screen 55 which is overlaid with a volume of particles 80. Arrow 53 indicates the flow of liquid into the particle volume through screens 55. The particle screens 55 serve to hold all particles in the container 5 while allowing liquid to flow in and out of the particle mass. There is a double layer construction of both screens 55 with the tubes 50 and 60 communicating between the layers. The particles cannot penetrate the outer layers of the screens and so do not move into the tubes as air is evacuated or liquid extracted. Detail 57 of FIG. 7B-1 shows extensions of tubing 50 penetrating into the center of the double-layered screens. The extensions have perforations that enable distributed liquid flow along the length of the tube inside the screen. The tube 60 communicates with a rim evacuation screen element 65 which follows the entire inside upper perimeter of frame 10 and is likewise perforated along its length within element 65. Arrow 63 points outward to indicate deaerating vacuum force acting on the container volume via the evacuation element.

Turning now to the top of FIG. 3A, a vacuum cap 90 is shown with a continuous flexible or elastomeric membrane 95 bonded to another perimeter frame 100, the frame also having a continuous vacuum-activated seal 105 bonded to the frame 100. The seal 105 is identical in design and function to the seal 30. The vacuum cap 90 has a tube 110, which communicates with the vacuum seal through an opening 115, and a tube 125 which in turn communicates with the underside of membrane 95 through a port 120.

A master shape 130 is shown resting on membrane 20. The master shape will used to form a shaped impression in the membrane as described next. To prepare for the forming process, a membrane 20 is sealed to the container; air is removed from the volume of particles as shown by arrow 63; and liquid is introduced into the particle volume as shown by arrow 53. Liquid flow is cut off when there is sufficient liquid to allow particles to move in relation to adjacent particles as displacing force is exerted on either the top or bottom membrane of the container.

FIG. 3C shows a side view of the container frame 10 with a vacuum cap 70 resting over the master shape 130 prior to being sealed against the membrane perimeter frame 15 to which the membrane 20 is bonded, with the membrane affixed using the seal 30 to the container frame 10. The master 130 is resting on the unformed surface of membrane 20 with the movable particles between membranes 20 and 25.

FIG. 3D shows a cutaway view with the vacuum cap 90 affixed by the seal 105 against the perimeter frame 15 by vacuum through the tube 110 as shown by an arrow 113. In addition the space between the vacuum cap membrane 95 and the top membrane 20 has been evacuated through the tube 125 as shown by an arrow 127. The vacuum cap membrane 95 is pressed down against the master shape 130 and against the surface membrane 20 by atmospheric pressure which also acts opposedly against container bottom membrane 25. Liquid is then extracted by a pump or vacuum from the particle volume through a tube (not shown) through the particle screen 55, causing atmospheric forces acting on bottom membrane 25 to pack the particles against top membrane 20 which is forced against the master shape since air has been evacuated from between the vacuum cap membrane and top membrane 20. Any leakage of air into the container, which would add atmospheric pressure back to the container and so reduce the packing force on the particles, can be removed by continuing vacuum extraction of liquid through particle screens 55 or by vacuum extraction through the perimeter evacuation screen element 65.

When the master shape 130 is removed from the surface of the membrane 20, an impressed shape 135 remains which is complementary to the shape 130. The differential pressure on the container by vacuum extraction is continued, thereby maintaining opposed atmospheric forces that act to keep membranes 20 and 25 pressed against the particles and so immobilizing them to keep the impressed shape stabilized. In form the seal is a continuous channel with the legs angled outward. The channel has a single opening and a vacuum and vent tube connected to it as described with reference to FIG. 3A. The material of the seal is resilient since the legs will be pressed against a surface and must conform to and seal against the surface. The legs are separated by a sufficient distance that they will be pressed into contact with the surface by atmospheric pressure with a greater force per unit area than atmospheric pressure. In function, when the legs of the channel are pressed against a smooth surface and the vacuum introduced inside the channel, the seal legs deform against the surface and the deformed area is substantially less than the area inside the channel. In experiments a ratio of deformed area to inside area of 1 to 2 has been shown to be very effective in sealing against a smooth surface if the durometer of the seal's elastomeric material is around 40. In operation the seal is simply placed against or gently pressed against a smooth air-impermeable surface. A vacuum is introduced through the tube, extracting air from within the seal and so enabling atmospheric pressure to force the seal against the surface. Any leakage from atmosphere outside the seal is scavenged by the vacuum and so does not enter the volume inside the perimeter of the seal even if a full vacuum is imposed on that volume. To release the seal air is introduced via the tube or a small blade can be slipped between the seal and surface to break the internal vacuum.

The particles can be a reversible state-changeable mixture having a plurality of solid bodies and a carrier medium, with the carrier medium filling any voids or interstices between the bodies. Within the mixture, the solid bodies can be caused to transition from a formable state, preferably a near-liquid or fluent condition of mobility, to a stable, force-resisting condition through introduction and then extraction of a slight excess quantity of the carrier medium beyond that required to fill the interstices of the bodies when closely packed. In most embodiments, the carrier medium is a liquid preferably excluding any air or other gases from the mixture, and most of the discussion will revolve around such embodiments. However, some embodiments use a carrier medium that is a liquid-gas froth.

The mixture can be rapidly shifted from a formable (preferably near-liquid or fluent) state to a stable force-resisting state and back again to the formable state, through slightly altering the carrier-solid proportions of the mixture, and the system further provides methods and apparatus for using the mixture. Embodiments are characterized by one or more of the following advantages: the ability to pressurize a mixture and drive it against a complex surface as if it were a liquid; the ability to create a "near-net" or extremely accurate representation of a shape due to the negligible volumetric change that accompanies a state change; the ability to effect the state-change with a very small volume of single-constituent transfer and with consequently small actuation devices without the need for a vacuum pump, without chemical reactions, and with no need for thermal or electrical energy to be applied to the mixture; the ability to greatly alter the volume of any elastic or otherwise dimensionally changeable container, envelope or chamber through the free-flowing transfer of the mixture from one container to another; and the ability to tailor the mixture to satisfy a wide variety of physical specifications in either the flowable or the stable state.

The mixture can be used in reformable molds or other shaping tools, and in reusable templates that capture the dimensions of impressed shapes for transfer to a mold. The mixture can also be used in any product or shape that benefits from the incorporation of arbitrary reformability or precise reconfigurability. The mixtures further provide useful properties for use in a wide range of shock-absorbing, leveling, protective and supportive elements or apparatus.

The mixture in its formable state may be loosely compared to quicksand, while the mixture in its stable state may resemble hard-packed sand or even cement, with the transition being caused by the transfer of a relatively small amount of liquid. Hence the mixture, while in the formable state, includes enough liquid to fill the interstices between the nested solid bodies, and an excess amount of liquid that is referred to as the transition liquid. In the stable state the transition liquid is absent and the bodies are completely packed or nested.

In preferred embodiments the solid bodies are uniform, generally ordered, and closely spaced, with the predominate mass of the bodies close-packed and touching. To create mobility, the transition liquid is introduced in just-sufficient quantity to create a fluent condition by providing a clearance between some of the bodies, which clearance permits the introduction of at least two simultaneous slip planes between ordered masses of the bodies at any point in the mixture. The bodies themselves separate freely from one another under movement of the liquid and without turbulent mixing, and shift relative to one another generally in ordered bulk masses. The bodies should be of a density that is close enough to that of the liquid to permit flow of the bodies along with the liquid, or should have a size or structure that facilitates movement of the bodies along with the liquid.

In an embodiment, the surface of the mixture while in the formable state is first made to conform to a desired shape. The bodies in the mixture are then caused to transition from the fluent condition to the stable condition through extraction of the transition liquid. This extraction removes the clearances required to provide slip-planes between ordered masses of the solid bodies, thereby causing the bodies to make nested, packed, interlocking or otherwise stable consolidated contact. The mixture, now in the stable state, has a surface that conforms to the desired shape.

The mixture can be used in molds, templates or other products through holding the mixture in, or transferring quantities of the mixture while in the fluent condition into and out of variable-contour or variable-volume containers or chambers. The mixture can be stabilized by removal of the transition liquid, which may cause an elastic membrane to be pushed against the consolidated bodies by ambient pressure, or by transition liquid removal that causes the solid bodies to pack together under liquid tensile forces, thereby creating an ordered, deformation-resisting structure through surface friction or through surface adhesion of one body to another.

In certain embodiments, the mixture can be held inside a container or transported into a container with a flexible, elastically deformable and stretchable wall. The process then extracts the transition liquid from the mixture so as to cause body-to-body contact and force-resisting stability through pressure external to the container acting on the confined, ordered, abutting bodies. Transfer of fluent mixture into and out of the containers, or displacement of mixture within the containers can be accomplished by pressure forces within the mixture, with these forces being distributed uniformly throughout the mixture by the liquid carrier medium.

This distribution of uniform pressure against the surface of each body, coupled with the clearance volume furnished by the transition liquid, assures that the bodies are not forced against one another while the mixture is in the fluent condition. This elimination of body-to-body compression forces in turn prevents the bodies from sticking together and resisting displacement while the mixture is in the fluent condition. Pressure forces in the liquid can be exerted through pressing a shape against an elastic, stretchable membrane that constitutes at least one surface of a chamber substantially filled with the fluent mixture, or such forces within the liquid medium of the fluent mixture may be induced by a two-way pump or other transfer system.

The bodies themselves may have various geometries and may be provided within a state-change mixture in one uniform type, or there may be two or more types or sizes of bodies dispersed or layered within a mixture. For example spherical bodies of one size might have smaller bodies filling the interstices between the larger bodies, or a layer of short fiber bodies might float above a layer of spherical bodies. Flake-like bodies can be also be used, in which case the flat faces of the bodies can be pressed against one another to create a force-resisting body mass. The flat faces provide many times the contact area of abutting spheres, with accordingly higher friction or adhesion potential when consolidated against one another. If the flakes are in the form of a laminate that has one side heavier than the carrier medium and one side lighter, and if the flakes are closely spaced and in a medium which suppresses turbulence and solid body tumbling, the bodies will tend to be supported in, and to be consolidated in, an ordered parallel configuration. In this case, as with the spherical bodies, the transition liquid quantity will be just sufficient to create shear motion of body masses under low displacement forces.

Mixtures with more than one type or size of body can be used with the bodies either intermingled or layered separately, as by differing densities or the inability of bodies of one layer to pass through bodies in the adjacent layer. Bodies of different sizes or types may also be separated from one another by flexible or extensible porous materials or fabrications that allow passage of liquids but not of the confined bodies.

The degree of accuracy or irregularity on the surface of a stabilized mass of the mixture is dependent upon the relationship between the fineness of the bodies and the dimensions to be captured, a covering membrane's thickness and conformability, and the size and degree of regular packing order of a state-change mixture's solid bodies. If the bodies are very small compared to the contours of a shape that is to be replicated, or if the interstices between larger bodies in the mixture are filled by such smaller bodies, the mobile solid bodies of the mixture will consolidate and assume a near-net shape relative to any impressed shape when the transition liquid is extracted from the mixture.

In additional embodiments, the mixtures are stored external to one or more molds, tools or fixtures, and are selectively introduced, stabilized and made fluent again in the tools. Formulas of the mixtures or solid bodies and liquids of the mixtures may be stored separately, and may be mixed or separated as required for effective operation of separate elements of a forming or tooling system.

In yet other embodiments, flexible elements containing state-change mixtures are used to capture exterior or interior contours of a shape and to transfer the contours to other state-change elements. Through such "templating" operations a negative of a shape or surface may be produced and then a shape or surface identical to the first may be produced by forming the surface of a mixture against the transfer template. Individual elements might also be used to transfer portions of one shape to another shape and so create variations that combine the contours of two or more shapes into a single shape.

In still other embodiments, several elastic, extensible elements filled with state-change mixtures slide freely upon one another and relative to the contained mixtures in order to conform to highly contoured shapes. These embodiments would be used when the elastic stretch of a single membrane element is not sufficient to capture details of a shape.

Further embodiments include methods of displacing fluent mixtures within variable-volume flat elastic envelopes by pressing the envelopes against shapes with exterior air or liquid pressures, or pressing with physical elements such as bundles of rods or fingers that slide relative to one another. The pressing force pressurizes the liquid carrier medium and causes the envelopes to extend and conform to the shapes as the contained fluent mixtures flow within the envelopes under the uniformly distributed pressure forces within the liquid. Embodiments also contemplate the creation of hollow voids within a mixture-containing envelope, with the impressed shape causing the collapse of the voids so that the mixture need not be pumped into and out of a chamber to permit capture of a shape.

Yet other embodiments include methods for creating a sculptable condition in specific state-change mixtures through placing the mixtures in a quasi-stable state. The solid bodies are held in contact by extraction of a portion of the transition liquid, yet have sufficient lubricity or low contact friction to be displaced relative to one another by externally imposed forces. The bodies can be displaced into voids created within a mass of the quasi-consolidated mixture, or can be progressively displaced along the surface of the mixture from one region of the mass to another. In some embodiments, properties of flow of the mixture and the resistance to deformation of the abutted bodies are predetermined so as to be a function of the imposed external forces, and so to be subject to variable control that allows intermediate quasi-stable, sculptable or displaceable conditions within or on the surface of the bulk mixture.

State-change mixtures may also use solid bodies along with a state-changeable liquid carrier medium. The method for changing the mixture from fluent to stable and back again is, as described above, through transfer of a small amount of excess liquid; however, the mixture can be further solidified by changing the state of the carrier medium from liquid to solid.

In yet another embodiment, a state-change mixture is consolidated within a mold chamber and the liquid carrier or a second liquid component is circulated while held to a pressure below ambient. Through heating and cooling of the circulating liquid, the mold itself can be heated or cooled.

Still another embodiment of the state-change mixture has solid bodies that are hollow and very light, and a carrier medium comprising a liquid-gas froth of similar density. The froth is destroyed when extracted since the gas within it expands and separates from the liquid component; then the froth is reconstituted from the liquid and gas and reintroduced into the body mass to recreate a fluent mixture. The liquid component of the froth may be a solvatable (solvent-releasable) adhesive that can be dried to hold the consolidated bodies together and then re-dissolved by the frothed carrier medium. Very light bodies can also surrounded by a denser liquid, with the mixture likewise becoming fluent and then stabilized with transfer of a small quantity of transition liquid; however, the tendency of the bodies to adhere together under contact pressure is preferably countered, or liquid-like transfer of the mixture, especially through small lines or passages, becomes difficult if not impossible.

In additional flat envelope embodiments internal and external elements improve their functioning as lightweight tooling and templates. Included are methods to support these mixture-containing envelope structures, both internally with flexible reinforcements and externally with tubular 'foot' structures that also contain state-change mixtures. The flat envelopes may also be backed or supported by liquids or dry media with the ability to capture precise impressions of a shape with the ability to be switched from a liquid-like state to a firm state, or even to a fully hardened state that resembles concrete yet can be returned to a formable condition.

The state change from liquid-like to solid-like properties within the mixtures is effected by the transfer of a small amount of excess carrier medium, the transition liquid, into and out of the mixtures. When the transition liquid is present, preferably in just-sufficient quantity to create the degree of support and clearance that provides for at least two slip-planes, the solid bodies have a degree of mobility similar to that of the liquid medium of the mixture. The slip-plane condition of mobility can be generated through very small liquid pressure differentials or through externally imposed forces that displace the carrier liquid and the supported bodies along with the liquid. Ordered bulk masses of the bodies can shift relative to other ordered masses at any point within a continuous volume of the mixture, and the location of the slip-planes can fluidly shift under any slight differential force transferred from one body to another. It is preferred to prevent frictional contact between bodies during such force transfer by having the liquid medium of the mixture furnish a viscous or 'streaming' resistance to contact, and also for the medium to furnish a degree of body-surface lubrication so that light body contacts do not create friction between bodies.

Lubricity under high contact forces, as is required for many lubricating media, is not necessary within the mixtures since the bodies are in effect free-floating during flow, with any imposed liquid pressure forces being uniformly distributed against the surface of each body. For example a nearly ideal aqueous liquid medium can be formed by dissolving a small quantity of a soluble long-chain polymer such as polyethylene oxide into water. The medium carries solid bodies of a similar density without turbulence and friction-producing contact, allows the bodies to make non-lubricated surface contact when the medium is extracted, and causes the bodies to readily separate when the transition liquid is reintroduced.

When the transition liquid is extracted so that the solid bodies are in a stable configuration with ordered, packed and consolidated contact, the degree of resistance to externally imposed forces depends on such tailorable, engineered physical properties as body shape, body elasticity and compressibility, body surface properties of roughness, smoothness or natural molecular adhesion, residual adhesiveness or lubricity of the liquid medium on the contacting surfaces, surface tension of the medium, and variations of liquid medium or body properties with changes of temperature or pressure; alteration of the resistance properties through replacement of the first liquid with a second liquid medium, rinsing of the bodies and the first medium with a second or sequential liquid media, vapors or gaseous fluids; and any other engineered variations in the bodies and first liquid medium, and in other sequential introductions of various fluids into the mixtures or through the consolidated bodies. Any adhesive or clinging contact between the bodies is preferably relieved through polar molecular action of the first liquid medium, or through an intermediary treatment with other liquids or fluids prior to reintroduction of the first liquid medium.

The container works with quickly reversible state-change mixtures which can be rapidly shifted from a near-liquid or fluent state to a stable force-resisting state through slightly altering the liquid-solid proportions, and the system further provides methods and apparatus for utilizing the mixtures. Embodiments are characterized by one or more of the following advantages: the ability to pressurize a mixture and drive it against a complex surface as if it were a liquid; the ability to create a "near-net" or extremely accurate representation of a shape due to the negligible volumetric change which accompanies a state change; the ability to effect the state-change with a very small volume of single-constituent transfer and with consequently small actuation devices, with a low-energy mechanical actuation, and without requiring a vacuum pump, thermal, chemical or electrical energy to be applied to the mixture; the ability to greatly alter the volume of any elastic or otherwise dimensionally changeable container, envelope or chamber through the free-flowing transfer of the nearly solid mixtures from one container to another; and the ability to tailor the mixtures to satisfy a wide variety of physical specifications in either the flowable or the stable state.

The mixtures can be employed in reformable molds or other shaping tools, and in reusable templates which capture the dimensions of impressed shapes for transfer to a mold. The mixtures can also be used in any product or shape which benefits from the incorporation of arbitrarily reformability or precise reconfigurability. The mixtures further provide useful properties for but are not limited to application in a wide range of shock-absorbing, leveling, protective and supportive apparatus.

It can be appreciated that there are numerous variations of containers and varied combinations of containers which can be employed either to form a surface which is complementary to the exterior surface of a master shape in part or in whole, or to form a surface or surfaces complementary to the interior contours of a hollow master shape or master cavity. For instance more than one container of the first type (rigid frame) or second type (flexible-edge) can be employed to form a continuous surface complementary to a master shape's surface, with the elastomeric membranes of the containers either overlapping or being abutted together. Containers of the second type may also have a membrane and particle configuration that allows two or more of the containers to be "tiled" together to form a continuous surface of particle-backed membranes. Likewise two or more containers of the third type can be employed together to form a shape complementary to the interior of a master cavity. More details on the reformable manufacturing are disclosed in commonly owned patents to Jacobson et al including U.S. Pat. No. 6,398,992 and Pub. No. 20050035477 and 20070187855, the contents of which are incorporated by reference.

Figure 5:
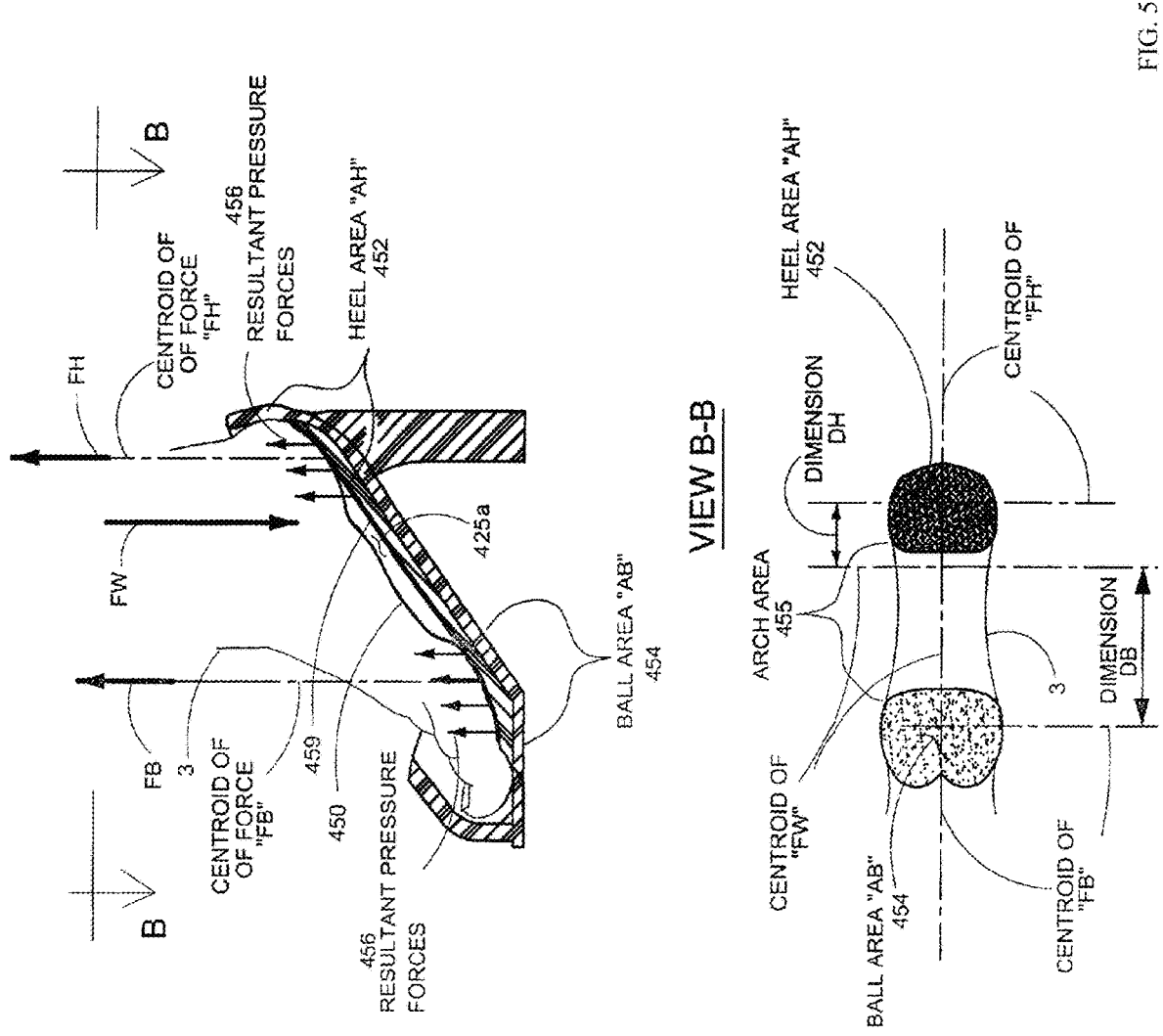
FIG. 5 shows exemplary forces acting on the high heel shoe and how the support structure enables a comfortable walking experience for the wearer.

FIG. 4 shows an exemplary process to produce a mass-customized high heel shoe, while FIG. 5 shows exemplary forces acting on the high heel shoe and how the support structure enables a comfortable walking experience for the wearer.

Turning now to FIG. 4, the system includes receiving a foot representation into memory of a processor; transforming the foot representation to rest above a high heel shoe representation at a predetermined heel height from a ground; determining a digital structure to support the heel, a foot arch and a ball area of the foot; and with the digital structure, fabricating a high heel sole or insole to provide foot support. One embodiment performs the following:
  receiving a foot model into memory coupled to a processor (401)
    generating an elevated foot model with a heel at a predetermined heel height from a ground and determining a structure to support a foot arch and a ball area of the foot model (403)
  fabricating a high heel sole with the optimized structure to support the foot (405).

In one implementation, the fabrication operation includes the following 3D printing operations:
  forming a reformable master shape from the foot model with the optimized structural lattice;
  holding a volume of particles inside a container
  infusing the volume with a liquid to mobilize the volume of particles
  pressing the reformable master shape into the membrane with atmospheric pressure to form a mold of the sole
  depositing a sole material into the mold.

Next, more details are discussed in the determination of the digital structure to support the heel, a foot arch and a ball area of the foot. Referring to FIG. 5, the position of foot 3 in a shoe shown in side view cross section) having an elevated heel 462 and a sole 459. The sole of the foot, as is commonly known, refers generally to the underside of foot 3 and encompasses heel 452, arch 450 and ball of the foot 454. Because the resultant pressure, when using a conventional insole or no insole, the wearer typically experiences discomfort due to the concentration of pressure only in ball area 454 and heel support area 452. In an elevated heel shoe, the concentration of pressure is disproportionately greater on the ball of the foot 454 than heel of the foot 452.

To provide support, an insole 459 (or when extended toward the ground as a sole 459) contacts and conforms to substantially all of arch 450 by filling in the volume 425*a* under the foot. This is done by digitally capturing the user's foot model and adjusts the digital model to the desired high heel shoe. The heel portion of the model of the foot is set to the same height as the heel height. When the heel of the foot is raised off the ground, the system updates the height/curvature of the arch of the foot to increase proportionally. The foot support shapes occur at the desired heel height such that the sole of the foot has continual contact with the upper portion of custom sole with a more secure and contoured fit of foot to an arch in an elevated heel shoe. Because of the substantial contact between insole 459 and arch 450, sole or insole 459 of the embodiment provides a configuration that results in increased weight distribution throughout the sole of the foot 3 on insole 459.

While a conventional shoe does not contact the arch 450 of foot 3 when used in a shoe with an elevated heel. The lack of contact results in a void area that is between the bottom of the foot arch 450 and the top of the sole or the insole 459. The lack of contact support when a person is standing in a shoe with an elevated heel has a known adverse effect on the person's foot 3 of foot discomfort.

As shown in FIG. 5, the downward force from the weight of a person standing in an elevated heel shoe is shown by line FW. When force FW is exerted by the weight of a person in a downward direction, opposing forces represented by lines FH, FC, and FB are exerted. Force line FH is force exerted upward in the region of the heel, force line FC is the upward force exerted in the center region of the foot, and force line FB is the upward force exerted in the area of the ball of the foot 454. Each line of upward force FH, FC, and FB imparts an area outward from the center of force commonly known as a dimension. Dimension, in terms of force analysis, is the outward distance from the center of a force in which effects of force are detected. Dimension DH represents a relative length along heel 452 in all directions outward from FH in which the affects of FH are imparted. Dimension DC represents a relative length along arch 450 in all directions outward from FC in which the affects of FC are imparted. Dimension DB represents a relative length along ball area 454 in all directions outward from FB in which the affects of FB are imparted. The resultant sum of force imparted on a surface is pressure. Pressure is typically measured in bidimentional units. In one implementation, pressure is measured in pounds per square inch (psi) or any other units of pressure measuring force per unit area.

The cross section view along section line B-B shows resultant pressure distributed along arch area 455 and heel area 452. The resultant pressure from the force FW of a person standing in shoe in which insole 459 has been placed is distributed substantially throughout foot 3. Heel area 52 shading is shown in darker markings to indicate the heel area.

The weight of a person standing in a shoe with elevated heel 62 in which conventional insole 459 has been placed imparts resultant pressure on ball area 454 and heel support area 452.

Thus, as seen in FIG. 5, insole or sole 459 results in a distribution of pressure imparted by the force of a person standing in shoe. The distribution of pressure is substantially throughout the sole of foot 3. Distribution of force when using insole 459 will result in reduced strain on foot 3 and increases foot comfort when wearing a shoe with an elevated heel 62 and insole 459. Thus, the custom fitted insole 459, which is a part of the high heel shoe provides for the custom fit and beneficial pressure distribution.

In another embodiment, insole 459 is mass produced, and not customized. Insole 459 is constructed and arranged, when mass produced, such that a user can select a shoe in which insole 459 more closely conforms to the wearer's foot. Thus the mass produced non-customized insole 459 are preformed to more closely conform to the wearer's foot. The increased contact area, between the wearer's foot and insole 459, results in more surface area in which the force of body weight can be distributed. This is because the non-customized insole 459 of this embodiment is preformed based on the elevated heel height of the mass produced shoe size which incorporates this non-customized insole 459 and though not customized to the actual foot of the wearer, it is pre-shaped to a wearer's foot based on the size and the elevated heel height of the shoe.

Unlike conventional orthotics, the custom molded support is not placed on top of a shoe insole, the custom molded support is the entire inner sole of a shoe. The custom molded sole or insole used in high heeled shoes will distribute a person's weight (wearing the shoe) more evenly throughout the sole of the foot and the shoe resulting in a significantly decrease in the amount of pain and/or pressure that people experience in the ball of their foot, generally the area where the toes join the rest of the foot, while wearing high heeled shoes. Preferably, the high heel shoes are custom made, but a custom insole can be fabricated to support and provide comfort for users wearing brand-name shoes.

They can be constructed and arranged to fit any foot type or deformity. For example, women with bunion deformities often have difficulty finding shoes that do not have a strap that sits over the bunion (a strap over a bunion may cause pain to the wearer). Straps in shoes can be positioned to avoid the bunion. Additionally, any other bony prominences in the foot can be accommodated in the custom molded sole or insole and in any other parts of the shoe in which accommodation would be beneficial to the wearer. Apertures can be placed in custom molded sole or insole. A bony prominence is automatically accommodated in custom molded sole or insole. The cover may be supplemented any suitable cover and may include, but would not be limited to a bandage or additional casting material placed over bony prominence. Custom molded sole or insole constructed and arranged to accommodate bony prominences will ultimately result in a custom molded sole or insole and ultimately finished shoe which can offload painful bony prominences on the bottom of feet. The shoe and incorporated custom molded sole or insole will conform to any perturbance of the foot and would not be limited to accommodating bony prominences.

The custom molded sole or insole may be formed of any suitable material. Suitable materials for standard shoes may include but would not be limited to, polypropylene, polyethylene, acrylic, graphite, fiberglass, carbon fiber material, a composite material, or combinations thereof. Suitable materials are any materials that are able to be used in the press molding process. Said materials should be thin, durable, stiff, and heat moldable. In a preferred embodiment, custom molded sole or insole would be covered with a thin layer of cushioning, on either or both sides, such as foam and the like as is commonly done in the manufacture of shoes.

For athletic shoes to be constructed, custom molded sole or insole may be made of a material providing a greater cushioning to a user. Examples of materials suitable for a custom molded sole or insole in an athletic shoe would include, but would not be limited to, polypropylene, polyethylene, acrylic, graphite, fiberglass, carbon fiber material, a composite material, Ethylene-vinyl acetate (EVA), Nickelplast™ (a combination of ethylene vinyl acetate and polyethylene, available from Alimed, Inc., Dedham, Mass.), polyethylene foams, PLASTAZOTE® (Closed cell crosslinked polyethylene foam, available from Zotefoams, PLC, Surrey, England), cork, or combinations thereof.

The different suitable materials for custom molded sole or insole in both standard and athletic shoes can be used by themselves or as a combination. For example, a standard shoe custom molded sole or insole may be formed of a combination of polypropylene, polyethylene, and acrylic. An example of a custom molded sole or insole for an athletic shoe may include a combination of EVA and polyethylene foams. These examples are for illustrative purposes only and not intended to limit the combinations of materials available to for the custom molded sole or insole.

Alternatively, any combination of any suitable moldable materials may be used to produce custom molded sole or insole. It is known that many of the suitable materials for forming custom molded sole or insole have different densities. A custom molded sole or insole may be constructed and arranged such that custom molded sole or insole prevents or inhibits undesirable motions. For example, if a person has a flat foot, a denser material can be placed on the medial portion of custom molded sole or insole, and a less dense material can be placed on the lateral portion of custom molded sole or insole. Placement of materials having different densities in custom molded sole or insole would prevent the foot from flattening in an undesired manner. Additionally, denser material may be placed by the posterior lateral heel region, and less dense material is placed along the remaining portion of custom molded sole or insole. The general concept of constructing and arranging a sole with different densities is already used in various running shoes to prevent foot pronation. The shoes with soles of varying densities to control foot pronation are called motion controlled shoes. The custom molded sole or insole has further improved on motion controlled shoes by providing a custom molded sole or insole that can be customized in any manner used to customize foot orthotics. The custom molded sole or insole is used to treat any other foot pathology that would benefit from the use of a prescription foot orthotic.

In the context of shoe manufacturing, a computing device may be used to determine operations of various shoe-manufacturing tools. For example, a computing device may be used to control a part-pickup tool or a conveyor that transfers shoe parts from one location to another. In addition, a computing device may be used to control a part-attachment device that attaches (e.g., welds, adheres, stitches, etc.) one shoe part to another shoe part.

1. A method to shape a reformable material, comprising:
generating a 3D model of an object;
adjusting the 3D model to optimize a parameter or treat a patient;
forming a reformable master shape from the adjusted 3D model;
holding a volume of particles inside a container having a first elastomeric membrane surface;
infusing the volume with a liquid to mobilize the volume of particles; and
pressing the reformable master shape into the membrane with atmospheric pressure.

2. The method of claim 1, comprising extracting the liquid through one or more screen elements placed proximal to the volume of particles.

3. The method of claim 1, wherein the atmospheric pressure holds the particles against the elastomeric membrane when the master shape is removed from the membrane.

4. The method of claim 1, comprising heating and driving liquid from the particle volume.

5. The method of claim 1, comprising providing a binding adhesive to lock the particles into a force-resisting mass.

6. The method of claim 1, comprising pressing a complementary shape into the master shape in the membrane.

7. The method of claim 1, wherein the container comprises a rigid outside frame with top and bottom elastomeric membranes, comprising pressing the master shape against the elastomeric membrane.

8. The method of claim 7, wherein the pressing comprises
applying a flexible vacuum cap sealed over the shape and against the elastomeric membrane surface;
evacuating air from a space formed between the membrane and the vacuum cap;
extracting liquid from the volume; and
pressing the particles within the container with atmospheric force acting in opposed directions against the vacuum cap and the bottom surface membrane.

9. The method of claim 7, comprising introducing air into the vacuum cap, and removing the cap and the master shape from the surface of the elastomeric membrane.

10. The method of claim 1, wherein the container is formed against the master shape.

11. The method of claim 10, comprising performing a liquid infusion, a pressing action under atmospheric pressure, and a liquid extraction.

12. The method of claim 10, comprising
placing the master shape on an air-impermeable surface;
placing a membrane of the container over the shape; and
placing a vacuum cap or a vacuum-bagging film over the container to form the elastomeric membrane against the master shape.

13. The method of claim 1, comprising applying an envelope containing a mass of particles and with a vacuum seal on its perimeter to extract air from a space between the master shape and the envelope.

14. The method of claim 1, comprising placing the master shape on the elastomeric surface of a first rigid-framed container and placing a membrane surface of a second container over the master shape.

15. The method of claim 14, wherein the second container fits inside the frame of the first container and a vacuum cap is placed over and sealed outside the second container against the surface membrane of the first container.

16. The method of claim 14, comprising evacuating the volume under the vacuum cap and pressing the master shape between the elastomeric sides of the first and second containers.

17. The method of claim 16, comprising extracting the liquid to press the two volumes of particles together and against the membranes surrounding the contained shape.

18. The method of claim 14, comprising venting the vacuum cap with air and removing the vacuum cap and the first container; and removing the shape from the membrane of the second container, placing the first container adjacent with the second container; and forming a closed, shaped cavity complementary to the surface of the master shape used to form the cavity.

19. The method of claim 14, comprising pressing two identical containers of either the first or the second container around a master shape without using the vacuum cap.

20. The method of claim 19, wherein the containers are joined and sealed by either a seal mounted on one or both of the containers or by seals mounted on a seal ring fitted between the two containers.

21. The method of claim 1, comprising deaerating the volume of particles.

22. A method to form an object, comprising:
generating a 3D model of an object;
adjusting the 3D model to optimize a parameter or treat a patient;
forming a reformable master shape from the adjusted 3D model;
infusing a liquid into a container having a first elastomeric membrane surface;
pressing the master shape into the membrane with atmospheric pressure; and
shaping a reformable material into the object according to the master shape.

23. The method of claim 22, comprising extracting the liquid.

24. The method of claim 22, comprising deaerating the volume of particles;

25. The method of claim 22, comprising extracting the liquid through one or more screen elements placed proximal to the volume of particles.

26. The method of claim 22, comprising heating and driving liquid from the particle volume.

27. The method of claim 22, comprising providing a residue of a binding adhesive to lock the particles into a continuous force-resisting mass.

28. The method of claim 22, comprising impressing a complementary shape to the master shape in the membrane.

29. The method of claim 22, wherein the container comprises a rigid outside frame and top and bottom elastomeric membranes facing the top and bottom surfaces of the container, comprising pressing the master shape against the top elastomeric membrane of the container with atmospheric pressure.

30. The method of claim 29, wherein the pressing comprises
applying a flexible vacuum cap sealed over the shape and against the container top surface membrane;
evacuating air from a space between the top surface membrane and the vacuum cap;
extracting liquid from the volume; and pressing the particles within the container with atmospheric force acting in opposed directions against the vacuum cap and the bottom surface membrane.

31. The method of claim 29, comprising introducing air into the vacuum cap, and removing the cap and the master shape from the formed surface of the elastomeric membrane.

32. The method of claim 22, comprising forming the container against the master shape.

34. The method of claim 32, comprising:
placing the master shape on an air-impermeable surface;
placing a membrane of the container over the shape; and
placing a vacuum cap or a vacuum-bagging film over the container to effect forming of the elastomeric membrane against the master shape.

35. The method of claim 22, comprising applying an envelope containing a mass of particles and with a vacuum seal on the envelope perimeter to extract air from the master shape and the envelope.

36. The method of claim 22, comprising placing the master shape on the top elastomeric surface of a first rigid-framed container and placing a membrane surface of a second container over the master shape.

37. The method of claim 36, wherein the second container fits inside the frame of the first container and a vacuum cap is placed over and sealed outside the second container against the surface membrane of the first container.

38. The method of claim 36, comprising evacuating the volume under the vacuum cap and pressing the master shape between the elastomeric sides of the first and second containers.

39. The method of claim 38, comprising extracting the liquid to press the two volumes of particles together and against the membranes.

40. The method of claim 36, wherein the vacuum cap is vented with air and removed; the top container is removed; and the shape is removed from the membrane of the bottom container, comprising placing the top container over the bottom container; and forming a closed, shaped cavity complementary to the surface of the master shape used to form the cavity.

41. The method of claim 36, wherein the first and second containers are identical, comprising pressing the containers around a master shape without using the vacuum cap.

42. The method of claim 41, wherein the containers are joined and sealed by one of: a seal mounted on one or both containers, a seal mounted on a seal ring fitted between the two containers.

1. A method to form an object, comprising:
infusing a liquid into a container having a frame with first and second elastomeric membranes; a first port to deaerate the volume of particles; and a second port to infuse the volume with a liquid for mobilizing the volume of particles;
generating a 3D model of an object;
adjusting the 3D model to optimize a parameter or treat a patient;
forming a reformable master shape from the adjusted 3D model;
pressing the master shape into the membrane with atmospheric pressure; and
shaping a reformable material into the object according to the master shape.

2. The method of claim 1, comprising extracting the liquid.

3. The method of claim 1, comprising deaerating the volume of particles;

4. The method of claim 1, comprising extracting the liquid through one or more screen elements placed proximal to the volume of particles.

5. The method of claim 1, comprising heating and driving liquid from the particle volume.

6. The method of claim 1, comprising providing a binding adhesive to lock the particles into a force-resisting mass.

7. The method of claim 1, comprising pressing a shape complementary to the master shape in the membrane.

8. The method of claim 1, wherein the container comprises a rigid outside frame and top and bottom elastomeric membranes facing the top and bottom surfaces of the container, comprising pressing the master shape against the top elastomeric membrane of the container with atmospheric pressure.

9. The method of claim 8, wherein the pressing comprises
applying a flexible vacuum cap sealed over the shape and against the container's top surface membrane;
evacuating air from a space between the top membrane and the vacuum cap;
extracting liquid from the volume; and
pressing the particles within the container with atmospheric force acting in opposed directions against the vacuum cap and the bottom surface membrane.

10. The method of claim 8, comprising introducing air into the vacuum cap, and removing the cap and the master shape from the formed surface of the elastomeric membrane.

11. The method of claim 1, wherein the container is formed against the master shape.

12. The method of claim 11, comprising:
placing the master shape on an air-impermeable surface;
placing a membrane of the container over the shape; and
placing a vacuum cap or a vacuum-bagging film over the container to effect forming of the elastomeric membrane against the master shape.

13. The method of claim 1, comprising applying an envelope containing a mass of particles and with a vacuum seal on a perimeter to extract air from between the master shape and the envelope.

14. The method of claim 1, comprising placing the master shape on the top elastomeric surface of a first rigid-framed container and placing a membrane surface of a second container over the master shape.

15. The method of claim 14, wherein the second container fits inside the frame of the first container and a vacuum cap is positioned and sealed outside the second container against the surface membrane of the first container.

16. The method of claim 14, comprising evacuating the volume under the vacuum cap and pressing the master shape between the elastomeric sides of the first and second containers.

17. The method of claim 16, comprising extracting the liquid to press the two volumes of particles together and against the membranes surrounding the shape.

18. The method of claim 14, comprising venting the vacuum cap with air and removing the first container; removing the shape from the membrane of the second container, placing the first container adjacent to the second container; and forming a closed, shaped cavity complementary to the surface of the master shape.

19. The method of claim 14, comprising pressing two identical containers of either the first or the second container around a master shape without using the vacuum cap.

20. The method of claim 19, wherein the containers are joined and sealed by either a seal mounted on one or both of the containers or by seals mounted on a seal ring fitted between the two containers.

21. The method of claim 1, comprising extracting the liquid prior to removing the master shape from the shaped reformable material.

22. The method of claim 1, comprising solidifying the liquid within the shaped reformable material.

23. The method of claim 1, comprising withdrawing the liquid to leave a residue of liquid on the shaped reformable material; and solidifying the residue.

24. The method of claim 1, comprising preforming a material surface over the master shape.

25. The method of claim 24, wherein the preforming comprises one of: thermoforming, additive processing.

26. The method of claim 1, wherein the container walls comprise air and liquid impermeable walls.

27. The method of claim 26, comprising providing an inelastic formable surface conforming to the master shape surface.

28. The method of claim 1, comprising forming a surface over the master shape.

29. The method of claim 1, comprising pressing the shaped material surface against the volume of particles without deforming the shaped material surface.

30. The method of claim 1, comprising:
providing a release surface to the master shape;
pressing the master shape against the volume of particles to form the object with the release surface; and
removing the object using the release surface.

31. The method of claim 30, wherein providing the release surface comprises providing an area around the master shape with a surface element covering the reformable material surface not overlaid with the master shape surface;

1. An apparatus to form an object in accordance with a master shape, comprising:
a computer actuated 3D shape generator to render the master shape;
a container to hold a volume of particles, said container having a first elastomeric membrane surface; a first port to deaerate the volume of particles; and a second port to infuse the volume with a liquid for mobilizing the volume of particles; and
a press coupled to the container to move the master shape into the membrane to shape a reformable material into the object according to the shape generator's master shape.

2. The apparatus of claim 1, comprising one or more screen elements placed proximal to the volume of particles to extract the liquid.

3. The apparatus of claim 1, wherein atmospheric pressure holds the volume of particles in place against the elastomeric membrane when the master shape is removed from the membrane.

4. The apparatus of claim 1, comprising a heater to heat and drive liquid from the particle volume.

6. The apparatus of claim 1, wherein the container comprises a rigid outside frame and top and bottom elastomeric membranes facing the top and bottom surfaces of the container, and wherein the master shape is pressed against the top elastomeric membrane of the container by atmospheric pressure.

7. The apparatus of claim 6, comprising:
a flexible vacuum cap sealed over the shape and against the container's top surface membrane;
a third port to evacuate air from a space between the top membrane and the vacuum cap; and
wherein the particles within the container are pressed with atmospheric force acting in opposed directions against the vacuum cap and the bottom surface membrane.

8. The apparatus of claim 6, wherein air is introduced into the vacuum cap, and wherein the cap and the master shape are removed from a surface of the elastomeric membrane.

9. The apparatus of claim 8, wherein the master shape is placed between an air-impermeable surface and the membrane of the container and wherein a vacuum cap or a vacuum-bagging film is placed over the container to form the elastomeric membrane against the master shape.

10. The apparatus of claim 1, comprising an envelope containing a mass of particles and with a vacuum seal on its perimeter to extract air between the master shape and the envelope.

11. The apparatus of claim 1, comprising placing the master shape on the top elastomeric surface of a first rigid-framed container and placing a membrane surface of a second container over the master shape.

12. The apparatus of claim 11, wherein the second container fits inside the frame of the first container and a vacuum cap is placed over and sealed outside the second container against the surface membrane of the first container.

13. The apparatus of claim 11, comprising a vacuum pump to evacuate the volume under the vacuum cap and press the master shape between the elastomeric sides of the first and second containers.

14. The apparatus of claim 11, comprising a pump to extract the liquid to press the two volumes of particles together and against the membranes surrounding the contained shape.

15. The apparatus of claim 14, wherein the vacuum cap is vented with air and removed; the first container is removed; and the shape is removed from the membrane of the second container and wherein the first container is placed adjacent the second container to form a closed, shaped cavity complementary to the surface of the master shape used to form the cavity.

16. The apparatus of claim 14, wherein the first and second containers are identical and wherein the containers are pressed around a master shape without using the vacuum cap.

17. The apparatus of claim 14, wherein the containers are joined and sealed by either a seal mounted on one or both of the containers or by seals mounted on a seal ring fitted between the containers.

18. The apparatus of claim 14, comprising a seal ring to channel vacuum or air pressure between the containers and to hold the master shape in a predetermined orientation and position between the opposed containers.

19. The apparatus of claim 1, comprising an expander within the container to press the particulate material against cavity walls of the container.

20. The apparatus of claim 1, comprising
a second container cooperating with the first container to form a complementary cavity from the master shape; and
a third container placed in the complementary cavity to replicate the master shape.

21. The apparatus of claim 1, wherein the container comprises a frame.

22. The apparatus of claim 21, wherein the frame comprises one of: a rigid frame, a flexible-edge frame.

23. The apparatus of claim 21, wherein the frame comprises a continuous surface complementary to a master shape's surface.

24. The apparatus of claim 1, comprising a second elastomeric membrane, wherein the elastomeric membranes overlap each other.

25. The apparatus of claim 1, comprising a second elastomeric membrane, wherein the elastomeric membranes abut each other.

26. The apparatus of claim 1, comprising one or more additional containers each having a membrane coupled to the container to form a continuous surface of membranes.

27. The apparatus of claim 1, comprising one or more additional containers to form a shape complementary to the interior of a master cavity.

1. An apparatus to form an object in accordance with a master shape, comprising:
   a computer actuated 3D shape generator to render the master shape;
   a container to hold a volume of particles, said container having a frame with first and second elastomeric membranes; a first port to deaerate the volume of particles; and a second port to infuse the volume with a liquid for mobilizing the volume of particles; and
   a press coupled to the container to move the master shape into the membrane to shape a reformable material into the object according to the master shape.

2. The apparatus of claim 1, wherein the second membrane is bonded to the frame.

3. The apparatus of claim 1, wherein the first membrane is coupled to a seal.

4. The apparatus of claim 1, comprising a clamp to secure at least one membrane to the frame.

5. The apparatus of claim 1, comprising one or more ports on the frame.

6 The apparatus of claim 1, comprising liquid, evacuation, and vacuum-activated seal tubes coupled to the frame.

7. The apparatus of claim 1, comprising a rim evacuation screen element positioned in the frame.

8. The apparatus of claim 1, wherein the frame is one of: a rigid frame, a flexible frame.

9. The apparatus of claim 1, comprising a vacuum activated seal on the frame.

10. The apparatus of claim 1, comprising a tube to evacuate and fill the container.

11. The apparatus of claim 1, comprising double layer screens having feed elements to distribute and extract liquid through the volume of particles.

12. The apparatus of claim 1, comprising one or more screens conformally coupled to the master shape.

13. The apparatus of claim 1, comprising one or more internal screens mounted with the particles flowing on both sides of each internal screen.

14. The apparatus of claim 1, wherein the frame is flexible, comprising one or more containers joined together around the master shape.

15. The apparatus of claim 1, wherein the frame is flexible, comprising one or more containers joined by vacuum seals.

16. The apparatus of claim 1, comprising one or more feed tubes coupled to an interior element inside the membrane.

17. The apparatus of claim 1, comprising a flexible spine element within an interior cavity of the container.

18. The apparatus of claim 1, comprising one or more reinforcement fibers.

19. The apparatus of claim 18, wherein the fibers are distributed in bundles within the volume of particles.

20. The apparatus of claim 1, comprising an air pump to provide internal pressurization.

21. The apparatus of claim 1, comprising a vacuum source to provide a vacuum between a cavity in the container and the container.

22. The apparatus of claim 1, comprising an air pump and a vacuum source to alternately pressurize and vent the container to distribute the volume of particles therein.

23. The apparatus of claim 1, comprising a seal ring.

24. The apparatus of claim 23, wherein the seal rings are mounted.

25. The apparatus of claim 23, wherein the seal comprises a vacuum activated seal.

26. The apparatus of claim 23, comprising a second container joined with the container and wherein a vacuum is formed in an interior of the joined containers.

27. The apparatus of claim 26, wherein the master shape is mounted on the seal ring.

28. The apparatus of claim 26, comprising one or more flanges mounted to control a mating line between opposed membranes of containers.

29. The apparatus of claim 1, comprising a second container positioned within a cavity formed by an outside container.

30. The apparatus of claim 1, comprising a vacuum cap.

31. The apparatus of claim 30, comprising a vacuum seal coupled to the vacuum cap.

32. The apparatus of claim 30, comprising a vacuum tube penetrating through the membrane.

33. The apparatus of claim 1, comprising a vacuum cap with mounted container 245 in place of the membrane 34. The apparatus of claim 1, comprising one or more screen elements placed proximal to the volume of particles to extract the liquid.

35. The apparatus of claim 1, wherein atmospheric pressure holds the volume of particles in place against the elastomeric membrane when the master shape is removed from the membrane.

36. The apparatus of claim 1, comprising a heater to heat and drive liquid from the particle volume.

37. The apparatus of claim 1, wherein the container comprises a rigid outside frame and top and bottom elastomeric membranes facing the top and bottom surfaces of the container, and wherein the master shape is pressed against the top elastomeric membrane of the container with atmospheric pressure.

38. The apparatus of claim 1, comprising an envelope containing a mass of particles and with a vacuum seal on its perimeter to extract air from between the master shape and the envelope.

39. The apparatus of claim 1, comprising placing the master shape on the top elastomeric surface of a first rigid-framed container and placing a membrane surface of a second container over the master shape.

40. The apparatus of claim 1, comprising an expander within the container to press the particulate material against cavity walls of the container.

41. The apparatus of claim 1, comprising
   a second container cooperating with the first container to form a complementary cavity from the master shape; and
   a third container placed in the complementary cavity to replicate the master shape.

42. The apparatus of claim 1, comprising a second elastomeric membrane, wherein the elastomeric membranes overlap or abut each other.

43. The apparatus of claim 1, comprising one or more additional containers each having a membrane coupled to the container to form a continuous surface of membranes.

44. The apparatus of claim 1, comprising one or more additional containers to form a shape complementary to the interior of a master cavity.

1. A base station to form an object in accordance with a master shape, comprising:
   a computer actuated 3D shape generator to render the master shape;
   a liquid receiver;
   a vacuum source to evacuate air from the liquid receiver;
   an air compressor to generate pressurized air; and
   a controller coupled to the liquid receiver, the vacuum source and the air compressor to form the object.

2. The base station of claim 1, comprising one or more tubes to provide vacuum and to control the flow of liquids to and from the receiver.

3. The base station of claim 1, comprising one or more valves coupled to the controller.

4. The base station of claim 1, comprising one or more sensors coupled to the controller.

5. The base station of claim 1, comprising an electrical power supply to operate valves, sensors, the vacuum pump and the air compressor.

6. The base station of claim 1, wherein the controller comprises a menu-driven process controller to operate the base station.

7. The base station of claim 1, comprising a heater to vaporize and expel liquid from the receiver and to heat a reformable material.

8. The base station of claim 7, wherein the reformable material creates contours of the master shape.

9. The base station of claim 7, wherein the reformable material is molded against a complementary surface of an elastomeric membrane.

10. The base station of claim 7, wherein the liquid contains a soluble binder.

11. The base station of claim 10, wherein the binder remains on a shaped volume of particles.

12. The base station of claim 10, wherein the binder locks a shaped volume of particles in place after the liquid is removed.

13. The base station of claim 7, comprising wherein the heater comprises one of: a radiant heater, a convective air heater, a microwave heater, a radio-frequency heater, an inductive heater.

14. The base station of claim 7, comprising the heater comprises one or more heating elements within the container.

15. The base station of claim 7, comprising the heater is controlled by the controller.

16. The base station of claim 1, comprising:
   a container to hold a volume of particles, said container having a frame with first and second elastomeric membranes; a first port to deaerate the volume of particles; and a second port to infuse the volume with a liquid for mobilizing the volume of particles; and
   a press coupled to the container to move the master shape into the membrane to shape a reformable material into the object according to the master shape.

17. The base station of claim 1, comprising
   a container to hold a volume of particles, said container having a first elastomeric membrane surface; a first port to deaerate the volume of particles; and a second port to infuse the volume with a liquid for mobilizing the volume of particles; and
   a press coupled to the container to move the master shape into the membrane to shape a reformable material into the object according to the master shape.

18. The base station of claim 17, wherein the container comprises a rigid outside frame and top and bottom elastomeric membranes facing the top and bottom surfaces of the container, and wherein the master shape is pressed against the top elastomeric membrane of the container by atmospheric pressure.

19. The base station of claim 18, comprising:
   a flexible vacuum cap sealed over the shape and against the container's top membrane;
   a third port to evacuate air from a space between the top membrane and the vacuum cap; and
   a fourth port to extract liquid from the volume;
   wherein the particles within the container are pressed by atmospheric force acting in opposed directions against the vacuum cap and a bottom membrane.

20. The base station of claim 18, wherein the master shape is placed between an air-impermeable surface and the membrane of the container and wherein a vacuum cap or a vacuum-bagging film is placed over the container to form the elastomeric membrane against the master shape.

21. The base station of claim 1, wherein the vacuum pump comprises one of: a mechanical pump, an air driven pump.

22. The base station of claim 1, wherein the vacuum comprises a Venturi pump.

23. The base station of claim 1, comprising a second vacuum pump.

24. The base station of claim 23, comprising isolating valves coupled to the vacuum pumps.

25. The base station of claim 1, comprising a regulator and one or more valves coupled to the vacuum pump to pressurize a liquid tank.

26. The base station of claim 25, comprising a vent valve coupled to the liquid tank to cycle from a vacuum source to a pressure source.

27. The base station of claim 25, comprising a three-way valve to route air and vacuum to the liquid tank.

28. The base station of claim 25, comprising a filter coupled to the liquid tank to prevent particulate carryover.

29. The base station of claim 1, comprising an air-liquid separator.

30. The base station of claim 1, comprising a level indicator.

31. The base station of claim 1, comprising a vacuum sensor coupled to the controller for process control.

32. The base station of claim 1, comprising a heat exchanger coupled to the container to condense vapor.

33. The base station of claim 1, comprising one or more outside containers in combination forming a cavity and an inside container in the formed cavity.

34. The base station of claim 1, comprising a slurry transfer tank coupled to the container.

35. The base station of claim 1, comprising one or more containers coupled to the container.

36. The base station of claim 35, wherein the containers are mated with a seal ring.

1. A method to shape a reformable material, comprising:
   generating a 3D model of an object;
   adjusting the 3D model to optimize a parameter or treat a wearer;
   forming a reformable master shape from the adjusted 3D model;
   holding a volume of particles inside a container having a first elastomeric membrane surface; and infusing the volume of particles with a liquid;
   agitating the liquid to provide one or more surges of liquid to mobilize the volume of particles; and pressing the master shape into the membrane with atmospheric pressure.

2. The method of claim 1, comprising providing locally distributed surges.

3. The method of claim 1, comprising providing globally distributed surges.

4. The method of claim 1, wherein the one or more surges exert differential liquid forces on particles to displace them relative to one another and facilitate their movement into a closely-packed volume.

5. The method of claim 1, comprising providing a differential pressure between a master shape side and a liquid-particle side of the membrane.

6. The method of claim 1, comprising decreasing the pressure between a vacuum cap and the membrane to move the membrane in a first direction.

7. The method of claim 1, comprising increasing the pressure between a vacuum cap and the membrane to move the membrane in a second direction.

8. The method of claim 6, wherein membrane is free to move relative to master shape.

9. The method of claim 1, wherein the liquid moves through particles toward membrane, and wherein the particles move toward the membrane.

10. The method of claim 1, comprising removing excess liquid and leaving particles against the membrane.

11. The method of claim 1, comprising evacuating air from space between the membranes.

12. The method of claim 1, comprising packing the particles against the membranes and the master shape.

13. The method of claim 1, comprising extracting the liquid with the vacuum cap and membrane pressed against the master shape to pack the particles against the membranes and the master shape.

14. The method of claim 1, wherein the agitating comprises pulsing the liquid.

15. The method of claim 1, wherein the agitating comprises vibrating the liquid.

16. The method of claim 15, comprising adjusting a vibration frequency to displace one particle relative to another to keep the particles moving freely in relation to one another.

17. The method of claim 1, wherein amplitude of liquid pulsation is proximally equal to a diameter of the particles.

18. The method of claim 1, comprising generating a first surge of liquid towards a desired transport direction.

19. The method of claim 18, comprising generating a second surge smaller than the first surge in an opposite direction to the transport direction.

20. The method of claim 1, comprising agitating the liquid to minimize blockage.

21. The method of claim 1, comprising maintaining the volume of the container constant and completely filled to force the particles against the master shape.

22. The method of claim 21, comprising:
extracting transitional liquid from the container; and
adding new liquid equal in volume of the transition liquid.

1. A shape-reformable composition, comprising:
a carrier medium having a carrier density; and
a plurality of solid bodies having a density substantially similar to the carrier density, said solid bodies being transitionable from a formable state to a three dimensional solid shape.

2. The composition of claim 1, wherein the carrier medium fills voids or interstices between the solid bodies.

3. The composition of claim 1, wherein the voids or interstices are free of air or gas bubbles.

4. The composition of claim 1, wherein the solid bodies comprise a near-liquid or fluent mobility during the formable state.

5. The composition of claim 1, wherein the solid bodies transition to the solid shape through an introduction and an extraction of a predetermined amount of the carrier medium.

6. The composition of claim 1, wherein solid bodies are positioned in a container having a first elastomeric membrane surface.

7. The composition of claim 6, wherein liquid is introduced to mobilize the volume of particles.

8. The composition of claim 6, wherein a master shape is pressed into the membrane with atmospheric pressure.

9. The composition of claim 1, wherein the solid shape comprises a stable, force-resisting shape.

10. The composition of claim 1, wherein the solid bodies and carrier medium form a reversible state-changeable mixture 11. The composition of claim 1, wherein the carrier medium comprises a liquid.

12. The composition of claim 1, wherein the carrier medium comprises a gaseous froth.

13. The composition of claim 1, wherein the shape comprises a reformable mold.

14. The composition of claim 1, comprising a reusable template to capture dimensions of impressed shapes for transfer to a mold.

15. The composition of claim 1, comprising a binder to bind the solid bodies.

16. The composition of claim 15, wherein the binder comprises one of: a TEOS binder, an ethanol based material, a eutectic metal, and a fiber.

17. The composition of claim 15, wherein the binder comprises a thermally conductive particle.

18. The composition of claim 15, wherein the binder comprises one or more electrically heated particles.

19. The composition of claim 18, wherein the particle comprise a resistive coating for resistive heating.

20. The composition of claim 15, wherein the binder comprises an elastomeric binder.

21. The composition of claim 15, wherein the binder is hardened with introduced liquid or gas after forming.

22. The composition of claim 15, wherein the binder is hardened with hot air through the particles.

23. The composition of claim 22, wherein the binder is formed at a pressure above atmospheric pressure.

24. The composition of claim 15, wherein a pH value for the binder is increased or decreased.

25. The composition of claim 1, comprising a surface coating on shaped solid bodies to add smoothness, toughness, and better release properties for the composition.

1. A vacuum activated seal for a container, comprising:
a channel having one or more legs angled outwardly and spaced apart, said legs having contact areas adapted to be pressed against a surface with a greater force per unit area than atmospheric pressure; said channel having an opening therein; and
a tube penetrating from the outside of the channel to the inside of the channel through the opening.

2. The seal of claim 1, wherein the channel is mounted as a continuous ring.

3. The seal of claim 2, wherein the ring is positioned on the container perimeter.

4. The seal of claim 1, wherein the ring is positioned on a flange.

5. The seal of claim 1, wherein the legs are forced against the surface by atmospheric pressure when the channel is evacuated.

6. The seal of claim 1, wherein a total unit area on the back of the channel exceeds the total unit area of the leg area in contact with the surface.

7. The seal of claim 1, wherein the seal is used to enclose a volume between two air-impermeable elements.

8. The seal of claim 7, wherein the seal prevents leakage from the outside to the inside of the volume as a contact pressure exceeds atmospheric pressure.

8A. The seal of claim 8, wherein the contact pressure comprises applying a vacuum on the volume.

9. The seal of claim 1, wherein the seal scavenges air from the outside if a leak occurs through imperfections in the seal or the surface.

10. The seal of claim 1, wherein the surface of the seal is placed against or pressed down against a smooth air-impermeable surface.

10. The seal of claim 1, wherein the surface comprises one of: a flange-mounted membrane, a seal ring, a second seal.

11 The seal of claim 1, wherein a vacuum is introduced through the tube to extract air from the inside of the seal.

12. The seal of claim 1, wherein atmospheric pressure acting on the back of the channel presses the legs of the channel against the surface.

13. The seal of claim 1, wherein the channel comprises a resilient material.

14. The seal of claim 1, wherein the channel comprises an elastomeric material.

15. The seal of claim 1, wherein the channel comprises rubber.

16. The seal of claim 1, comprising a container to hold a volume of particles, said container having a first elastomeric membrane surface; a first port to deaerate the volume of particles; and a second port to infuse the volume with a liquid for mobilizing the volume of particles.

17. The seal of claim 16, comprising a press coupled to the container to move the master shape into the membrane to shape a reformable material into the object according to the master shape.

18. The seal of claim 16, comprising one or more screen elements placed proximal to the volume of particles to extract the liquid.

19. The seal of claim 16, wherein atmospheric pressure holds the volume of particles in place against the elastomeric membrane when the master shape is removed from the membrane.

20. An apparatus to form an object in accordance with a master shape, comprising:
  a container to hold a volume of particles, said container having a first elastomeric membrane surface; a first port to deaerate the volume of particles; and a second port to infuse the volume with a liquid for mobilizing the volume of particles; and a vacuum activated seal for the container, including: a channel having one or more legs angled outwardly and spaced apart, said legs having contact areas adapted to be pressed against a surface with a greater force per unit area than atmospheric pressure; said channel having an opening therein; and a tube penetrating from the outside of the channel to the inside of the channel through the opening; and
  a press coupled to the container to move the master shape into the membrane to shape a reformable material into the object according to the master shape.

It will be understood that each of the elements described above, or two or more together, also may find a useful application in other types of constructions differing from the types described above. Many different arrangements of the various components depicted, as well as components not shown, are possible without departing from the scope of the claims below. Aspects of our technology have been described with the intent to be illustrative rather than restrictive. Alternative aspects will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The above exemplary systems and methods have been described to provide those skilled in the art with the information needed to apply the novel principles and to construct and use such specialized components as are required. However, it is to be understood that the system can be carried out by specifically different equipment and devices, and that various modifications, both as to the equipment details and operating procedures, can be accomplished without departing from the scope of the system itself. Without further analysis, the foregoing will so fully reveal the gist of the present system that others can, by applying current knowledge, readily adapt it for various applications without omitting features that, from the standpoint of prior art, fairly constitute essential characteristics of the generic or specific aspects of this system and, therefore, such adaptations should and are intended to be comprehended within the meaning and range of equivalence of the following claims.

What is claimed is:

1. A method for forming a customized footwear, comprising:
  receiving a foot model into memory of a processor;
  coupling the foot model to a shoe model;
  modifying the foot model to support a heel, a foot arch and a ball area of the foot; and
  fabricating a sole or insole in a reformable structure, wherein the reformable structure is reusable.

2. The method of claim 1, comprising fabricating the sole or insole by:
  forming a reformable master shape from the foot model;
  holding a volume of particles inside a container;
  infusing the volume with a liquid to mobilize the volume of particles;
  pressing the reformable master shape into the membrane with atmospheric pressure to form a mold of the sole; and
  depositing a sole material into the mold.

3. The method of claim 1, comprising providing a bed of computer controlled bed of pins to form the reformable master shape.

4. The method of claim 1, comprising fabricating the sole or insole using additive manufacturing.

5. The method of claim 1, comprising providing forming one or more perspiration openings on the sole or insole.

6. The method of claim 1, comprising structural lattice holes selectively permeable to air but not to water, wherein said holes open along part of the outer edge of said the sole or insole and wherein at least one cavity is provided inside said sole or insole wherein said holes open.

7. The method of claim 1, comprising capturing from one or more a mobile phone images of a user's foot and generating the foot model from the one or more images.

8. The method of claim 1, comprising: capturing a foot pressure data from walking or running; and applying the foot pressure data to a 3D model to generate a foot support shape on the sole or insole.

9. The method of claim 1, comprising designing a sole shape or insole shape for energy absorption.

10. The method of claim 1, comprising attaching an upper to the sole.

11. A system, comprising:
a mobile phone to scan a foot model;
a software to place the foot model proximal to a shoe model, wherein the software creates a digital structure based on the foot model to support a heel, a foot arch and a ball area of the foot; and
a fabricator with a computer controlled bed of pins to form a sole or insole shape, the fabricator receiving the digital structure and forming a sole or insole to provide foot support.

12. The system of claim 11, wherein the fabricator uses additive manufacturing.

13. The system of claim 11, wherein one or more perspiration openings are formed on the high heel sole or insole.

14. The system of claim 11, wherein the digital structure comprises holes selectively permeable to air but not to water, wherein said holes open along part of the outer edge of said the sole or insole and wherein at least one cavity is provided inside said sole or insole wherein said holes open.

15. The system of claim 11, wherein the mobile phone captures from mobile phone images of a user's foot and generates the foot model from the images.

16. The system of claim 11, comprising: capturing foot pressure data during walking or running; and applying the foot pressure data to the 3D model to generate a foot support shape on the sole or insole.

17. The system of claim 11, wherein the software generates a sole shape or an insole shape for energy absorption.

18. The system of claim 11, comprising an upper coupled to the sole.

* * * * *